(12) United States Patent
Beswick et al.

(10) Patent No.: US 7,932,282 B2
(45) Date of Patent: Apr. 26, 2011

(54) IMIDAZOLIDINE CARBOXAMIDE DERIVATIVES AS P2X7 MODULATORS

(75) Inventors: Paul John Beswick, Harlow (GB);
David Kenneth Dean, Harlow (GB);
Robert James Gleave, Harlow (GB);
Andrew Peter Moses, Harlow (GB);
Daryl Simon Walter, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/594,381

(22) PCT Filed: Apr. 2, 2008

(86) PCT No.: PCT/EP2008/053962
§ 371 (c)(1),
(2), (4) Date: Oct. 2, 2009

(87) PCT Pub. No.: WO2008/119825
PCT Pub. Date: Oct. 9, 2008

(65) Prior Publication Data
US 2010/0075968 A1    Mar. 25, 2010

(30) Foreign Application Priority Data

Apr. 3, 2007 (GB) .................................. 0706501.4
Oct. 22, 2007 (GB) .................................. 0720653.5
Mar. 20, 2008 (GB) .................................. 0805272.2
Mar. 26, 2008 (GB) .................................. 0805504.8

(51) Int. Cl.
*A61K 31/4164* (2006.01)
*C07D 233/02* (2006.01)
(52) U.S. Cl. ..................................... 514/400; 548/322.5
(58) Field of Classification Search .................. 514/400; 548/322.5
See application file for complete search history.

(56) References Cited

U.S. PATENT DOCUMENTS

| 2005/0026916 A1 | 2/2005 | Shum et al. ................. 514/235.5 |
| 2008/0009541 A1 | 1/2008 | Chambers et al. ............ 514/423 |

FOREIGN PATENT DOCUMENTS

| JP | 5024287 A | 3/1975 |
| WO | WO 99/29686 A | 6/1999 |
| WO | WO 01/10799 A1 | 2/2001 |
| WO | WO 2008/003697 A1 | 1/2008 |

*Primary Examiner* — Yong Chu
*Assistant Examiner* — Samantha L Shterengarts
(74) *Attorney, Agent, or Firm* — Duke M. Fitch; Kathryn L. Sieburth; John Lemanowicz

(57) ABSTRACT

The present invention relates to a compound of formula (I) or a pharmaceutically acceptable salt thereof:

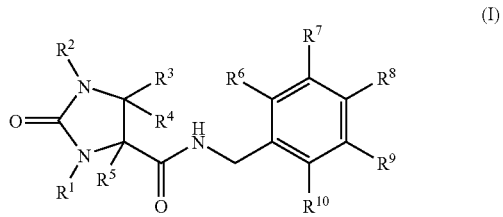

(I)

The compounds or salts modulate P2X7 receptor function and are capable of antagonizing the effects of ATP at the P2X7 receptor (P2X7 receptor antagonists). The invention also provides the use of such compounds or salts, or pharmaceutical compositions thereof, in the treatment or prevention of disorders/diseases mediated by the P2X7 receptor, for example pain, inflammation or a neurodegenerative disease, in particular pain such as inflammatory pain, neuropathic pain or visceral pain.

26 Claims, No Drawings

IMIDAZOLIDINE CARBOXAMIDE DERIVATIVES AS P2X7 MODULATORS

This application is a 371 of International Application No. PCT/EP2008/053962, filed 2 Apr. 2008, which claims the priority of GB Application No. 0805504.8, filed 26 Mar. 2008, GB Application No. 0805272.2, filed 20 Mar. 2008, GB 0720653.5, filed 22 Oct. 2007, and GB 0706501.4, filed 3 Apr. 2007, which are incorporated herein in their entirety.

The present invention relates to heterocyclic amide derivatives which modulate P2X7 receptor function and are capable of antagonizing the effects of ATP at the P2X7 receptor ("P2X7 receptor antagonists"); to processes for their preparation; to pharmaceutical compositions containing them; and to the use of such compounds in therapy.

The P2X7 receptor is a ligand-gated ion-channel which is expressed in cells of the hematopoietic lineage, e.g. macrophages, microglia, mast cells, and lymphocytes (T and B) (see, for example, Collo et al., *Neuropharmacology*, Vol. 36, pp. 1277-1283 (1997)), and is activated by extracellular nucleotides, particularly adenosine triphosphate (ATP). Activation of P2X7 receptors has been implicated in giant cell formation, degranulation, cytolytic cell death, CD62L shedding, regulation of cell proliferation, and release of proinflammatory cytokines such as interleukin 1 (IL-1β) and tumour necrosis factor (TNFα) (e.g. Hide et al., *Journal of Neurochemistry*, Vol. 75., pp. 965-972 (2000)). P2X7 receptors are also located on antigen presenting cells, keratinocytes, parotid cells, hepatocytes, erythrocytes, erythroleukaemic cells, monocytes, fibroblasts, bone marrow cells, neurones, and renal mesangial cells. Furthermore, the P2X7 receptor is expressed by presynaptic terminals in the central and peripheral nervous systems and has been shown to mediate glutamate release in glial cells (Anderson, C. et al., *Drug. Dev. Res.*, Vol. 50, page 92 (2000)).

The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders. Recent preclinical in vivo studies have directly implicated the P2X7 receptor in both inflammatory and neuropathic pain (Dell'Antonio et al., *Neurosci. Lett.*, 327, pp. 87-90, 2002; Chessell, I P. et al., *Pain*, 114, pp. 386-396, 2005) while there is in vitro evidence that P2X7 receptors mediate microglial cell induced death of cortical neurons (Skaper, S. D. et al., Program No. 937.7. 2005 *Abstract Viewer/Itinerary Planner*. Washington, D.C.: Society for Neuroscience, 2005. Online). In addition, up-regulation of the P2X7 receptor has been observed around βamyloid plaques in a mouse model of Alzheimer's disease (Parvathenani, L. et al., *J. Biol. Chem.*, Vol. 278(15), pp. 13309-13317, 2003).

WO 01/10799 A1 (Aventis Pharmaceutical Products Inc.) discloses methods for preparing N-[(aliphatic or aromatic) carbonyl]-2-aminoacetamide compounds and for cyclising such compounds. JP 50-24287 (Sumitomo Chemical Co., Ltd.) discloses certain 5-substituted 2-oxo-4-imidazolidinecarboxamide compounds.

The present invention provides compounds which modulate P2X7 receptor function and are capable of antagonizing the effects of ATP at the P2X7 receptor ("P2X7 receptor antagonists").

A first aspect of the invention provides a compound of formula (I) or a pharmaceutically acceptable salt thereof:

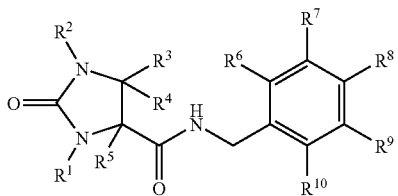

wherein:

$R^1$ represents hydrogen, $C_{1-6}$ alkyl (e.g. methyl or ethyl), $C_{2-6}$ alkenyl, $C_{2-6}$ alkynyl, $C_{3-6}$ cycloalkyl, $C_{3-6}$ cycloalkylmethyl-, pyridinylmethyl- or benzyl, and wherein any of said $C_{1-6}$ alkyl, $C_{2-6}$ alkenyl, $C_{2-6}$ alkynyl, $C_{3-6}$ cycloalkyl, $C_{3-6}$ cycloalkylmethyl-, pyridinylmethyl- or benzyl is optionally substituted with 1, 2 or 3 (e.g. 1 or 2) halogen (e.g. fluorine or chlorine) atoms; or an unsubstituted phenyl;

$R^2$ represents hydrogen, $C_{1-6}$ alkyl (e.g. methyl, ethyl, n-propyl or i-propyl), $C_{2-6}$ alkenyl, $C_{2-6}$ alkynyl, $C_{3-6}$ cycloalkyl, $C_{3-6}$ cycloalkylmethyl-, $-(CR^xR^y)_n-NR^{11}R^{12}$, $C_{6-10}$ arylmethyl-, heterocyclyl-$(CR^xR^y)_n-$ or heteroaryl-$(CR^xR^y)_n-$; and wherein any of said $C_{1-6}$ alkyl, $C_{2-6}$ alkenyl, $C_{2-6}$ alkynyl, $C_{3-6}$ cycloalkyl, $C_{3-6}$ cycloalkylmethyl-, $C_{6-10}$ arylmethyl-, heterocyclyl-$(CR^xR^y)_n-$ or heteroaryl-$(CR^xR^y)_n-$ is optionally substituted with 1, 2 or 3 (e.g. 1 or 2) halogen (e.g. fluorine or chlorine) atoms or $C_{1-6}$ alkyl (e.g. methyl) groups, or the heteroaryl-$(CR^xR^y)_n-$ is optionally substituted on the heteroaryl ring with one $C_{1-3}$ alkoxy (e.g. methoxy), cyano or trifluoromethyl group;

$R^3$, $R^4$ and $R^5$ independently represent hydrogen, fluorine or methyl;

$R^6$, $R^7$, $R^8$, $R^9$ and $R^{10}$ independently represent hydrogen, halogen, cyano, $C_{1-6}$ alkyl, $C_{2-6}$ alkenyl, $C_{2-6}$ alkynyl, $C_{3-6}$ cycloalkyl or phenyl, and wherein any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms; or $R^9$ and $R^{10}$ together with the carbon atoms to which they are attached form a benzene ring which is optionally substituted with 1, 2 or 3 halogen atoms;

$R^x$ and $R^y$ independently represent hydrogen or $C_{1-6}$ alkyl;

$R^{11}$ and $R^{12}$ independently represent hydrogen or $C_{1-6}$ alkyl; and n represents an integer from 0 to 4;

with the proviso that when $R^6$ and $R^{10}$ independently represent hydrogen or fluorine, at least one of $R^7$, $R^8$ and $R^9$ is a halogen atom, or only one of $R^7$, $R^8$ and $R^9$ is a $CF_3$ group.

In a particular embodiment, $R^2$ represents hydrogen, $C_{1-6}$ alkyl (e.g. methyl, ethyl, n-propyl or i-propyl), $C_{2-6}$ alkenyl, $C_{2-6}$ alkynyl, $C_{3-6}$ cycloalkyl, $C_{3-6}$ cycloalkylmethyl-, $-(CR^xR^y)_n-NR^{11}R^{12}$, $C_{6-10}$ arylmethyl-, heterocyclyl-$(CR^xR^y)_n-$ or heteroaryl-$(CR^xR^y)_n-$; and wherein any of said $C_{1-6}$ alkyl, $C_{2-6}$ alkenyl, $C_{2-6}$ alkynyl, $C_{3-6}$ cycloalkyl, $C_{3-6}$ cycloalkylmethyl-, $C_{6-10}$ arylmethyl-, heterocyclyl-$(CR^xR^y)_n-$ or heteroaryl-$(CR^xR^y)_n-$ is optionally substituted with 1, 2 or 3 (e.g. 1 or 2) halogen (e.g. fluorine or chlorine) atoms or $C_{1-6}$ alkyl (e.g. methyl) groups.

In one embodiment, there is provided a compound of formula (I) or a pharmaceutically acceptable salt thereof:

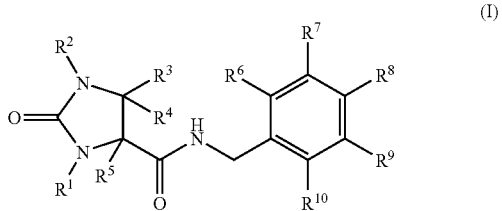

(I)

wherein:

$R^1$ represents $C_{1-6}$ alkyl (e.g. methyl or ethyl), $C_{2-6}$ alkenyl, $C_{2-6}$ alkynyl, $C_{3-6}$ cycloalkyl, $C_{3-6}$ cycloalkylmethyl-, pyridinylmethyl- or benzyl, any of which is optionally substituted with 1, 2 or 3 (e.g. 1 or 2) halogen (e.g. fluorine or chlorine) atoms; or an unsubstituted phenyl;

$R^2$ represents hydrogen, $C_{1-6}$ alkyl (e.g. methyl, ethyl, n-propyl or i-propyl), $C_{2-6}$ alkenyl, $C_{2-6}$ alkynyl, $C_{3-6}$ cycloalkylmethyl- or $C_{6-10}$ arylmethyl-; and wherein any of said $C_{1-6}$ alkyl, $C_{2-6}$ alkenyl, $C_{2-6}$ alkynyl, $C_{3-6}$ cycloalkylmethyl- or $C_{6-10}$ arylmethyl- is optionally substituted with 1, 2 or 3 (e.g. 1 or 2) halogen (e.g. fluorine or chlorine) atoms;

$R^3$, $R^4$ and $R^5$ independently represent hydrogen, fluorine or methyl; and $R^6$, $R^7$, $R^8$, $R^9$ and $R^{10}$ independently represent hydrogen, halogen, cyano, $C_{1-6}$ alkyl, $C_{2-6}$ alkenyl, $C_{2-6}$ alkynyl, $C_{3-6}$ cycloalkyl or phenyl, and wherein any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms; or $R^9$ and $R^{10}$ together with the carbon atoms to which they are attached form a benzene ring which is optionally substituted with 1, 2 or 3 halogen atoms;

with the proviso that when $R^6$ and $R^{10}$ independently represent hydrogen or fluorine, at least one of $R^7$, $R^8$ and $R^9$ is a halogen atom, or only one of $R^7$, $R^8$ and $R^9$ is a $CF_3$ group.

As used herein, the term "alkyl" (when used as a group or as part of a group) refers to a straight or branched hydrocarbon chain containing the specified number of carbon atoms. For example, $C_{1-6}$ alkyl means a straight or branched hydrocarbon chain containing at least 1 and at most 6 carbon atoms. Examples of alkyl include, but are not limited to; methyl (Me), ethyl (Et), n-propyl, i-propyl, t-butyl, n-hexyl and i-hexyl.

As used herein, the term "alkenyl" refers to a straight or branched hydrocarbon chain containing the specified number of carbon atoms wherein at least one carbon-carbon bond is a double bond. Examples of alkenyl include, but are not limited to ethenyl, propenyl, n-butenyl, i-butenyl, n-pentenyl and i-pentenyl.

As used herein, the term "alkynyl" refers to a straight or branched hydrocarbon chain containing the specified number of carbon atoms wherein at least one carbon-carbon bond is a triple bond. Examples of alkynyl include, but are not limited to ethynyl, propynyl, butynyl, i-pentynyl, n-pentynyl, i-hexynyl and n-hexynyl.

The term 'cycloalkyl' unless otherwise stated means a closed 3 to 6 membered non-aromatic ring, for example cyclopropyl, cyclobutyl, cyclopentyl or cyclohexyl.

The term 'aryl' as used herein refers to a $C_{6-10}$ monocyclic or bicyclic hydrocarbon ring wherein at least one ring is aromatic. Examples of such groups include phenyl and naphthyl.

The term 'halogen' is used herein to describe, unless otherwise stated, a group selected from fluorine, chlorine, bromine or iodine.

The term "heteroaryl" as used herein means a 5 to 6 membered monocyclic aromatic or a fused 8 to 10 membered bicyclic aromatic ring system containing 1 to 3 heteroatoms selected from oxygen, nitrogen and sulfur. Suitable examples of such monocyclic aromatic rings include thienyl, furanyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused bicyclic aromatic ring systems include quinolinyl, isoquinolinyl, quinazolinyl, quinoxalinyl, cinnolinyl, naphthyridinyl, indolyl, indazolyl, pyrrolopyridinyl, benzofuranyl, benzodioxinyl, benzothienyl, benzimidazolyl, benzoxazolyl, benzisoxazolyl, benzothiazolyl, benzisothiazolyl, benzoxadiazolyl, benzothiadiazolyl and the like. Heteroaryl groups, as described above, may be linked to the remainder of the molecule via a carbon atom or, when present, via a suitable nitrogen atom except where otherwise indicated above.

The term 'heterocyclyl' refers to a 4-7 membered monocyclic ring or a fused 8-12 membered bicyclic ring which may be saturated or partially unsaturated containing 1 to 4 heteroatoms selected from oxygen, nitrogen or sulphur. Examples of such monocyclic rings include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like. Examples of such bicyclic rings include indolinyl, isoindolinyl, benzopyranyl, quinuclidinyl, 2,3,4,5-tetrahydro-1H-3-benzazepine, tetrahydroisoquinolinyl and the like.

It is to be understood that the present invention covers and discloses all possible combinations of particular, preferred, suitable, or other embodiments of groups or features (e.g. of $R^1$, $R^2$, $R^x$, $R^y$, $R^3$, $R^4$, $R^5$, $R^6$, $R^7$, $R^8$, $R^9$, $R^{10}$, $R^{11}$, $R^{12}$, $R^{11}$, $R^{12}$ and/or n), e.g. all possible combinations of embodiments of different groups or features, which embodiments are described herein.

In certain particular embodiments of the invention, $R^1$ represents $C_{1-6}$ alkyl (e.g. methyl or ethyl), $C_{2-6}$ alkenyl, $C_{2-6}$ alkynyl, $C_{3-6}$ cycloalkyl, $C_{3-6}$ cycloalkylmethyl-, pyridinylmethyl- or benzyl, any of which is optionally substituted with 1, 2 or 3 (e.g. 1 or 2) halogen (e.g. fluorine or chlorine) atoms; or an unsubstituted phenyl.

In one embodiment of the invention, $R^1$ represents unsubstituted $C_{1-6}$ alkyl (e.g. methyl or ethyl) or $C_{3-6}$ cycloalkyl; or a benzyl optionally substituted with 1, 2 or 3 halogen (e.g. fluorine or chlorine) atoms. In a particular embodiment $R^1$ represents $C_{1-4}$ alkyl (e.g. methyl or ethyl). In a further embodiment, $R^1$ represents hydrogen or methyl.

In a particular embodiment of the invention, $R^1$ represents methyl, ethyl, or ethyl substituted with 1, 2 or 3 fluorine atoms (e.g. methyl, ethyl, —$CH_2$—$CF_3$, —$CH_2$—$CHF_2$ or —$CH_2$—$CH_2F$).

In a preferred embodiment, $R^1$ represents methyl or ethyl, in particular methyl.

In certain particular embodiments of the invention, $R^2$ represents hydrogen, $C_{1-6}$ alkyl (e.g. methyl, ethyl, n-propyl or i-propyl), $C_{2-6}$ alkenyl, $C_{2-6}$ alkynyl, $C_{3-6}$ cycloalkyl (e.g. cyclopentyl), $C_{3-6}$ cycloalkylmethyl- (e.g. cyclopropylmethyl- or cyclobutylmethyl-), —$(CR^xR^y)_n$—$NR^{11}R^{12}$, $C_{6-10}$ arylmethyl-, heterocyclyl-$(CR^xR^y)_n$— or heteroaryl-$(CR^xR^y)_n$—; and wherein said $C_{1-6}$ alkyl is optionally substituted with 1, 2 or 3 (e.g. 1 or 2) halogen (e.g. fluorine) atoms, and wherein the heteroaryl-$(CR^xR^y)_n$— is optionally substituted (e.g. on the heteroaryl ring) with 1, 2 or 3 (e.g. 1 or 2, e.g.

1) halogen (e.g. fluorine or chlorine) atoms or $C_{1-6}$ alkyl (e.g. methyl, ethyl, n-propyl or i-propyl, e.g. methyl) groups, or the heteroaryl-$(CR^xR^y)_n$— is optionally substituted on the heteroaryl ring with one $C_{1-3}$ alkoxy (e.g. methoxy), cyano or trifluoromethyl group.

In certain particular embodiments of the invention, $R^2$ represents hydrogen, $C_{1-6}$ alkyl (e.g. methyl, ethyl, n-propyl or i-propyl), $C_{2-6}$ alkenyl, $C_{2-6}$ alkynyl, $C_{3-6}$ cycloalkyl (e.g. cyclopentyl), $C_{3-6}$ cycloalkylmethyl- (e.g. cyclopropylmethyl- or cyclobutylmethyl-), —$(CR^xR^y)_n$—$NR^{11}R^{12}$, $C_{6-10}$ arylmethyl-, heterocyclyl-$(CR^xR^y)_n$— or heteroaryl-$(CR^xR^y)_n$—; and wherein any of said $C_{1-6}$ alkyl, $C_{2-6}$ alkenyl, $C_{2-6}$ alkynyl, $C_{3-6}$ cycloalkyl, $C_{3-6}$ cycloalkylmethyl-, $C_{6-10}$ arylmethyl-, heterocyclyl-$(CR^xR^y)_n$— or heteroaryl-$(CR^xR^y)_n$— is optionally substituted with 1, 2 or 3 (e.g. 1 or 2) halogen (e.g. fluorine or chlorine) atoms or methyl groups, or the heteroaryl-$(CR^xR^y)_n$— is optionally substituted on the heteroaryl ring with one $C_{1-3}$ alkoxy (e.g. methoxy), cyano or trifluoromethyl group.

In certain particular embodiments of the invention, $R^2$ represents hydrogen or unsubstituted $C_{1-6}$ alkyl (e.g. methyl, ethyl, n-propyl or i-propyl), benzyl or $C_{3-6}$ cycloalkylmethyl- (e.g. cyclopropylmethyl- or cyclobutylmethyl-). In another embodiment $R^2$ represents hydrogen or $C_{1-4}$ alkyl (e.g. methyl, ethyl, n-propyl or i-propyl).

In a more particular embodiment, $R^2$ represents hydrogen or methyl. In a preferred embodiment, $R^2$ represents methyl.

In a particular embodiment, $R^2$ represents hydrogen, $C_{1-6}$ alkyl (e.g. methyl or ethyl), heterocyclyl-$(CR^xR^y)_n$— or heteroaryl-$(CR^xR^y)_n$—; and any of said $C_{1-6}$ alkyl, heterocyclyl-$(CR^xR^y)_n$— or heteroaryl-$(CR^xR^y)_n$— is optionally substituted with 1, 2 or 3 halogen (e.g. fluorine or chlorine, in particular fluorine) atoms or $C_{1-6}$ alkyl (e.g. methyl, ethyl, n-propyl or i-propyl, in particular methyl) groups.

In a particular embodiment of the invention, $R^2$ represents hydrogen, methyl, ethyl, or ethyl substituted with 1, 2 or 3 fluorine atoms (e.g. hydrogen, methyl, ethyl, —$CH_2$—$CF_3$, —$CH_2$—$CHF_2$ or —$CH_2$—$CH_2F$).

In a particular embodiment, $R^2$ represents heteroaryl (e.g. pyridinyl, pyrimidinyl, imidazolyl or pyrazolyl) optionally substituted with 1, 2 or 3 $C_{1-6}$ alkyl groups (e.g. methyl, ethyl, n-propyl or i-propyl, in particular methyl).

In a particular embodiment, $R^2$ represents pyridinyl, pyrimidinyl, imidazolyl or pyrazolyl, wherein any of said groups are optionally substituted with 1 or 2 (e.g. one) fluorine or chlorine (e.g. fluorine) atoms, with 1 or 2 (e.g. one) methyl, ethyl, n-propyl or i-propyl (in particular methyl) groups, or with one $C_{1-3}$ alkoxy (e.g. methoxy), cyano or trifluoromethyl group.

In a particular embodiment, $R^2$ represents heteroarylmethyl- (e.g. pyridinylmethyl or imidazolylmethyl) optionally substituted with 1, 2 or 3 $C_{1-6}$ alkyl groups (e.g. methyl).

In a particular embodiment, $R^2$ represents heterocyclyl-$(CR^xR^y)_n$— (e.g. piperidinyl, morpholinyl-$(CH_2)_2$— or morpholinyl-$(CH_2)_3$—). In one embodiment, n represents 2 or 3.

In a particular embodiment, $R^x$ and $R^y$ both represent hydrogen.

In a particular embodiment, n represents 0 or 1, more particularly 0.

In a particular embodiment, $R^1$ and $R^2$ do not both represent hydrogen.

In a preferred embodiment of the invention, $R^1$ and $R^2$ both represent methyl.

In a particular embodiment of the invention, $R^1$ represents methyl and $R^2$ represents hydrogen.

In a particular embodiment of the invention, $R^3$ and $R^4$ both represent hydrogen. In a particular embodiment, $R^5$ represents hydrogen. In a more particular embodiment, $R^3$, $R^4$ and $R^5$ all represent hydrogen.

In a particular embodiment of the invention, $R^6$, $R^7$, $R^8$, $R^9$ and $R^{10}$ independently represent hydrogen, halogen (e.g. chlorine or fluorine), cyano, trifluoromethyl or unsubstituted $C_{1-6}$ alkyl. In a more particular embodiment, $R^6$, $R^7$, $R^8$, $R^9$ and $R^{10}$ independently represent hydrogen, halogen (e.g. chlorine or fluorine), cyano, methyl or trifluoromethyl. In a more particular embodiment, $R^6$, $R^7$, $R^8$, $R^9$ and $R^{10}$ independently represent hydrogen, halogen (e.g. chlorine or fluorine), methyl or trifluoromethyl. In a still more particular embodiment, $R^6$, $R^7$, $R^8$, $R^9$ and $R^{10}$ independently represent hydrogen, chlorine, fluorine, bromine, methyl or trifluoromethyl. In a yet more particular embodiment, $R^6$, $R^7$, $R^8$, $R^9$ and $R^{10}$ independently represent hydrogen, chlorine, fluorine, methyl or trifluoromethyl.

In a particular embodiment, $R^6$ represents hydrogen. In an alternative particular embodiment, $R^6$ represents chlorine, fluorine or methyl; more particularly methyl.

Preferably, $R^7$ represents hydrogen.

In a particular embodiment, $R^6$ and $R^7$ both represent hydrogen. In an alternative particular embodiment, $R^6$ represents chlorine, fluorine or methyl (more particularly methyl), and $R^7$ represents hydrogen.

In a particular embodiment, $R^8$ represents hydrogen or halogen (e.g. chlorine or fluorine). In a more particular embodiment, $R^8$ represents hydrogen, chlorine or fluorine.

In a particular embodiment, $R^9$ represents hydrogen, halogen (e.g. chlorine or fluorine) or trifluoromethyl. In a more particular embodiment, $R^9$ represents hydrogen, chlorine, fluorine or trifluoromethyl.

In a particular embodiment, $R^{10}$ represents halogen (e.g. chlorine or fluorine), $C_{1-6}$ alkyl (e.g. methyl) or trifluoromethyl. In a more particular embodiment, $R^{10}$ represents chlorine, fluorine, methyl or trifluoromethyl. In a still more particular embodiment, $R^{10}$ represents chlorine, fluorine or methyl. Preferably, $R^{10}$ represents chlorine or methyl.

In a more particular embodiment,
$R^6$ and $R^7$ both represent hydrogen,
$R^8$ represents hydrogen, chlorine or fluorine,
$R^9$ represents hydrogen, chlorine, fluorine or trifluoromethyl, and
$R^{10}$ represents chlorine, fluorine, methyl or trifluoromethyl.

In a still more particular embodiment,
$R^6$ and $R^7$ both represent hydrogen,
$R^8$ represents hydrogen, chlorine or fluorine,
$R^9$ represents hydrogen, chlorine, fluorine or trifluoromethyl, and
$R^{10}$ represents chlorine, fluorine or methyl.

Preferably,
$R^6$ and $R^7$ both represent hydrogen,
$R^8$ represents hydrogen, chlorine or fluorine,
$R^9$ represents hydrogen, chlorine, fluorine or trifluoromethyl, and
$R^{10}$ represents chlorine, fluorine or methyl (in particular, chlorine or methyl),
wherein one or both (e.g. one) of $R^8$ and $R^9$ is/are other than hydrogen.

More preferably,
$R^6$ and $R^7$ both represent hydrogen,
$R^8$ represents hydrogen or fluorine,
$R^9$ represents trifluoromethyl, and
$R^{10}$ represents chlorine or methyl.

Preferably,
$R^6$ represents hydrogen, chlorine, fluorine or methyl,

R⁷ represents hydrogen,
R⁸ represents chlorine or fluorine,
R⁹ represents hydrogen, and
R¹⁰ represents chlorine or methyl.

More preferably,
R⁶ represents hydrogen, chlorine, fluorine or methyl,
R⁷ represents hydrogen,
R⁸ represents chlorine,
R⁹ represents hydrogen, and
R¹⁰ represents chlorine or methyl.

In a particularly preferred embodiment, $R^6$, $R^7$ and $R^8$ each represent hydrogen, $R^9$ represents trifluoromethyl, and $R^{10}$ represents chlorine.

In a particularly preferred embodiment, $R^6$, $R^7$ and $R^9$ each represent hydrogen and $R^8$ and $R^{10}$ both represent chlorine.

In a particularly preferred embodiment, $R^6$ and $R^7$ both represent hydrogen, $R^8$ and $R^9$ both represent fluorine, and $R^{10}$ represents chlorine.

In a particularly preferred embodiment, $R^6$, $R^7$ and $R^8$ each represent hydrogen, $R^9$ represents trifluoromethyl, and $R^{10}$ represents methyl.

In a particularly preferred embodiment, $R^6$ and $R^7$ both represent hydrogen, $R^8$ represents fluorine, $R^9$ represents trifluoromethyl, and $R^{10}$ represents chlorine.

In a particularly preferred embodiment, $R^6$ is methyl, $R^7$ and $R^9$ both represent hydrogen, and $R^8$ and $R^{10}$ both represent chlorine.

In a particularly preferred embodiment, $R^6$, $R^8$ and $R^{10}$ each represent chlorine, and $R^7$ and $R^9$ both represent hydrogen.

In a preferred embodiment, $R^6$, $R^7$ and $R^8$ each represent hydrogen, $R^9$ represents trifluoromethyl, and $R^{10}$ represents fluorine.

In a preferred embodiment, $R^6$, $R^7$ and $R^9$ each represent hydrogen, $R^8$ represents fluorine, and $R^{10}$ represents chlorine.

In a preferred embodiment, $R^6$, $R^7$ and $R^9$ each represent hydrogen, $R^8$ represents chlorine, and $R^{10}$ represents methyl.

In a preferred embodiment, $R^6$, $R^7$ and $R^8$ each represent hydrogen, $R^9$ represents chlorine, and $R^{10}$ represents methyl.

In a preferred embodiment, $R^6$ and $R^7$ both represent hydrogen, $R^8$ represents fluorine, and $R^9$ and $R^{10}$ both represent chlorine.

In a preferred embodiment, $R^6$, $R^7$ and $R^8$ each represent hydrogen and $R^9$ and $R^{10}$ both represent chlorine.

In a preferred embodiment, $R^6$ is fluorine, $R^7$ and $R^9$ both represent hydrogen, and $R^8$ and $R^{10}$ both represent chlorine.

In all embodiments of the invention herein described, when $R^6$ and $R^{10}$ independently represent hydrogen or fluorine, at least one of $R^7$, $R^8$ and $R^9$ is a halogen atom, or only one of $R^7$, $R^8$ and $R^9$ is a $CF_3$ group.

In a particular embodiment of the invention herein described, when $R^6$ and $R^{10}$ independently represent hydrogen or fluorine, at least one of $R^7$, $R^8$ and $R^9$ is a halogen atom. In a more particular embodiment of the invention herein described, when $R^6$ and $R^{10}$ independently represent hydrogen or fluorine, at least one of $R^7$, $R^8$ and $R^9$ is a halogen atom, and only one of $R^7$, $R^8$ and $R^9$ is a $CF_3$ group.

In a particular embodiment of the invention, there is provided a compound of formula (I), or a pharmaceutically acceptable salt thereof, wherein:
$R^1$ represents unsubstituted $C_{1-6}$ alkyl, $C_{3-6}$ cycloalkyl; or a benzyl optionally substituted with 1, 2 or 3 halogen atoms;
$R^2$ represents hydrogen or methyl;
$R^3$, $R^4$ and $R^5$ all represent hydrogen; and
$R^6$, $R^7$, $R^8$, $R^9$ and $R^{10}$ independently represent hydrogen, chlorine, fluorine, bromine, methyl or trifluoromethyl;
with the proviso that when $R^6$ and $R^{10}$ independently represent hydrogen or fluorine, at least one of $R^7$, $R^8$ and $R^9$ is a halogen atom, or only one of $R^7$, $R^8$ and $R^9$ is a $CF_3$ group.

One particular aspect of the invention provides a compound or salt selected from a compound of examples E1 to E50, as shown and/or named below, or a pharmaceutically acceptable salt thereof.

One particular aspect of the invention provides a compound or salt selected from a compound of examples E51 to E127, as shown and/or named below, or a pharmaceutically acceptable salt thereof.

One preferred aspect of the invention provides a compound selected from Examples E1 to E5, E7, E8, E10 to E13, E15, E18, E19, E21, E23, E25 to E28, E30, E32 to E35, E39, E41, E42, E45, E51, E52, E54, E55, E57 to E61, E64 to E70, E72 to E79, E81, E82, E85, E86, E88, E89, E91 to E97, E99, E100, E102, E104 to E108, E110 to E113, E115 to E120, and E122 to E127, as a compound or a pharmaceutically acceptable salt thereof.

One preferred aspect of the invention provides a compound or a pharmaceutically acceptable salt thereof, which is:
N-{[2-chloro-3-(trifluoromethyl)phenyl]methyl}-1,3-dimethyl-2-oxo-4-imidazolidinecarboxamide (in particular, (4S)—N-{[2-chloro-3-(trifluoromethyl)phenyl]methyl}-1,3-dimethyl-2-oxo-4-imidazolidinecarboxamide),
N-[(2,4-dichlorophenyl)methyl]-1,3-dimethyl-2-oxo-4-imidazolidinecarboxamide,
N-[(2-chloro-3,4-difluorophenyl)methyl]-1,3-dimethyl-2-oxo-4-imidazolidinecarboxamide,
N-{[2-fluoro-3-(trifluoromethyl)phenyl]methyl}-1,3-dimethyl-2-oxo-4-imidazolidinecarboxamide,
1,3-dimethyl-2-oxo-N-[(2,3,4-trifluorophenyl)methyl]-4-imidazolidinecarboxamide,
N-[(2-chloro-4-fluorophenyl)methyl]-1,3-dimethyl-2-oxo-4-imidazolidinecarboxamide,
N-{[2-chloro-3-(trifluoromethyl)phenyl]methyl}-3-methyl-2-oxo-4-imidazolidinecarboxamide,
N-{[2-Chloro-3-(trifluoromethyl)phenyl]methyl}-3-methyl-2-oxo-1-(2-pyrimidinyl)-4-imidazolidinecarboxamide,
N-{[2-Chloro-3-(trifluoromethyl)phenyl]methyl}-3-methyl-2-oxo-1-(4-piperidinyl)-4-imidazolidinecarboxamide,
N-{[2-Chloro-3-(trifluoromethyl)phenyl]methyl}-3-methyl-2-oxo-1-(3-pyridinyl)-4-imidazolidinecarboxamide,
N-{[2-Chloro-3-(trifluoromethyl)phenyl]methyl}-3-methyl-1-(6-methyl-3-pyridinyl)-2-oxo-4-imidazolidinecarboxamide,
N-{[2-Chloro-3-(trifluoromethyl)phenyl]methyl}-3-methyl-1-(2-methyl-4-pyridinyl)-2-oxo-4-imidazolidinecarboxamide,
N-[(2,4-Dichlorophenyl)methyl]-3-methyl-1-(2-methyl-3-pyridinyl)-2-oxo-4-imidazolidinecarboxamide (in particular, (4S)—N-[(2,4-dichlorophenyl)methyl]-3-methyl-1-(2-methyl-3-pyridinyl)-2-oxo-4-imidazolidinecarboxamide),
N-{[2-Chloro-3-(trifluoromethyl)phenyl]methyl}-3-methyl-1-(2-methyl-4-pyridinyl)-2-oxo-4-imidazolidinecarboxamide,
N-[(2-Chloro-3,4-difluorophenyl)methyl]-3-methyl-1-(2-methyl-3-pyridinyl)-2-oxo-4-imidazolidinecarboxamide,
N-{[2-Chloro-3-(trifluoromethyl)phenyl]methyl}-3-methyl-2-oxo-1-(2-pyridinyl)-4-imidazolidinecarboxamide,
N-[(2-Chloro-3,4-difluorophenyl)methyl]-3-methyl-1-(3-methyl-2-pyridinyl)-2-oxo-4-imidazolidinecarboxamide,
N-{[2-Chloro-3-(trifluoromethyl)phenyl]methyl}-3-methyl-1-(3-methyl-2-pyridinyl)-2-oxo-4-imidazolidinecarboxamide, N-[(2,4-Dichlorophenyl)methyl]-3-methyl-1-(3-methyl-2-pyridinyl)-2-oxo-4-imidazolidinecarboxamide,
N-[(2-Chloro-3,4-difluorophenyl)methyl]-3-methyl-2-oxo-4-imidazolidinecarboxamide,
N-[(2,4-Dichlorophenyl)methyl]-3-methyl-2-oxo-4-imidazolidinecarboxamide,
N-[(2,4-Dichlorophenyl)methyl]-3-methyl-2-oxo-1-(2-pyrimidinyl)-4-imidazolidinecarboxamide,
N-[(2-Chloro-4-fluorophenyl)methyl]-3-methyl-2-oxo-1-(2-pyrimidinyl)-4-imidazolidinecarboxamide,
N-[(2-Chloro-3,4-difluorophenyl)methyl]-3-methyl-2-oxo-1-(2-pyrimidinyl)-4-imidazolidinecarboxamide,
N-[(3-Chloro-2-methylphenyl)methyl]-3-methyl-2-oxo-1-(2-pyrimidinyl)-4-imidazolidinecarboxamide,
N-[(2-Chloro-3,4-difluorophenyl)methyl]-3-methyl-1-(1-methyl-1H-imidazol-4-yl)-2-oxo-4-imidazolidinecarboxamide,
N-[(2-Chloro-3,4-difluorophenyl)methyl]-3-methyl-1-(1-methyl-1H-pyrazol-5-yl)-2-oxo-4-imidazolidinecarboxamide,
N-{[2-Chloro-3-(trifluoromethyl)phenyl]methyl}-3-methyl-1-[2-(4-morpholinyl)ethyl]-2-oxo-4-imidazolidinecarboxamide, or
N-{[2-Chloro-3-(trifluoromethyl)phenyl]methyl}-3-methyl-2-oxo-1-(5-pyrimidinyl)-4-imidazolidinecarboxamide;
or a pharmaceutically acceptable salt thereof.

One preferred aspect of the invention provides a compound or a pharmaceutically acceptable salt thereof, which is:
N-{[2-Chloro-3-(trifluoromethyl)phenyl]methyl}-3-methyl-2-oxo-1-[4-(trifluoromethyl)-2-pyrimidinyl]-4-imidazolidinecarboxamide,
N-[(2,4-Dichlorophenyl)methyl]-3-methyl-2-oxo-1-[4-(trifluoromethyl)-2-pyrimidinyl]-4-imidazolidinecarboxamide,
N-{[2-Chloro-3-(trifluoromethyl)phenyl]methyl}-1-(2,6-dimethyl-3-pyridinyl)-3-methyl-2-oxo-4-imidazolidinecarboxamide,
N-[(2,4-Dichlorophenyl)methyl]-1-(2,6-dimethyl-3-pyridinyl)-3-methyl-2-oxo-4-imidazolidinecarboxamide,
N-{[2-Chloro-3-(trifluoromethyl)phenyl]methyl}-3-methyl-1-(1-methyl-1H-imidazol-4-yl)-2-oxo-4-imidazolidinecarboxamide,
N-[(2,4-Dichlorophenyl)methyl]-3-methyl-1-(1-methyl-1H-imidazol-4-yl)-2-oxo-4-imidazolidinecarboxamide,
N-{[2-Chloro-3-(trifluoromethyl)phenyl]methyl}-3-methyl-1-(1-methyl-1H-imidazol-2-yl)-2-oxo-4-imidazolidinecarboxamide,
N-[(2,4-Dichlorophenyl)methyl]-3-methyl-1-(1-methyl-1H-imidazol-5-yl)-2-oxo-4-imidazolidinecarboxamide,
N-{[2-Chloro-3-(trifluoromethyl)phenyl]methyl}-3-methyl-1-(1-methyl-1H-imidazol-5-yl)-2-oxo-4-imidazolidinecarboxamide,
N-{[2-Chloro-3-(trifluoromethyl)phenyl]methyl}-3-methyl-2-oxo-1-[6-(trifluoromethyl)-4-pyrimidinyl]-4-imidazolidinecarboxamide,
N-[(2,4-Dichlorophenyl)methyl]-1-(6-fluoro-3-pyridinyl)-3-methyl-2-oxo-4-imidazolidinecarboxamide,
N-{[2-Chloro-3-(trifluoromethyl)phenyl]methyl}-1-(6-fluoro-3-pyridinyl)-3-methyl-2-oxo-4-imidazolidinecarboxamide,
N-[(2,4-Dichlorophenyl)methyl]-1-(2-fluoro-3-pyridinyl)-3-methyl-2-oxo-4-imidazolidinecarboxamide,
N-{[2-Chloro-3-(trifluoromethyl)phenyl]methyl}-1-(2-fluoro-3-pyridinyl)-3-methyl-2-oxo-4-imidazolidinecarboxamide,
N-[(2,4-Dichlorophenyl)methyl]-3-methyl-1-[6-(methyloxy)-3-pyridinyl]-2-oxo-4-imidazolidinecarboxamide,
N-{[2-chloro-3-(trifluoromethyl)phenyl]methyl}-3-methyl-1-[6-(methyloxy)-3-pyridinyl]-2-oxo-4-imidazolidinecarboxamide,
N-[(2,4-Dichlorophenyl)methyl]-1-methyl-2-oxo-3-(2,2,2-trifluoroethyl)-4-imidazolidinecarboxamide,
N-[(2,4-Dichlorophenyl)methyl]-3-ethyl-1-methyl-2-oxo-4-imidazolidinecarboxamide,
N-{[2-Chloro-3-(trifluoromethyl)phenyl]methyl}-3-ethyl-1-methyl-2-oxo-4-imidazolidinecarboxamide,
N-[(2-Chloro-4-fluorophenyl)methyl]-3-ethyl-1-methyl-2-oxo-4-imidazolidinecarboxamide,
N-{[2-Chloro-3-(trifluoromethyl)phenyl]methyl}-3-methyl-2-oxo-1-(2-pyrazinyl)-4-imidazolidinecarboxamide,
1-(2-Chloro-3-pyridinyl)-N-[(2,4-dichlorophenyl)methyl]-3-methyl-2-oxo-4-imidazolidinecarboxamide,
N-[(2-Chloro-3,4-difluorophenyl)methyl]-1-(2-chloro-3-pyridinyl)-3-methyl-2-oxo-4-imidazolidinecarboxamide,
1-(2-Chloro-3-pyridinyl)-N-{[2-chloro-3-(trifluoromethyl)phenyl]methyl}-3-methyl-2-oxo-4-imidazolidinecarboxamide,
3-Methyl-N-{[2-methyl-3-(trifluoromethyl)phenyl]methyl}-2-oxo-4-imidazolidinecarboxamide,
N-[(2,3-Dichlorophenyl)methyl]-3-methyl-2-oxo-4-imidazolidinecarboxamide,
N-[(3-Chloro-2-methylphenyl)methyl]-3-methyl-2-oxo-4-imidazolidinecarboxamide,
N-[(2,4-Dichloro-6-methylphenyl)methyl]-3-methyl-2-oxo-4-imidazolidinecarboxamide,
N-[(2,4-Dichlorophenyl)methyl]-1-(5-fluoro-2-pyrimidinyl)-3-methyl-2-oxo-4-imidazolidinecarboxamide,
N-[(2,4-Dichlorophenyl)methyl]-3-ethyl-2-oxo-4-imidazolidinecarboxamide,
N-{[2-Chloro-3-(trifluoromethyl)phenyl]methyl}-3-ethyl-2-oxo-4-imidazolidinecarboxamide,
N-[(2,4-Dichlorophenyl)methyl]-3-methyl-1-[4-(methyloxy)-2-pyrimidinyl]-2-oxo-4-imidazolidinecarboxamide,
1-(5-Chloro-2-pyrimidinyl)-N-[(2,4-dichlorophenyl)methyl]-3-methyl-2-oxo-4-imidazolidinecarboxamide,
N-[(2,4-Dichlorophenyl)methyl]-3-methyl-1-(6-methyl-3-pyridinyl)-2-oxo-4-imidazolidinecarboxamide,
N-[(2-Chloro-3,4-difluorophenyl)methyl]-3-methyl-1-(6-methyl-3-pyridinyl)-2-oxo-4-imidazolidinecarboxamide,
N-[(2,4-Dichlorophenyl)methyl]-1-(2-fluoro-4-pyridinyl)-3-methyl-2-oxo-4-imidazolidinecarboxamide,
N-[(2-Chloro-3,4-difluorophenyl)methyl]-1-(2-fluoro-4-pyridinyl)-3-methyl-2-oxo-4-imidazolidinecarboxamide,
N-[(3-Chloro-2-methylphenyl)methyl]-1,3-dimethyl-2-oxo-4-imidazolidinecarboxamide,
N-[(2,3-Dichlorophenyl)methyl]-1,3-dimethyl-2-oxo-4-imidazolidinecarboxamide,
N-[(2,3-Dichloro-4-fluorophenyl)methyl]-1,3-dimethyl-2-oxo-4-imidazolidinecarboxamide,
N-{[2-Chloro-4-fluoro-3-(trifluoromethyl)phenyl]methyl}-1,3-dimethyl-2-oxo-4-imidazolidinecarboxamide,
N-[(2,4-Dichloro-6-methylphenyl)methyl]-1,3-dimethyl-2-oxo-4-imidazolidinecarboxamide,
1,3-Dimethyl-N-{[2-methyl-3-(trifluoromethyl)phenyl]methyl}-2-oxo-4-imidazolidinecarboxamide,
N-[(4-Chloro-2-methylphenyl)methyl]-1,3-dimethyl-2-oxo-4-imidazolidinecarboxamide,
N-[(2-Chloro-4-cyanophenyl)methyl]-1,3-dimethyl-2-oxo-4-imidazolidinecarboxamide,
N-[(2,4-Dichlorophenyl)methyl]-3-(2,2-difluoroethyl)-1-methyl-2-oxo-4-imidazolidinecarboxamide,
N-[(2,4-Dichlorophenyl)methyl]-1-(3-fluoro-2-pyridinyl)-3-methyl-2-oxo-4-imidazolidinecarboxamide, N-[(2,4-Dichlorophenyl)methyl]-3-methyl-1-(1-methyl-1H-pyrazol-5-yl)-2-oxo-4-imidazolidinecarboxamide,
1-(2-Cyano-3-pyridinyl)-N-[(2,4-dichlorophenyl)methyl]-3-methyl-2-oxo-4-imidazolidinecarboxamide,
N-[(2,4-Dichlorophenyl)methyl]-1-(2,2-difluoroethyl)-3-methyl-2-oxo-4-imidazolidinecarboxamide,
N-[(2,4-Dichlorophenyl)methyl]-3-methyl-2-oxo-1-(2,2,2-trifluoroethyl)-4-imidazolidinecarboxamide,
N-[(2,4-Dichlorophenyl)methyl]-1-(2-fluoroethyl)-3-methyl-2-oxo-4-imidazolidinecarboxamide,
N-[(2,4-Dichlorophenyl)methyl]-1-ethyl-3-methyl-2-oxo-4-imidazolidinecarboxamide,
N-[(2,4-Dichloro-6-fluorophenyl)methyl]-1,3-dimethyl-2-oxo-4-imidazolidinecarboxamide,
1,3-Dimethyl-2-oxo-N-[(2,4,6-trichlorophenyl)methyl]-4-imidazolidinecarboxamide,
N-[(2,4-Dichloro-6-fluorophenyl)methyl]-3-methyl-2-oxo-4-imidazolidinecarboxamide,
3-Methyl-2-oxo-N-[(2,4,6-trichlorophenyl)methyl]-4-imidazolidinecarboxamide,
N-[(2,4-Dichlorophenyl)methyl]-3-methyl-1-(1-methylethyl)-2-oxo-4-imidazolidinecarboxamide,
1-(Cyclopropylmethyl)-N-[(2,4-dichlorophenyl)methyl]-3-methyl-2-oxo-4-imidazolidinecarboxamide,
1-(Cyclobutylmethyl)-N-[(2,4-dichlorophenyl)methyl]-3-methyl-2-oxo-4-imidazolidinecarboxamide, or
1-Cyclopentyl-N-[(2,4-dichlorophenyl)methyl]-3-methyl-2-oxo-4-imidazolidinecarboxamide;
or a pharmaceutically acceptable salt thereof.

A further particular aspect of the present invention provides a compound of formula (IA) or a pharmaceutically acceptable salt thereof:

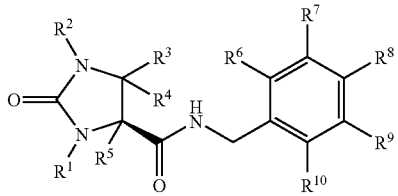

(IA)

wherein:
$R^1$ represents $C_{1-4}$ alkyl or $C_{3-4}$ cycloalkyl, any of which is optionally substituted with 1, 2 or 3 halogen (e.g. fluorine) atoms,
and $R^2$, $R^x$, $R^y$, $R^3$, $R^4$, $R^5$, $R^6$, $R^7$, $R^8$, $R^9$, $R^{10}$, $R^{11}$, $R^{12}$ and n are as defined herein for the compound of formula (I) or salt thereof,
and wherein more than 50% (e.g. more than 70%, in particular more than 90%, such as more than 95%) by molarity of the compound of formula (IA) or the pharmaceutically acceptable salt thereof has the indicated stereochemistry at the ring-carbon atom bonded to $R^5$.

In a particular embodiment, the compound of formula (IA) or the pharmaceutically acceptable salt thereof has an enantiomeric excess of greater than 70% (e.g. more than 80%, in particular more than 90%) with respect to the indicated stereochemistry at the ring-carbon atom bonded to $R^5$.

In a particular embodiment, in a compound of formula (IA) or a salt thereof, $R^1$ represents unsubstituted $C_{1-4}$ alkyl or $C_{3-4}$ cycloalkyl; more particularly methyl, ethyl, n-propyl, i-propyl, cyclopropyl, or cyclobutyl; still more particularly methyl, ethyl, n-propyl or i-propyl.

In a most particular embodiment, in a compound of formula (IA) or a salt thereof, $R^1$ represents methyl or ethyl.

In a particular embodiment, in a compound of formula (IA) or a salt thereof, $R^3$, $R^4$ and $R^5$ all represent hydrogen.

All embodiments, e.g. particular or preferable features or aspects, of the invention (e.g. embodiments of the compound or salt of the invention and/or of pharmaceutical compositions and/or uses thereof) which are disclosed herein in relation to a compound of formula (I) or a salt thereof, are also hereby disclosed and contemplated in relation to a compound of formula (IA) or a salt thereof, to the extent appropriate or possible, with all necessary changes having been made to the wording.

An alternative particular aspect of the invention provides a compound of formula (I) or a pharmaceutically acceptable salt thereof, as disclosed herein, wherein the compound or salt is substantially racemic (e.g. racemic) at the ring-carbon atom bonded to $R^5$.

Antagonists of P2X7 may be useful in preventing, treating, or ameliorating a variety of pain states (e.g. neuropathic pain, chronic inflammatory pain, and visceral pain), inflammation and neurodegeneration, in particular Alzheimer's disease. P2X7 antagonists may also constitute useful therapeutic agents in the management of rheumatoid arthritis and inflammatory bowel disease.

Compounds of the present invention which modulate P2X7 receptor function and are capable of antagonizing the effects of ATP at the P2X7 receptor ("P2X7 receptor antagonists") may be competitive antagonists, inverse agonists, or negative allosteric modulators of P2X7 receptor function.

Certain compounds of formula (I) may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, J. Pharm. Sci., 1977, 66, 1-19. When a compound of the present invention is basic, in one embodiment a pharmaceutically acceptable salt is prepared from a pharmaceutically acceptable acid, such as an inorganic or organic acid, e.g. by admixture of the compound and the acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In a particular embodiment, the pharmaceutically acceptable acid is benzenesulfonic, camphorsulfonic, ethanesulfonic, hydrobromic, hydrochloric, methanesulfonic, nitric, phosphoric, sulfuric, or p-toluenesulfonic acid.

Examples of pharmaceutically acceptable salts include salts formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The compounds of formula (I) or salts thereof may be prepared in crystalline or non-crystalline form, and, if crystalline, may optionally be solvated, e.g. as the hydrate. This invention includes within its scope solvates (e.g. hydrates), such as stoichiometric solvates (e.g. hydrates), of the compounds or salts thereof, as well as compounds or salts thereof containing variable amounts of solvent (e.g. water).

Compounds of formula (I) or salts thereof are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. In examples where the stereochemical composition of the final product has been determined by chiral HPLC (more specifically by methods (A), (B), (C) or (D) as set out in the Examples), the corresponding stereospecific name and structure have generally been assigned to the final product where the enantiomeric excess (e.e.) of said product is greater than 70%. Assignment of absolute stereochemistry is based on the known chirality of the starting material. In examples where the composition of the final product has not been characterised by chiral HPLC, the stereochemistry of the final product has not been indicated. However, the chirality of the main component of the product mixture of the compound or salt will generally be expected to reflect that of the starting material; and/or the enantiomeric excess will generally depend on the synthetic method used and is likely to be similar to that measured for an analogous example (where such an example exists). Thus compounds or salts shown in one chiral form are expected to be able to be prepared in the alternative chiral form using the appropriate starting material. Alternatively, if racemic starting materials are used, it would be expected that a racemic product would be produced and the single enantiomers could be separated by the usual methods. The invention also extends to any tautomeric forms and mixtures thereof.

The subject invention also includes isotopically-labeled compounds, which are identical to those recited in formula (I), or salts thereof, but for the fact that one or more atoms are replaced by an atom having an atomic mass or mass number different from the atomic mass or mass number most commonly found in nature. Examples of isotopes that can be incorporated into compounds or salts of the invention include isotopes of hydrogen, carbon, nitrogen, oxygen, phosphorous, fluorine, iodine, and chlorine, such as 3H, 11C, 14C, 18F, 123I and 125I.

Compounds of the present invention and pharmaceutically acceptable salts of said compounds that contain the aforementioned isotopes and/or other isotopes of other atoms are within the scope of the present invention. Isotopically-labeled compounds or salts of the present invention, for example those into which radioactive isotopes such as 3H, 14C are incorporated, are potentially useful in drug and/or substrate tissue distribution assays. Tritiated, i.e., 3H, and carbon-14, i.e., 14C, isotopes are for example optionally chosen for their ease of preparation and detectability. 11C and 8F isotopes are generally useful in PET (positron emission tomography), and 125I isotopes are generally useful in SPECT (single photon emission computerized tomography). PET and SPECT are useful in brain imaging. Further, substitution with heavier isotopes such as deuterium, i.e., 2H, can sometimes afford certain effects resulting from greater metabolic stability, for example increased in vivo half-life or reduced dosage requirements and, hence, may be chosen in some circumstances. Isotopically labeled compounds of formula (I) or salts thereof of this invention are in one embodiment and in some cases prepared by carrying out the procedures disclosed in the Schemes and/or in the Examples below, by substituting a readily available isotopically labeled reagent for a non-isotopically labeled reagent.

A further particular aspect of the invention provides a compound of formula (I) or a pharmaceutically acceptable salt thereof which is not a radioactive isotopically labeled compound or salt. In a particular embodiment, the compound or salt is not an isotopically labeled compound or salt.

Preparation of Compounds

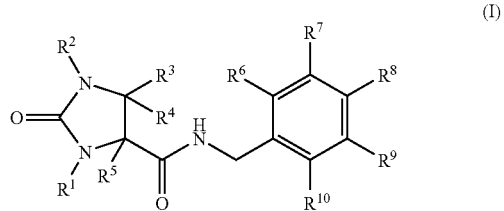

Compounds of formula (I), wherein the variables are as defined above, and salts and solvates thereof may be prepared by the methodology described hereinafter, constituting a further aspect of this invention.

According to a further aspect of the invention, there is provided a process for preparing a compound of formula (I) or a pharmaceutically acceptable salt thereof which comprises:

(a) Coupling of a carboxylic acid of formula (2) (or an activated derivative thereof) with an amine of formula (3) (see Scheme 1), wherein $R^1$, $R^2$, $R^3$, $R^4$, $R^5$, $R^6$, $R^7$, $R^8$, $R^9$, and $R^{10}$ are as defined above. Compounds (2) and (3) are optionally protected.

(b) Deprotecting a compound of formula (I) which is protected. Examples of protecting groups and the means for their removal can be found in T. W. Greene and P. G. M. Wuts 'Protective Groups in Organic Synthesis' (J. Wiley and Sons, 3$^{rd}$ Ed. 1999).

(c) Interconversion of compounds of formula (I) to other compounds of formula (I). Examples of conventional interconversion procedures include epimerisation, oxidation, reduction, alkylation, aromatic substitution, nucleophilic substitution, amide coupling and ester hydrolysis. One example of interconversion is interconversion of a compound of formula (I) wherein $R^2$ represents hydrogen to a compound of formula (I) wherein $R^2$ represents a group other than hydrogen as defined herein.

Scheme 1.

The coupling of an acid of formula (2) and an amine of formula (3) typically comprises the use of activating agents, such as N-(3-dimethylaminopropyl)-N'-ethylcarbodiimide hydrochloride or polymer-supported carbodiimide, 1-hydroxybenzotriazole (HOBT) or 1-Hydroxy-7-azabenzotriazole (HOAt), and optionally a suitable base such as a tertiary alkylamine (e.g. diisopropylethylamine, N-ethyl morpholine, triethylamine) or pyridine, in a suitable solvent such as DMF and/or dichloromethane and at a suitable temperature e.g. between 0° C. and room temperature. Alternatively the coupling of (2) and (3) may be accomplished by treatment with O-(7-Azabenzotriazol-1-yl)-N,N,N',N'-tetramethyluronium hexafluorophosphate and a suitable tertiary alkylamine such as diisopropylethylamine in a suitable solvent such as dimethylformamide at a suitable temperature such as room temperature. Alternatively, the compound of formula (2) may be employed as an activated derivative (e.g. acid chloride, mixed anhydride, active ester (e.g. O-acyl-isourea)), and under such circumstances process (a) typically comprises treatment of said activated derivative with an amine (Ogliaruso, M. A.; Wolfe, J. F. in *The Chemistry of Functional Groups* (Ed. Patai, S.) *Suppl. B: The Chemistry of Acid Derivatives, Pt.* 1 (John Wiley and Sons, 1979), pp 442-8; Beckwith, A. L. J. in *The Chemistry of Functional Groups* (Ed. Patai, S.) *Suppl.B: The Chemistry of Amides* (Ed. Zabricky, J.) (John Wiley and Sons, 1970), pp 73 ff).

Representative methods for the preparation of compounds of formula (2) are shown in Schemes 2 and 3 below:

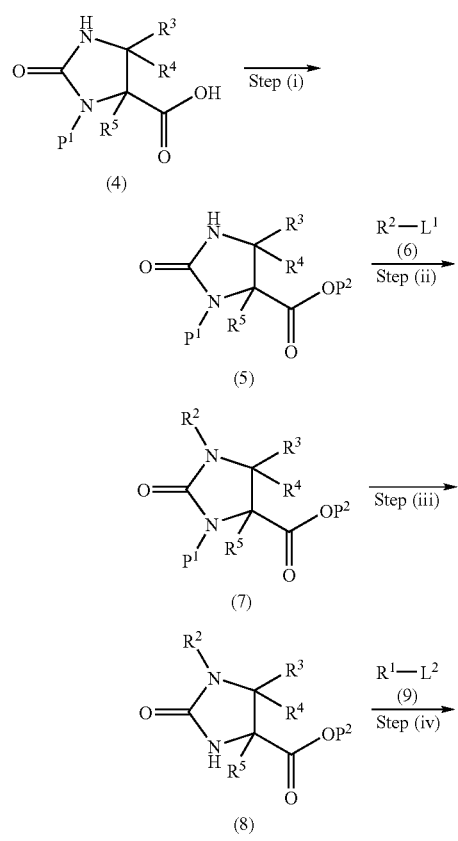

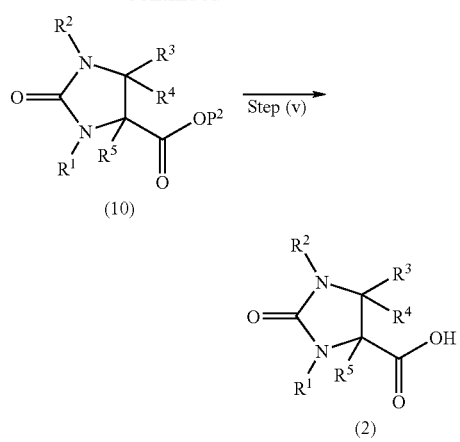

Wherein $R^1$, $R^2$, $R^3$, $R^4$ and $R^5$ areas defined above. $P^1$ represents a suitable amino protecting group such as benzyloxy carbonyl and $P^2$ represents a suitable carboxylate protecting group such as $C_{1-6}$ alkyl, e.g. t-butyl or methyl. $L^1$ and $L^2$ represent suitable leaving groups such as halogen (e.g. bromine, iodine).

Step (i) typically comprises standard protection of the carboxylic acid (4) as the corresponding carboxylic ester for example by treatment with thionyl chloride in a suitable solvent such as methanol at a suitable temperature such as between 0° C. and room temperature.

Step (ii) typically comprises treatment of compound (5) with a suitable base such as potassium carbonate and an alkylating agent (6) such as an alkyl halide (e.g. methyl iodide) at a suitable temperature, such as between room temperature and 80° C., in a suitable solvent, such as dimethoxyethane, to afford compound (7).

Step (iii) comprises deprotection of (7) using standard procedures such as treatment with hydrogen and 5-10% palladium on charcoal in a suitable solvent such as ethyl acetate and at a suitable temperature such as room temperature.

Step (iv) typically comprises treatment of compound (8) with a suitable base such as sodium hydride and an alkylating agent (9) such as an alkyl halide (e.g. methyl iodide) at a suitable temperature, such as between −10° C. and room temperature, in a suitable solvent, such as dimethylformamide or tetrahydrofuran.

Deprotection step (v) typically comprises a standard procedure for conversion of a carboxylic ester (10) to an acid (2), such as use of an appropriate hydroxide salt (e.g. lithium hydroxide) in an appropriate solvent such as a mixture of tetrahydrofuran and water at a suitable temperature such as between 0° C. and room temperature.

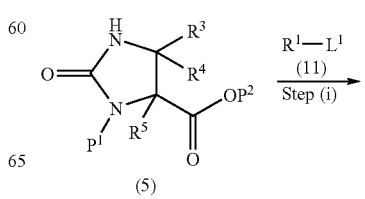

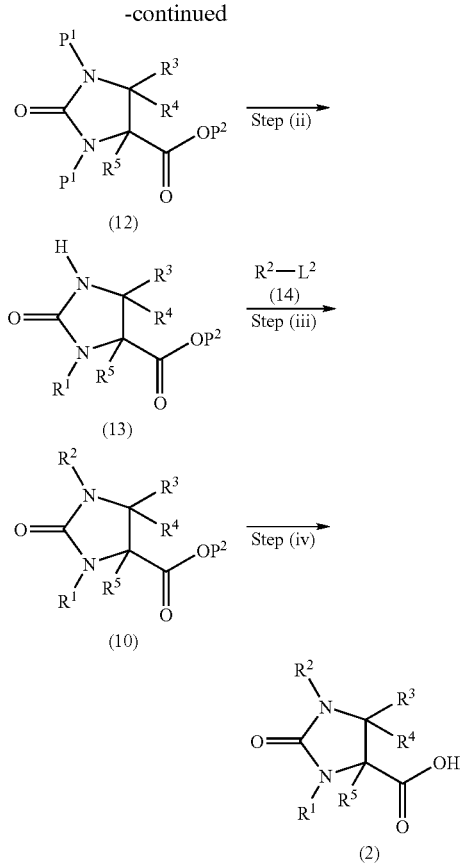

Wherein $R^1$, $R^2$, $R^3$, $R^4$ and $R^5$ areas defined above. $P^1$ represents a suitable amino protecting group such as benzyloxy carbonyl and $P^2$ represents a suitable carboxylate protecting group such as $C_{1-6}$ alkyl, e.g. t-butyl or methyl. $L^1$ and $L^2$ represent suitable leaving groups such as halogen (e.g. bromine, iodine or chlorine).

Analogous methods to those described in Scheme 3 and below have been reported previously in S. Saijo et al., *Chem. Pharm. Bull.*, 1980, 28(5), 1459-1467 (e.g. see pp. 1459-60 and 1463-1464, incorporated herein by reference), for preparation of certain examples of compounds (12), (13) and (10) from Scheme 3 herein, wherein $R^1$ and $R^2$ represent methyl, $P^1$ represents benzyloxycarbonyl and $P^2$ represents methyl.

Step (i) typically comprises treatment of (5) with a suitable base such as sodium hydride and a suitable alkylating agent (11) such as methyl iodide in a suitable solvent such as dimethylformamide and at a suitable temperature such as between 0° C. and room temperature.

Step (ii) typically comprises deprotection of (12) using standard procedures such as treatment with hydrogen and 10% palladium on charcoal (in the case where $P^1$=benzyloxy carbonyl) in a suitable solvent such as methanol and at a suitable temperature such as room temperature.

When the leaving group $L^2$ is attached to an sp$^3$ hybridised carbon, for example, $R^2$-$L^2$ is an alkyl halide, step (iii) typically comprises treatment of (13) with a suitable base such as sodium hydride and a suitable alkylating agent (14) such as methyl iodide in a suitable solvent such as dimethylformamide and at a suitable temperature such as between 0° C. and room temperature. Alternatively, where $R^2$=H step (iii) can be omitted.

When the leaving group $L^2$ is attached to an sp2 hybridised carbon, for example, $R^2$-$L^2$ is an aryl or heteroaryl halide, step (iii) typically comprises the use of a palladium (0) complex such as tris(dibenzylideneacetone)dipalladium(0) in the presence of a base such as cesium carbonate, a ligand such as Xantphos™, in an appropriate solvent such as 1,4-dioxane, at an appropriate temperature such as reflux. Alternatively, step (iii) typically comprises the use of a copper (I) salt, such as copper (I) iodide, in the presence of a base such as potassium phosphate, a ligand such as trans-N,N-dimethylcyclohexane-1,2-diamine, in an appropriate solvent such as 1,4-dioxane, at an appropriate temperature such as reflux.

When the leaving group $L^2$ is attached to an activated sp2 hybridised carbon, for example, $R^2$-$L^2$ is a 2-bromopyrimidine, step (iii) typically comprises the use of a suitable base, such as lithium hexamethyldisilazide, in an appropriate solvent such as tetrahydrofuran, at an appropriate temperature.

Deprotection step (iv) typically comprises a standard procedure for conversion of a carboxylic ester (10) to an acid (2), such as use of an appropriate hydroxide salt (e.g. lithium hydroxide) in an appropriate solvent such as a mixture of tetrahydrofuran and water at a suitable temperature such as between 0° C. and room temperature.

When $P^2$ is a tertiary butyl group, deprotection step (iv) typically comprises reaction of a compound of formula (10) with an acid, for example trifluoroacetic acid in a appropriate solvent such as dichloromethane at an appropriate temperature such as room temperature.

Compounds of the general formulae (3), (4), (6), (9), (11) and (14) are typically either available from commercial sources or can be prepared by a person skilled in the art using methods described in the chemical literature (or using analogous methods).

Where relevant, pharmaceutically acceptable salts may for example be prepared conventionally by reaction with the appropriate acid or acid derivative.

Clinical Indications

It is believed that, as compounds or pharmaceutically acceptable salts of the present invention modulate P2X7 receptor function and are capable of antagonizing the effects of ATP at the P2X7 receptor (P2X7 receptor antagonists), they may be useful in the treatment of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

Chronic articular pain conditions include rheumatoid arthritis, osteoarthritis, rheumatoid spondylitis, gouty arthritis and juvenile arthritis.

Pain associated with functional bowel disorders includes non-ulcer dyspepsia, non-cardiac chest pain and irritable bowel syndrome.

Neuropathic pain syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions which could potentially be treated by compounds or pharmaceutically acceptable salts of the present invention include fever, inflammation, immunological diseases, abnormal platelet function diseases (e.g. occlusive vascular diseases), impotence or erectile dysfunction; bone disease characterised by abnormal bone metabolism or resorbtion; hemodynamic side effects of non-steroidal anti-inflammatory drugs (NSAID's) and cyclooxygenase-2 (COX-2) inhibitors, cardiovascular diseases; neurodegenerative diseases and/or neurodegeneration, neurodegeneration following trauma, tinnitus, dependence on a dependence-inducing agent such as opiods (e.g. morphine), CNS depressants (e.g. ethanol), psychostimulants (e.g. cocaine) and nicotine; complications of Type I diabetes, kidney dysfunction, liver dysfunction (e.g. hepatitis, cirrhosis), gastrointestinal dysfunction (e.g. diarrhoea), colon cancer, overactive bladder and urge incontinence. Depression and alcoholism could potentially also be treated by compounds or pharmaceutically acceptable salts of the present invention.

Inflammatory conditions include skin conditions (e.g. sunburn, burns, eczema, dermatitis, allergic dermatitis, psoriasis), meningitis, ophthalmic diseases such as glaucoma, retinitis, retinopathies, uveitis and of acute injury to the eye tissue (e.g. conjunctivitis), inflammatory lung disorders (e.g. asthma, bronchitis, emphysema, allergic rhinitis, respiratory distress syndrome, pigeon fancier's disease, farmer's lung, chronic obstructive pulmonary disease (COPD), airways hyperresponsiveness); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation and other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, gingivitis, myocardial ischemia, pyrexia, systemic lupus erythematosus, polymyositis, tendinitis, bursitis, and Sjogren's syndrome.

Immunological diseases include autoimmune diseases, immunological deficiency diseases or organ transplantation.

Bone diseases characterised by abnormal bone metabolism or resorbtion include osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis.

Cardiovascular diseases include hypertension or myocardiac ischemia; atherosclerosis; functional or organic venous insufficiency; varicose therapy; haemorrhoids; and shock states associated with a marked drop in arterial pressure (e.g. septic shock).

Neurodegenerative diseases include dementia, particularly degenerative dementia (including senile dementia, dementia with Lewy bodies, Alzheimer's disease, Pick's disease, Huntingdon's chorea, Parkinson's disease and Creutzfeldt-Jakob disease, Amyotrophic Lateral Sclerosis (ALS) and motor neuron disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment associated with ageing, particularly Age Associated Memory Impairment.

The compounds of formula (I) or pharmaceutically acceptable salts may also be useful for neuroprotection and in the treatment of neurodegeneration following trauma such as stroke, cardiac arrest, pulmonary bypass, traumatic brain injury, spinal cord injury or the like.

The compounds or pharmaceutically acceptable salts of the present invention may also be useful in the treatment of malignant cell growth and/or metastasis, and myoblastic leukaemia.

Complications of Type 1 diabetes include diabetic microangiopathy, diabetic retinopathy, diabetic nephropathy, macular degeneration, glaucoma, nephrotic syndrome, aplastic anaemia, uveitis, Kawasaki disease and sarcoidosis.

Kidney dysfunction includes nephritis, glomerulonephritis, particularly mesangial proliferative glomerulonephritis and nephritic syndrome.

It is to be understood that reference to treatment includes both treatment of established symptoms and prophylactic treatment, unless explicitly stated otherwise.

According to a further aspect of the invention, we therefore provide a compound of formula (I) or a pharmaceutically acceptable salt thereof for use in therapy and/or for use in human or veterinary medicine.

According to another aspect of the invention, we provide a compound of formula (I) or a pharmaceutically acceptable salt thereof for use in the treatment or prevention (e.g. treatment) of a condition which is mediated by P2X7 receptors, for example a condition or disease disclosed herein (in particular pain, inflammation or a neurodegenerative disease, more particularly pain such as inflammatory pain, neuropathic pain or visceral pain), e.g. in a mammal such as a human or rodent e.g. human or rat e.g. human.

According to a further aspect of the invention, we provide a method of treating a human or animal (e.g. rodent e.g. rat) subject, for example a human subject, suffering from a condition which is mediated by P2X7 receptors, for example a condition or disease disclosed herein (in particular pain, inflammation or a neurodegenerative disease, more particularly pain such as inflammatory pain, neuropathic pain or visceral pain), which comprises administering to said subject an effective amount of a compound of formula (I) or a pharmaceutically acceptable salt thereof.

According to a further aspect of the invention we provide a method of treating a human or animal (e.g. rodent e.g. rat) subject, for example a human subject, suffering from pain, inflammation, an immunological disease, a bone disease or a neurodegenerative disease (in particular pain, inflammation or a neurodegenerative disease, more particularly pain such as inflammatory pain, neuropathic pain or visceral pain), which method comprises administering to said subject an effective amount of a compound of formula (I) or a pharmaceutically acceptable salt thereof.

According to a yet further aspect of the invention we provide a method of treating a human or animal (e.g. rodent e.g. rat) subject, for example a human subject, suffering from inflammatory pain, neuropathic pain or visceral pain which method comprises administering to said subject an effective amount of a compound of formula (I) or a pharmaceutically acceptable salt thereof.

According to a further aspect of the invention we provide a method of treating a subject, for example a human subject, suffering from Alzheimer's disease which method comprises administering to said subject an effective amount of a compound of formula (I) or a pharmaceutically acceptable salt thereof.

According to another aspect of the invention, we provide the use of a compound of formula (I) or a pharmaceutically acceptable salt thereof for the manufacture of a medicament for the treatment or prevention (e.g. treatment) of a condition which is mediated by the action of P2X7 receptors, for example a condition or disease disclosed herein (in particular pain, inflammation or a neurodegenerative disease, more particularly pain such as inflammatory pain, neuropathic pain or visceral pain), e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prevention (e.g. treatment) of pain, inflammation, an immunological disease, a bone disease or a neurodegenerative disease (in particular pain, inflammation or a neurodegenerative disease, more particularly pain such as inflammatory pain, neuropathic pain or visceral pain), e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prevention (e.g. treatment) of inflammatory pain, neuropathic pain or visceral pain, e.g. in a mammal such as a human or rodent e.g. human or rat e.g. human.

In one aspect of the invention we provide the use of a compound of formula (I) or a pharmaceutically acceptable salt thereof for the manufacture of a medicament for the treatment or prevention (e.g. treatment) of Alzheimer's disease, e.g. in a mammal such as a human or rodent e.g. human or rat e.g. human.

In order to use a compound of formula (I) or a pharmaceutically acceptable salt thereof for the treatment of humans and other mammals it is normally formulated in accordance with standard pharmaceutical practice as a pharmaceutical composition. Therefore in another aspect of the invention there is provided a pharmaceutical composition comprising a compound of formula (I), or a pharmaceutically acceptable salt thereof, adapted for use in human or veterinary medicine.

In order to use a compound of formula (I) a pharmaceutically acceptable salt thereof in therapy, it will normally be formulated into a pharmaceutical composition in accordance with standard pharmaceutical practice.

The present invention also provides a pharmaceutical composition, which comprises a compound of formula (I) or a pharmaceutically acceptable salt thereof, and optionally a pharmaceutically acceptable carrier or excipient.

The pharmaceutical composition may be for use in a method of treatment or in a use or in a treatment or prevention, as described herein.

A pharmaceutical composition of the invention, which may be prepared by admixture, for example at ambient temperature and atmospheric pressure, is usually adapted for oral, parenteral or rectal administration. As such, the pharmaceutical composition may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain excipients, such as binding agents, fillers, tabletting lubricants, disintegrants and/or acceptable wetting agents. The tablets may be coated, e.g. according to methods known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are for example prepared utilising a compound of the invention or pharmaceutically acceptable salt thereof and a sterile vehicle. In one particular embodiment, the compound or salt, depending on the vehicle and concentration used, is either suspended or dissolved in the vehicle. In preparing solutions, the compound or salt can e.g. be dissolved for injection and filter sterilised before filling into a suitable vial or ampoule and sealing. In one embodiment, adjuvant(s) such as a local anaesthetic, a preservative and/or a buffering agent are dissolved in the vehicle. To enhance the stability, the composition can for example be frozen after filling into the vial and the water removed under vacuum. Parenteral suspensions are typically prepared in substantially the same manner, except that the compound or salt is typically suspended in the vehicle instead of being dissolved, and sterilization is not usually readily accomplished by filtration. The compound or salt can be sterilised e.g. by exposure to ethylene oxide before suspension in a sterile vehicle. In a particular embodiment, a surfactant or wetting agent is included in the composition to facilitate uniform distribution of the compound or salt of the invention.

In one embodiment, the composition contains from 0.1% to 99% by weight, in particular from 10 to 60% by weight, of the active material (the compound or pharmaceutically acceptable salt of the invention), e.g. depending on the method of administration.

The dose of the compound or pharmaceutically acceptable salt thereof used in the treatment or prevention (e.g. treatment) of the aforementioned disorders/diseases/conditions may vary in the usual way with the seriousness of the disorders, the weight of the sufferer, and/or other similar factors. However, as a general guide, in one embodiment a suitable unit dose of 0.05 to 1000 mg, for example 0.05 to 200 mg, such as 20 to 40 mg, of the compound or pharmaceutically acceptable salt of the invention (measured as the compound), may be used. In one embodiment, such a unit dose is for administration once a day e.g. to a mammal such as a human; alternatively such a unit dose may be for administration more than once (e.g. twice) a day e.g. to a mammal such as a human. Such therapy may extend for a number of weeks or months.

Combinations

Compounds of formula (I) or salts thereof may be used in combination with other therapeutic agents, for example medicaments claimed to be useful in the treatment of the above mentioned disorders.

Suitable examples of other such therapeutic agents may include a β2-agonist (also known as β2 adrenoceptor agonists; e.g. formoterol) and/or a corticosteroid (e.g. budesonide, fluticasone (e.g. as propionate or furoate esters), mometasone (e.g. as furoate), beclomethasone (e.g. as 17-propionate or 17,21-dipropionate esters), ciclesonide, triamcinolone (e.g. as acetonide), flunisolide, rofleponide and butixocort (e.g. as propionate ester), for the treatment of respiratory disorders (such as asthma and chronic obstructive pulmonary disease (COPD)) as described in WO 2007/008155 and WO 2007/008157.

A further therapeutic agent may include a 3-hydroxy-3-methylglutaryl coenzyme A (HMG CoA) reductase inhibitor (e.g. atorvastatin, fluvastatin, lovastatin, pravastatin, rosuvastatin, and simvastatin) for the treatment of cardiovascular disorders (such as atherosclerosis) as described in WO 2006/083214.

A further therapeutic agent may include a non-steroid anti-inflammatory drug (NSAID; e.g. ibuprofen, naproxen, aspirin, celecoxib, diclofenac, etodolac, fenoprofen, indomethacin, ketoprofen, ketoralac, oxaprozin, nabumetone, sulindac, tolmetin, rofecoxib, valdecoxib, lumaricoxib, meloxicam, etoricoxiband and parecoxib) for the treatment of an inflammatory disease or disorder (such as rheumatoid arthritis or osteoarthritis) as described in WO 2005/025571.

A further therapeutic agent may include a tumour necrosis factor α (TNFα) inhibitor (e.g. Etanercept or an anti-TNFα antibody such as Infliximab and Adalimumab) for the treatment of an inflammatory disease or disorder (such as rheumatoid arthritis or osteoarthritis) as described in WO 2004/105798.

A further therapeutic agent may include 2-hydroxy-5-[[4-[(2-pyridinylamino) sulfonyl]phenyl]azo]benzoic acid (sulfasalazine) for the treatment of an inflammatory disease or disorder (such as rheumatoid arthritis) as described in WO 2004/105797.

A further therapeutic agent may include N-[4-[[(2,4-diamino-6-pteridinyl)methyl]methylamino]benzoyl]-L-glutamic acid (methotrexate) for the treatment of an inflammatory disease or disorder (such as rheumatoid arthritis) as described in WO 2004/105796.

A further therapeutic agent may include an inhibitor of pro TNFα convertase enzyme (TACE) for the treatment of an inflammatory disease or disorder (such as rheumatoid arthritis) as described in WO 2004/073704.

A further therapeutic agent may include:
a) sulfasalazine;
b) a statin, such as atorvastatin, lovastatin, pravastatin, simvastatin, fluvastatin, cerivastatin, crilvastatin, dalvastatin, rosuvastatin, tenivastatin, fluindostatin, velostatin, dalvastatin, nisvastatin, bervastatin, pitavastatin, rivastatin, glenvastatin, eptastatin, tenivastatin, flurastatin, rosuvastatin or itavastatin;
c) a glucocorticoid agent, such as dexamethasone, methylprednisolone, prednisolone, prednisone and hydrocortisone;
d) an inhibitor of p38 kinase;
e) an anti-IL-6-receptor antibody;
f) anakinra;
g) an anti-IL-1 monoclonal antibody;
h) an inhibitor of JAK3 protein tyrosine kinase;
i) an anti-macrophage colony stimulation factor (M-CSF) monoclonal antibody; or
j) an anti-CD20 monoclonal antibody, such as rituximab, PRO70769, HuMax-CD20 (Genmab AJS), AME-133 (Applied Molecular Evolution), or hA20 (Immunomedics, Inc.) for the treatment of an IL-1 mediated disease (such as rheumatoid arthritis) as described in WO 2006/003517.

When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone.

The following Descriptions and Examples illustrate the preparation of compounds or salts of the invention but are not intended to be limiting.

EXAMPLES

The general methods (a)-(c), along with the synthetic methods outlined in Schemes 1, 2 and 3 above, for the preparation of compounds or salts of the present invention are further illustrated by the following examples.

Some abbreviations used herein:
DCM—dichloromethane
DMF—N,N-dimethylformamide
TFA—trifluoroacetic acid
Xantphos™ refers to 4,5-bis(diphenylphosphino)-9,9-dimethylxanthene, which is commercially available e.g. from Aldrich; CAS no. 161265-03-8.

(4S)-2-Oxo-3-{[(phenylmethyl)oxy]carbonyl}-4-imidazolidinecarboxylic acid, which is used herein as the original starting material in many of the examples e.g. Examples 1 and 13, is commercially available, e.g. from Sigma-Aldrich, UK or US (catalogue no. 392308); and has CAS number 59760-01-9. This compound and its preparation is also described in M. P. Doyle and J. T. Colyer, *Tetrahedron: Asymmetry*, 2003, 14(22), 3601-3604 (see e.g. Experimental 4.2, and Results and discussion section first paragraph and Equation (1)), incorporated herein by reference.

Example 1

N-{[2-chloro-3-(trifluoromethyl)phenyl]methyl}-1,3-dimethyl-2-oxo-4-imidazolidinecarboxamide (E1) (in a form obtainable or prepared from (4S)-2-oxo-3-{[(phenylmethyl)oxy]carbonyl}-4-imidazolidinecarboxylic acid)

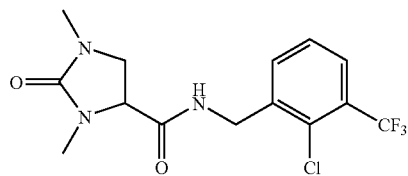

Crude 1,3-Dimethyl-2-oxo-4-imidazolidinecarboxylic acid (0.098 g, ~0.619 mmol, prepared as described below) was dissolved in dimethylformamide (5 ml) and treated with 1-hydroxybenzotriazole (0.092 g, 0.681 mmol), N-(3-dimethylaminopropyl)-N'-ethylcarbodiimide hydrochloride (0.131 g, 0.681 mmol), [(2-chloro-3-trifluoromethylphenyl) methyl]amine (0.156 g, 0.743 mmol) and N-ethylmorpholine (0.166 ml, 1.30 mmol). The mixture was stirred at room temperature (22° C.) for 18 hours then reduced in vacuo to give a residue which was purified by mass-directed automated HPLC to give a colourless gum. Trituration of the gum with diethyl ether (1 ml) and drying gave a pale yellow gum which was further purified by flash silica-gel column chromatography (eluting with a gradient of 0-100% ethyl acetate in dichloromethane (in 10% steps)) to give partially pure (~80%) product as a white solid (0.042 g). A final purification step, again using mass-directed automated HPLC, gave N-{[2-chloro-3-(trifluoromethyl)phenyl]methyl}-1,3-dimethyl-2-oxo-4-imidazolidinecarboxamide as a white solid (0.031 g). LC/MS [M+H]$^+$=350, retention time=2.29 minutes.

Enantiomeric excess=99.1%, as determined by chiral chromatography Method (C), indicative of (4S)—N-{[2-chloro-3-(trifluoromethyl)phenyl]methyl}-1,3-dimethyl-2-oxo-4-imidazolidinecarboxamide, retention time=8.30 minutes The 1,3-dimethyl-2-oxo-4-imidazolidinecarboxylic acid used in the method described above was prepared as follows:
(i) (4S)-2-Oxo-3-{[(phenylmethyl)oxy]carbonyl}-4-imidazolidinecarboxylic acid (10.25 g, 38.8 mmol) was dissolved in anhydrous methanol (100 ml) and cooled to 0° C. under argon. Thionyl chloride (4.25 ml, 58.2 mmol) was then added dropwise to the mixture and then the mixture was allowed to warm to room temperature and stirred overnight. The mixture was reduced in vacuo and the residue was partitioned between dichloromethane (300 ml) and saturated aqueous sodium hydrogen carbonate (100 ml). The aqueous layer was separated and extracted with dichloromethane (300 ml). The organic layers were then combined, passed through a hydrophobic frit and reduced in vacuo to give 5-methyl 1-(phenylmethyl)2-oxo-1,5-imidazolidinedicarboxylate (10.67 g) as a white solid.
(ii) 5-Methyl 1-(phenylmethyl)2-oxo-1,5-imidazolidinedicarboxylate (10.67 g, 38 mmol) and potassium carbonate (10.6 g, 76 mmol) were suspended in dimethoxyethane (150 ml) and treated with methyl iodide (9.46 ml, 152 mmol). The reaction mixture was heated to reflux and stirred under argon for 18 hrs. The mixture was then cooled and evaporated in vacuo and the resulting residue was partitioned between ethyl acetate (750 ml) and brine (200 ml). The organic layer was separated, passed through a hydrophobic frit and reduced in vacuo. The resulting residue was purified by automated flash silica gel column chromatography (Biotage SP4), eluting with a 20-60% gradient of ethyl acetate in hexane, to give 5-methyl 1-(phenylmethyl)3-methyl-2-oxo-1,5-imidazolidinedicarboxylate (5.77 g) as an orange oil.
(iii) A suspension of 5-Methyl 1-(phenylmethyl)3-methyl-2-oxo-1,5-imidazolidinedicarboxylate (5.77 g) and 5% palladium on carbon (5 g) in ethyl acetate (300 ml) was placed under a hydrogen atmosphere and stirred for 24 hrs. The mixture was then filtered and reduced in vacuo to yield methyl 1-methyl 1-2-oxo-4-imidazolidinecarboxylate (2.76 g) as a white solid which was used without further purification.
(iv) A solution of methyl 1-methyl-2-oxo-4-imidazolidinecarboxylate (1.76 g, 11.1 mmol) in anhydrous dimethylformamide (20 ml) was cooled to −10° C. under argon and treated with methyl iodide (2.76 ml, 44.4 mmol). Sodium hydride (60% in oil, 0.422 g, 10.5 mmol) was then added in portions over a period of 20 minutes. The mixture was allowed to warm to room temperature (in the cooling bath) and stirred for 18 hrs. The reaction mixture was then reduced in vacuo and the residue partitioned between ethyl acetate (150 ml) and brine (50 ml). The aqueous layer (containing a fine suspension) was separated and extracted with more ethyl acetate (100 ml). The organic extracts were then combined, passed through a hydrophobic frit, and reduced in vacuo to give an orange oil. This material was purified by flash silica gel column chromatography, eluting with 50% ethyl acetate in hexane and then with a gradient of 50-100% in hexane, to give methyl 1,3-dimethyl-2-oxo-4-imidazolidinecarboxylate (1.123 g) as a colourless oil which was used without further purification.
(v) Methyl 1,3-dimethyl-2-oxo-4-imidazolidinecarboxylate (1.12 g) was dissolved in 10 ml of a 3:2 mixture of tetrahydrofuran and water respectively, then cooled to 0° C. and treated with lithium hydroxide (0.156 g). The reaction was stirred between 0-5° C. for 4 hrs, then acidified with 2N aqueous hydrogen chloride (4 ml) and reduced in vacuo. The residue was dissolved in methanol and loaded onto 2×10 g NH$_2$ solid-phase extraction (SPE) cartridges and eluted with methanol (2 column volumes) and then with a 10% mixture of 2N aqueous hydrogen chloride in methanol (2 column volumes). The latter fractions were combined and evaporated to give crude 1,3-dimethyl-2-oxo-4-imidazolidinecarboxylic acid (0.098 g) as a colourless gum which was used without any additional purification.

Example 2

N-[(2,4-dichlorophenyl)methyl]-1,3-dimethyl-2-oxo-4-imidazolidinecarboxamide (E2) (in a form obtainable or prepared from (4S)-2-oxo-3-{[(phenylmethyl)oxy]carbonyl}-4-imidazolidinecarboxylic acid)

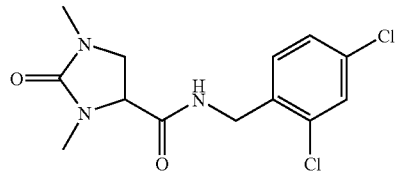

N-[(2,4-dichlorophenyl)methyl]-1,3-dimethyl-2-oxo-4-imidazolidinecarboxamide (E2) was prepared in an analogous manner to that described above for the synthesis of N-{[2-chloro-3-(trifluoromethyl)phenyl]methyl}-1,3-dimethyl-2-oxo-4-imidazolidinecarboxamide (E1) but using [(2,4-dichlorophenyl)methyl]amine in the place of [(2-chloro-3-trifluoromethylphenyl)methyl]amine.

LC/MS [M+H]$^+$=316, retention time=2.19 minutes.

Furthermore the methyl 1,3-dimethyl-2-oxo-4-imidazolidinecarboxylate used in the above procedure (see description of method used to prepare 1,3-dimethyl-2-oxo-4-imidazolidinecarboxylic acid) was prepared in a slightly different manner and is described below:
Methyl 1-methyl-2-oxo-4-imidazolidinecarboxylate (1 g, 6.32 mmol) (prepared as described in step (iii) of Example 1, starting from (4S)-2-oxo-3-{[(phenylmethyl)oxy]carbonyl}-4-imidazolidinecarboxylic acid) was dissolved in anhydrous tetrahydrofuran (10 ml), cooled to −10° C. under argon, and treated with methyl iodide (1.57 ml, 25.3 mmol). Sodium hydride (60% in oil, 0.24 g, 6.0 mmol) was then added in portions over a period of 15 minutes and the mixture was allowed to warm to room temperature and stirred for 18 hrs. The reaction mixture was then reduced in vacuo and the residue partitioned between ethyl acetate (40 ml) and brine (20 ml). The organic layer was separated, passed through a hydrophobic frit, and reduced in vacuo to give a yellow oil. This material was purified by automated flash silica gel column chromatography (Biotage SP4), eluting with 50% ethyl acetate in hexane (5 column volumes) and then with a gradient of 50-80% in hexane (15 column volumes), to give methyl 1,3-dimethyl-2-oxo-4-imidazolidinecarboxylate (0.479 g) as a yellow oil which was used without further purification.

Examples 3-7

In forms obtainable or prepared from (4S)-2-oxo-3-{[(phenylmethyl)oxy]carbonyl}-4-imidazolidinecarboxylic acid)

In a manner analogous to that described for Example 2 above the compounds tabulated below (Table 1) were prepared by substituting the appropriate amine (or salt thereof) for the [(2,4-dichlorophenyl)methyl]amine used in the above procedure. All of the amines used to make the amines shown in Table 1 are available from commercial sources or can be prepared using routes described previously in the chemical literature or analogous methods.

TABLE 1

| Example no. | Chemical name | [M + H]⁺ | Retention time (mins) |
|---|---|---|---|
| E3 | 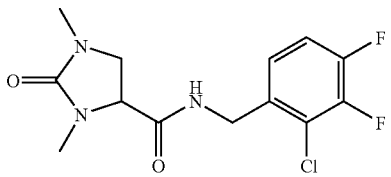 N-[(2-chloro-3,4-difluorophenyl)methyl]-1,3-dimethyl-2-oxo-4-imidazolidinecarboxamide | 318 | 2.06 |
| E4 | 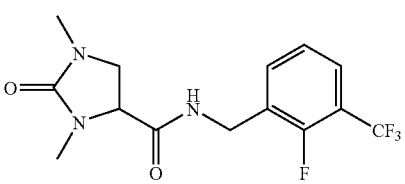 N-{[2-fluoro-3-(trifluoromethyl)phenyl]methyl}-1,3-dimethyl-2-oxo-4-imidazolidinecarboxamide | 334 | 2.18 |
| E5 | 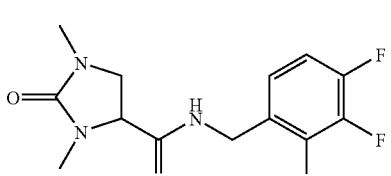 1,3-dimethyl-2-oxo-N-[(2,3,4-trifluorophenyl)methyl]-4-imidazolidinecarboxamide | 302 | 1.93 |
| E6 | 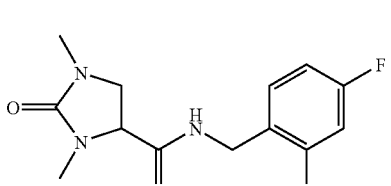 N-{[4-fluoro-2-(trifluoromethyl)phenyl]methyl}-1,3-dimethyl-2-oxo-4-imidazolidinecarboxamide | 334 | 2.16 |

TABLE 1-continued

| Example no. | Chemical name | [M + H]⁺ | Retention time (mins) |
|---|---|---|---|
| E7 | 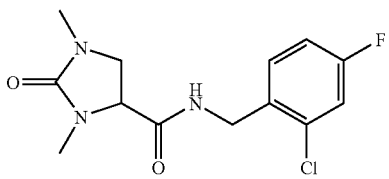<br>N-[(2-chloro-4-fluorophenyl)methyl]-1,3-dimethyl-2-oxo-4-imidazolidinecarboxamide | 300 | 1.97 |

Example 8

N-{[2-chloro-3-(trifluoromethyl)phenyl]methyl}-3-methyl-2-oxo-4-imidazolidinecarboxamide (E8) (e.g. in a form obtainable or prepared from (4S)-2-oxo-3-{[(phenylmethyl)oxy]carbonyl}-4-imidazolidinecarboxylic acid)

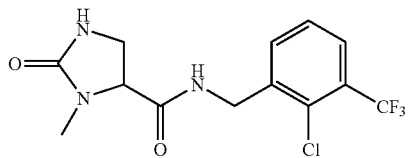

Crude 3-methyl-2-oxo-4-imidazolidinecarboxylic acid (~0.63 mmol, prepared as described below) was dissolved in dimethylformamide (3 ml) and treated with 1-hydroxybenzotriazole (0.094 g, 0.69 mmol), N-(3-dimethylaminopropyl)-N'-ethylcarbodiimide hydrochloride (0.132 g, 0.69 mmol), [(2-chloro-3-trifluoromethylphenyl)methyl]amine (0.145 g, 0.69 mmol) and N-ethylmorpholine (0.169 ml, 1.32 mmol). The mixture was stirred at 22° C. for 20 hours then reduced in vacuo to give a residue which was purified by mass-directed automated HPLC to give N-{[2-chloro-3-(trifluoromethyl)phenyl]methyl}-3-methyl-2-oxo-4-imidazolidinecarboxamide as a white solid (0.105 g). LC/MS [M+H]⁺ =336, retention time=2.18 minutes.

The 3-methyl-2-oxo-4-imidazolidinecarboxylic acid used in the method described above was prepared as follows:
(i) A solution of 5-methyl 1-(phenylmethyl)2-oxo-1,5-imidazolidinedicarboxylate (5 g, 18 mmol) (prepared as described in step (i) of Example 1, starting from (4S)-2-oxo-3-{[(phenylmethyl)oxy]carbonyl}-4-imidazolidinecarboxylic acid) in dimethylformamide (27 ml) was added dropwise to a suspension of sodium hydride (60% in oil, 0.72 g, 18 mmol) in dimethylformamide (45 ml) at 0° C. under an argon atmosphere. The cooling bath was removed and the mixture stirred under argon for 1 hr then treated with methyl iodide (5.6 ml). The mixture was stirred at 22° C. for a further 18 hrs and then reduced in vacuo to give a residue which was partitioned between ethyl acetate (250 ml) and brine (75 ml). The organic layer was separated, using a hydrophobic frit, and then reduced in vacuo to give an orange oil. The oil was purified flash-silica gel column chromatography, eluting with 30% ethyl acetate in hexanes (3 column volumes) and then with a 30-70% gradient of ethyl acetate in hexanes (10 column volumes), to give 4-methyl 1-(phenylmethyl)3-methyl-2-oxo-1,4-imidazolidinedicarboxylate (3.65 g) as a colourless oil.
(ii) 4-Methyl 1-(phenylmethyl)3-methyl-2-oxo-1,4-imidazolidinedicarboxylate (3.65 g, 12.5 mmol) was dissolved in methanol (300 ml) and hydrogenated in the presence of 10% palladium on carbon (0.5 g). The mixture was stirred for 18 hrs at 22° C., then filtered and reduced in vacuo to give methyl 3-methyl-2-oxo-4-imidazolidinecarboxylate (1.90 g) as a white solid which was used in the next step without further purification.
(iii) Methyl 3-methyl-2-oxo-4-imidazolidinecarboxylate (0.150 g, 0.948 mmol) was dissolved in a 3:2 mixture of tetrahydrofuran and water respectively (2.5 ml) and cooled to 0° C. The mixture was then treated with lithium hydroxide (0.068 g, 2.84 mmol) and stirred with ice/water cooling for a further 5 hrs. The mixture was acidified to pH1 by addition of 2N hydrochloric acid (3 ml) and the resulting mixture was then reduced in vacuo to give 3-methyl-2-oxo-4-imidazolidinecarboxylic acid as a white solid (0.260 g) which was used without any further purification.

Example 9

N-[(2-Chloro-3,4-difluorophenyl)methyl]-3-methyl-2-oxo-1-(2-pyridinylmethyl)-4-imidazolidinecarboxamide hydrochloride (E9)

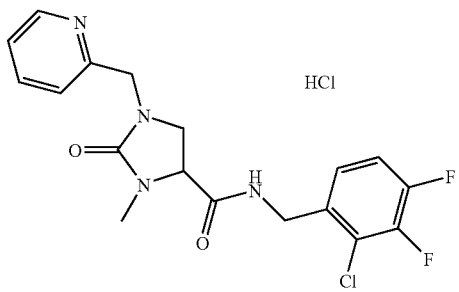

A mixture of crude 3-methyl-2-oxo-1-(2-pyridinylmethyl)-4-imidazolidinecarboxylic acid (~0.7 mmol), 1-hydroxybenzotriazole hydrate (113 mg, 0.84 mmol), 1-ethyl-3-(3-dimethylaminopropyl)carbodiimide hydrochloride (161 mg, 0.84 mmol), and N-ethyl morpholine (0.27 ml, 2.1 mmol) in dichloromethane (20 ml)/N,N-dimethylformamide (2 ml) was stirred at room temperature for 10 minutes. A solution of [(2-chloro-3,4-difluorophenyl)methyl]amine (150 mg, 0.84 mmol) in dichloromethane (5 ml) was added and the reaction stirred at room temperature for 18 hours. The mixture was diluted with dichloromethane and the solution was washed with saturated sodium hydrogen carbonate solution, water and brine, dried and evaporated. The residue was purified by silica gel chromatography eluting with 0-10% methanol in dichloromethane. The residue was triturated with ether/hexanes and the solid was dried. The residue was dissolved in dichloromethane (2 ml), hydrogen chloride (1M in ether, 0.1 ml) was added and the solvent was evaporated. The solid was co-evaporated with ethyl acetate and ether and then triturated with ether. The solid was collected and dried to give N-[(2-chloro-3,4-difluorophenyl)methyl]-3-methyl-2-oxo-1-(2-pyridinylmethyl)-4-imidazolidinecarboxamide hydrochloride (40 mg). LC/MS [M+H]$^+$=395, retention time=1.85 minutes.

The 3-methyl-2-oxo-1-(2-pyridinylmethyl)-4-imidazolidinecarboxylic acid used in the method described above was prepared as follows:

(i) A suspension of sodium hydride (240 mg, 6 mmol, 60% dispersion in oil) in N-methyl-2-pyrrolidinone (6 ml) was stirred at 0° C. under argon. A solution of methyl 3-methyl-2-oxo-4-imidazolidinecarboxylate (474 mg, 3 mmol) (prepared as described in step (ii) of Example 8) in N-methyl-2-pyrrolidinone (3 ml) was added dropwise over 10 minutes. The reaction was stirred at 0° C. for 15 minutes and 2-(bromomethyl)pyridine hydrobromide (835 mg, 3.3 mmol) was added portionwise over 5 minutes. The mixture was stirred at 0° C. for 30 minutes and then at room temperature for 20 hours. The reaction was treated with ice water and extracted with dichloromethane. The mixture was applied to a SCX ion exchange cartridge and washed with methanol and then 2M ammonia in methanol. The basic fractions were combined and evaporated. The residue was purified by silica gel chromatography eluting with 0-10% methanol in dichloromethane to give methyl 3-methyl-2-oxo-1-(2-pyridinylmethyl)-4-imidazolidinecarboxylate (190 mg), LC/MS [M+H]$^+$=250.

(ii) A stirred solution of methyl 3-methyl-2-oxo-1-(2-pyridinylmethyl)-4-imidazolidinecarboxylate (190 mg, 0.76 mmol) in tetrahydrofuran (1.5 ml)/water (1 ml) at 0° C. was treated with lithium hydroxide (55 mg, 2.28 mmol) and the reaction mixture was stirred at 0-5° C. for 3 hours. The reaction was acidified to pH 2 with 2N hydrochloric acid and the solvent was evaporated. The residue was dried to give 3-methyl-2-oxo-1-(2-pyridinylmethyl)-4-imidazolidinecarboxylic acid which was used crude in the next step.

Example 10

N-{[2-Chloro-3-(trifluoromethyl)phenyl]methyl}-3-methyl-2-oxo-1-(2-pyrimidinyl)-4-imidazolidinecarboxamide (E10)

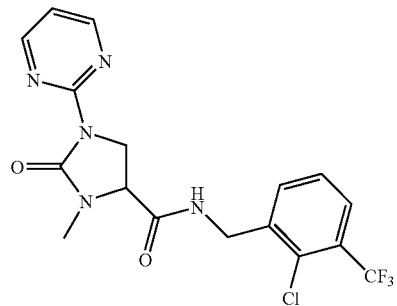

A suspension of crude 3-methyl-2-oxo-1-(2-pyrimidinyl)-4-imidazolidinecarboxylic acid (0.6 mmol) in dichloromethane (10 ml) was treated with 1-hydroxybenzotriazole hydrate (98 mg, 0.72 mmol), 1-ethyl-3-(3-dimethylaminopropyl)carbodiimide hydrochloride (138 mg, 0.72 mmol) and N-ethyl morpholine (0.3 ml, 2.4 mmol) was stirred at room temperature for 10 minutes. {[2-Chloro-3-(trifluoromethyl)phenyl]methyl}amine (126 mg, 0.6 mmol) was added. The reaction was diluted with dichloromethane (10 ml) and N,N-dimethylformamide (1 ml) and stirred at room temperature for 18 hours. Additional 1-ethyl-3-(3-dimethylaminopropyl)carbodiimide hydrochloride (138 mg, 0.72 mmol) was added and the suspension was stirred at room temperature for 5 days. The mixture was diluted with dichloromethane and the solution was washed with saturated sodium hydrogen carbonate solution, water, citric acid solution, water and brine, dried and evaporated. The residue was purified by mass-directed automated HPLC. The solid was triturated with ether/hexanes, collected and dried to give N-{[2-chloro-3-(trifluoromethyl)phenyl]methyl}-3-methyl-2-oxo-1-(2-pyrimidinyl)-4-imidazolidinecarboxamide (42 mg), LC/MS [M+H]$^+$=414, retention time=2.30 minutes.

The 3-methyl-2-oxo-1-(2-pyrimidinyl)-4-imidazolidinecarboxylic acid used in the method described above was prepared as follows:

(i) A suspension of methyl 3-methyl-2-oxo-4-imidazolidinecarboxylate (316 mg, 2 mmol) (prepared as described in step (ii) of Example 8) in THF (10 ml) was stirred at −40° C. Lithium hexamethyldisilazide (2 ml, 1M solution in THF) was added dropwise and the mixture was stirred at −40° C. for 15 minutes and then at −70° C. for 1 hour. A solution of 2-bromopyrimidine (318 mg, 2 mmol) in THF (1 ml) was added dropwise and the reaction was stirred at −70° C. for 1 hour and then warmed to 0° C. over 1 hour and then stirred at room temperature overnight. The reaction mixture was diluted with citric acid solution and dichloromethane. The organic layer was separated, washed with water and brine, dried and evaporated. The residue was purified by silica gel chromatography eluting with 0-10% methanol in dichloromethane to give crude methyl 3-methyl-2-oxo-1-(2-pyrimidinyl)-4-imidazolidinecarboxylate (144 mg) which was used in the next step, LC/MS [M+H]$^+$=237.

(ii) A stirred solution of methyl 3-methyl-2-oxo-1-(2-pyrimidinyl)-4-imidazolidinecarboxylate (144 mg, 0.6 mmol) in THF (1.5 ml) at 0° C. was treated with lithium hydroxide (72 mg, 3 mmol) in water (1 ml) and the reaction mixture was stirred at 0-5° C. for 1 hours. The reaction was acidified to pH 2 with 2N hydrochloric acid and the solvent was evaporated. The residue dried to give 3-methyl-2-oxo-1-(2-pyrimidinyl)-4-imidazolidinecarboxylic acid which was used crude in the next step, LC/MS [M+H]$^+$=223.

Example 11

N-{[2-Chloro-3-(trifluoromethyl)phenyl]methyl}-3-methyl-2-oxo-1-(4-piperidinyl)-4-imidazolidinecarboxamide hydrochloride (E11)

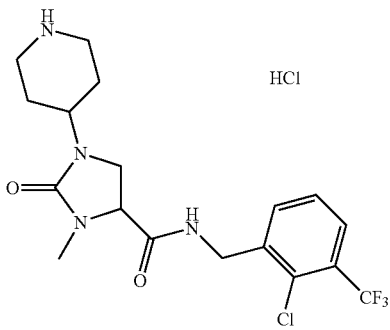

A solution of 1,1-dimethylethyl 4-{4-[({[2-chloro-3-(trifluoromethyl)phenyl]methyl}amino)carbonyl]-3-methyl-2-oxo-1-imidazolidinyl}-1-piperidinecarboxylate (218 mg, 0.42 mmol) in 1,4-dioxane (3 ml) was treated with 4M hydrogen chloride in 1,4-dioxane (1 ml) and the reaction was stirred at room temperature for 4 hours. The solvent was evaporated and the gum was dissolved in methanol and the solvent evaporated. The residue was triturated with ether and the solid was collected and dried to give N-{[2-chloro-3-(trifluoromethyl)phenyl]methyl}-3-methyl-2-oxo-1-(4-piperidinyl)-4-imidazolidinecarboxamide hydrochloride (153 mg, 80%), LC/MS [M+H]$^+$=419, retention time=1.75 minutes.

The 1,1-dimethylethyl 4-{4-[({[2-chloro-3-(trifluoromethyl)phenyl]methyl}amino)carbonyl]-3-methyl-2-oxo-1-imidazolidinyl}-1-piperidinecarboxylate used in the method described above was prepared as follows:
(i) A solution of 1,1-dimethylethyl 4-oxo-1-piperidinecarboxylate (3.0 g, 15 mmol) in THF (45 ml) was stirred at −78° C. under argon. Lithium hexamethyldisilazide (15 ml, 15 mmol, 1M solution in THF) was added dropwise and the reaction was stirred at −78° C. for 1 hour. A solution of 1,1,1-trifluoro-N-phenyl-N-[(trifluoromethyl)sulfonyl]methanesulfonamide (6.43 g, 18 mmol) in THF (12 ml) was added dropwise. The reaction was allowed to warm to room temperature over 2 hours. The reaction was quenched by the addition of water and the THF was evaporated. The residue was extracted with ether. The ether layer was separated and washed with water, 2N sodium hydroxide solution, water and brine, dried and evaporated. The residue was purified by silica gel chromatography eluting with 5-25% ethyl acetate in hexanes to give 1,1-dimethylethyl 4-{[(trifluoromethyl)sulfonyl]oxy}-3,6-dihydro-1(2H)-pyridinecarboxylate (2.91 g, 59%).
(ii) A solution of 1,1-dimethylethyl 4-{[(trifluoromethyl)sulfonyl]oxy}-3,6-dihydro-1(2H)-pyridinecarboxylate (2.65 g, 8 mmol), methyl 3-methyl-2-oxo-4-imidazolidinecarboxylate (1.26 g, 8 mmol) (prepared as described in step (ii) of Example 8) in 1,4-dioxane (50 ml) was treated with cesium carbonate (3.91 g, 12 mmol), Xantphos™ (348 mg, 0.6 mmol) and tris(dibenzylideneacetone)dipalladium(0) (183 mg, 0.2 mmol). The mixture was flushed with argon and the reaction was heated at reflux for 1 hour. After cooling to room temperature, the reaction mixture was diluted with water and extracted with ethyl acetate. The organic layers were washed with water and brine, dried and evaporated. The residue was purified by silica gel chromatography eluting with 0-100% ethyl acetate in hexanes to give 1,1-dimethylethyl 4-{3-methyl-4-[(methyloxy)carbonyl]-2-oxo-1-imidazolidinyl}-3,6-dihydro-1(2H)-pyridinecarboxylate (1.7 g, 63%), LC/MS [M+H]$^+$=340.

(iii) A solution of 1,1-dimethylethyl 4-{3-methyl-4-[(methyloxy)carbonyl]-2-oxo-1-imidazolidinyl}-3,6-dihydro-1 (2H)-pyridinecarboxylate (1.36 g, 4 mmol) in ethyl acetate (30 ml) containing palladium on charcoal (100 mg, 10% paste) was hydrogenated at room temperature and pressure for 24 hours. The mixture was filtered through Celite and the filtrate was evaporated. The residue was purified by silica gel chromatography eluting with 50-100% ethyl acetate in hexanes to give 1,1-dimethylethyl 4-{3-methyl-4-[(methyloxy)carbonyl]-2-oxo-1-imidazolidinyl}-1-piperidinecarboxylate (205 mg, 15%), LC/MS [M+H]$^+$=342.

(iv) A solution of 1,1-dimethylethyl 4-{3-methyl-4-[(methyloxy)carbonyl]-2-oxo-1-imidazolidinyl}-1-piperidinecarboxylate (200 mg, 0.58 mmol) in THF (3 ml) was stirred at 0° C. A solution of lithium hydroxide (15 mg, 0.64 mmol) in water (2 ml) was added and the reaction was stirred at 0° C. under argon for 90 minutes. The solution was acidified to pH 4 with 2N hydrochloric acid and the solvent was evaporated. The residue was co-evaporated with toluene and the residue dried over phosphorous pentoxide under high vacuum to give crude 1-(1-{[(1,1-dimethylethyl)oxy]carbonyl}-4-piperidinyl)-3-methyl-2-oxo-4-imidazolidinecarboxylic acid which was used in the next step, LC/MS [M+H]$^+$=328.

(v) To a stirred suspension of 1-(1-{[(1,1-dimethylethyl)oxy] carbonyl}-4-piperidinyl)-3-methyl-2-oxo-4-imidazolidinecarboxylic acid (0.55 mmol) in dichloromethane (10 ml) was added 1-hydroxybenzotriazole hydrate (89 mg, 0.66 mmol), 1-ethyl-3-(3-dimethylaminopropyl)carbodiimide hydrochloride (127 mg, 0.66 mmol) and N-ethyl morpholine (0.21 ml, 1.65 mmol) and the mixture was stirred at room temperature for 15 minutes. A solution of {[2-chloro-3-(trifluoromethyl)phenyl]methyl}amine (115 mg, 0.55 mmol) was added and the reaction was stirred at room temperature for 3 hours. The reaction was diluted with dichloromethane and the solution was washed with saturated sodium hydrogen carbonate solution, water, citric acid solution, water and brine, dried and evaporated. The residue was purified by silica gel chromatography eluting with 5-10% methanol in dichloromethane to give 1,1-dimethylethyl 4-{4-[({[2-chloro-3-(trifluoromethyl)phenyl]methyl}amino)carbonyl]-3-methyl- 2-oxo-1-imidazolidinyl}-1-piperidinecarboxylate (243 mg, 85%), LC/MS [M+H]⁺=519, retention time=2.89 minutes.

Example 12

N-{[2-Chloro-3-(trifluoromethyl)phenyl]methyl}-3-methyl-2-oxo-1-(3-pyridinyl)-4-imidazolidinecarboxamide (E12)

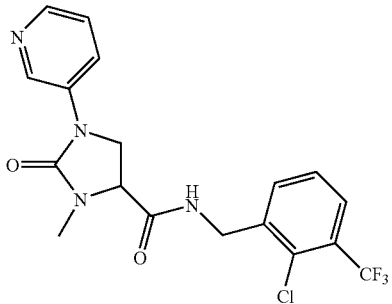

A mixture of crude 3-methyl-2-oxo-1-(3-pyridinyl)-4-imidazolidinecarboxylic acid (0.8 mmol), 1-hydroxybenzotriazole hydrate (147 mg, 0.96 mmol), 1-ethyl-3-(3-dimethylaminopropyl)carbodiimide hydrochloride (184 mg, 0.96 mmol), and N-ethyl morpholine (0.307 ml, 2.4 mmol) in dichloromethane (15 ml) was stirred at room temperature for 10 minutes. A solution of {[2-chloro-3-(trifluoromethyl)phenyl]methyl}amine (168 mg, 0.8 mmol) in dichloromethane (1 ml) was added and the reaction stirred at room temperature for 4 hours. The mixture was partitioned between dichloromethane and saturated sodium hydrogen carbonate solution. The organic phase was separated, washed with water and brine, dried and evaporated. The residue was purified by mass-directed automated HPLC. The solid was dissolved in methanol (5 ml) and anhydrous HCl in ether (1M, 0.5 ml) was added and the solution was evaporated. The resulting solid was collected, washed with ether and dried to give a pale yellow solid. The solid was dissolved in methanol and applied to a SCX ion exchange cartridge and washed with methanol and then 2M ammonia in methanol. The basic fractions were combined and evaporated and the resulting residue was triturated with ether, collected and dried to give N-{[2-Chloro-3-(trifluoromethyl)phenyl]methyl}-3-methyl-2-oxo-1-(3-pyridinyl)-4-imidazolidinecarboxamide (27 mg, 8%). LC/MS [M+H]⁺=413, retention time=1.96 minutes.

The 3-methyl-2-oxo-1-(3-pyridinyl)-4-imidazolidinecarboxylic acid used in the method described above was prepared as follows:
(i) A solution of 3-bromopyridine (316 mg, 2. mmol) and methyl 3-methyl-2-oxo-4-imidazolidinecarboxylate (316 mg, 2 mmol) (prepared as described in step (ii) of Example 8) in 1,4-dioxane (10 ml) was treated with cesium carbonate (977 mg, 3 mmol), Xantphos™ (87 mg, 0.15 mmol) (4,5-bis(diphenylphosphino)-9,9-dimethylxanthene, e.g. available from Aldrich, CAS no. 161265-03-8) and tris(dibenzylideneacetone)dipalladium(0) (45.8 mg, 0.05 mmol) and the mixture was heated under reflux under argon for 22 hours. After cooling to room temperature, the reaction mixture was diluted with water and extracted with ethyl acetate (×3). The organic layers were combined, washed with water and brine and evaporated in vacuo. The residue was purified by silica gel chromatography eluting with 0-10% methanol in dichloromethane to give methyl 3-methyl-2-oxo-1-(3-pyridinyl)-4-imidazolidinecarboxylate (273 mg, 58%). LC/MS [M+H]⁺=236.

(ii) A solution of methyl 3-methyl-2-oxo-1-(3-pyridinyl)-4-imidazolidinecarboxylate (0.27 g, 1.15 mmol) in tetrahydrofuran (3 ml) at 0° C. was treated with a solution of lithium hydroxide (0.030 g, 1.26 mmol) in water (2 ml) and the mixture was stirred at 0° C. for 90 minutes. Hydrochloric acid (2M) was added to adjust the pH of the reaction mixture to pH 2 and the solvent was evaporated. The residue was dried over phosphorus pentoxide to give crude 3-methyl-2-oxo-1-(3-pyridinyl)-4-imidazolidinecarboxylic acid which was used in the next step. LC/MS [M+H]⁺=222.

Example 13

N-{[2-Chloro-3-(trifluoromethyl)phenyl]methyl}-3-methyl-1-(6-methyl-3-pyridinyl)-2-oxo-4-imidazolidinecarboxamide (E13) (in a form obtainable or prepared from (4S)-2-oxo-3-{[(phenylmethyl)oxy]carbonyl}-4-imidazolidinecarboxylic acid)

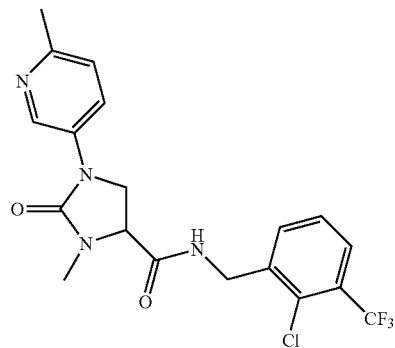

A mixture of 3-methyl-1-(6-methyl-3-pyridinyl)-2-oxo-4-imidazolidinecarboxylic acid TFA salt (175 mg, 0.5 mmol), 1-hydroxybenzotriazole hydrate (115 mg, 0.75 mmol), 1-ethyl-3-(3-dimethylaminopropyl)carbodiimide hydrochloride (144 mg, 0.75 mmol) and N-ethyl morpholine (0.319 ml, 2.5 mmol) in dichloromethane (8 ml) was stirred at room temperature for 10 minutes. A solution of {[2-chloro-3-(trifluoromethyl)phenyl]methyl}amine (105 mg, 0.5 mmol) in dichloromethane (2 ml) was added and the reaction stirred at room temperature for 4 hours. The mixture was partitioned between dichloromethane and saturated sodium hydrogen carbonate solution. The organic phase was separated, washed with water and brine, dried and evaporated. The residue was purified by silica gel chromatography eluting with 0-10% methanol in dichloromethane to give N-{[2-chloro-3-(trifluoromethyl)phenyl]methyl}-3-methyl-1-(6-methyl-3-pyridinyl)-2-oxo-4-imidazolidinecarboxamide (95 mg, 44%). LC/MS [M+H]⁺=427, retention time=1.98 minutes.

The 3-methyl-1-(6-methyl-3-pyridinyl)-2-oxo-4-imidazolidinecarboxylic acid TFA salt used in the method described above was prepared as follows:
Step (i) Phosphorus oxychloride (2.2 ml, 24 mmol) was added dropwise to a stirred solution of (4S)-2-oxo-3-{[(phenylmethyl)oxy]carbonyl}-4-imidazolidinecarboxylic acid (5.28 g, 20 mmol) in pyridine (10 ml), tert-butanol (15 ml) and chloroform (25 ml) at −10° C. The mixture was stirred at −5 to 0° C. for 30 minutes and then at room temperature for 4 hours. The solution was added dropwise to stirred ice water (200 ml)

containing sodium acetate (~40 g). The mixture was diluted with chloroform (100 ml) and the mixture was stirred for 30 minutes. The organic layer was separated, washed with cold 0.1M hydrochloric acid, water, saturated sodium hydrogen carbonate solution, water and brine, dried (MgSO4) and evaporated. The residue was dried to give 5-(1,1-dimethylethyl)1-(phenylmethyl)2-oxo-1,5-imidazolidinedicarboxylate (5.65 g, 88%) as a colourless solid. LC/MS [M+H]$^+$=321.

[For a method similar to this step (i), see: K. Hayashi et al., *J. Med. Chem.*, 1989, 32(2), 289-297; e.g. see Scheme 1 and compounds (5) and (6a) on p. 289 therein and synthesis of compound (6a) in p. 293 experimental section therein, incorporated herein by reference.]

Step (ii) To a stirred solution of 5-(1,1-dimethylethyl)1-(phenylmethyl)2-oxo-1,5-imidazolidinedicarboxylate (4.16 g, 13 mmol) in DMF (60 ml) at 0° C. was added sodium hydride (60% dispersion in oil) (0.546 g, 13.65 mmol). After 40 minutes at 0° C. iodomethane (4.06 ml, 65.0 mmol) was added and the reaction was allowed to warm to room temperature. After 6 hours the solvent was evaporated and the residue was partitioned between ethyl acetate and water. The organic phase was separated, washed with water and brine, dried (MgSO$_4$) and evaporated. The residue was purified by silica gel chromatography eluting with 30-100% ethyl acetate in hexanes to give 4-(1,1-dimethylethyl)1-(phenylmethyl)3-methyl-2-oxo-1,4-imidazolidinedicarboxylate (3.12 g, 9.33 mmol, 72%) (LC/MS [M+H]$^+$=335) and 5-(1,1-dimethylethyl)1-(phenylmethyl)3-methyl-2-oxo-1,5-imidazolidinedicarboxylate (560 mg, 1.675 mmol, 12%) (LC/MS [M+H]$^+$=335).

Step (iii) A solution of 4-(1,1-dimethylethyl)1-(phenylmethyl)3-methyl-2-oxo-1,4-imidazolidinedicarboxylate (3.12 g, 9.33 mmol) in methanol (40 ml) containing Pd/C (10% paste, 400 mg) was hydrogenated at room temperature and pressure for 18 hours. The mixture was filtered through a filter pad and the pad washed with methanol. The filtrates were combined, evaporated and dried to give 1,1-dimethylethyl 3-methyl-2-oxo-4-imidazolidinecarboxylate (1.76 g, 94%). LC/MS [M+H]$^+$=201.

Step (iv) A solution of 1,1-dimethylethyl 3-methyl-2-oxo-4-imidazolidinecarboxylate (300 mg, 1.5 mmol) and 5-bromo-2-methylpyridine (258 mg, 1.5 mmol) in 1,4-dioxane (10 ml) was treated with cesium carbonate (733 mg, 2.25 mmol), Xantphos™ (65.1 mg, 0.113 mmol) and tris(dibenzylideneacetone)dipalladium(0) (34.3 mg, 0.038 mmol) and the mixture was heated under reflux under argon for 18 hours. After cooling to room temperature, the reaction mixture was diluted with water and extracted with ethyl acetate. The organic layers were combined, washed with water and brine and evaporated in vacuo. The residue was purified by silica gel chromatography eluting with 0-10% methanol in dichloromethane to give 1,1-dimethylethyl 3-methyl-1-(6-methyl-3-pyridinyl)-2-oxo-4-imidazolidinecarboxylate (352 mg, 81%). LC/MS [M+H]$^+$=292.

Step (v) A solution of 1,1-dimethylethyl 3-methyl-1-(6-methyl-3-pyridinyl)-2-oxo-4-imidazolidinecarboxylate (352 mg, 1.2 mmol) in TFA/DCM (1:2, 6 ml) was stirred at room temperature for 6 hours. The solution was evaporated and the residue was dried to give crude acid (assume ~1.2 mmol, TFA salt) which was used in the next step. LC/MS [M+H]$^+$=236.

Example 14

N-[(2-Chloro-4-fluorophenyl)methyl]-3-methyl-1-(6-methyl-3-pyridinyl)-2-oxo-4-imidazolidinecarboxamide (E14) (in a form obtainable or prepared from (4S)-2-oxo-3-{[(phenylmethyl)oxy]carbonyl}-4-imidazolidinecarboxylic acid)

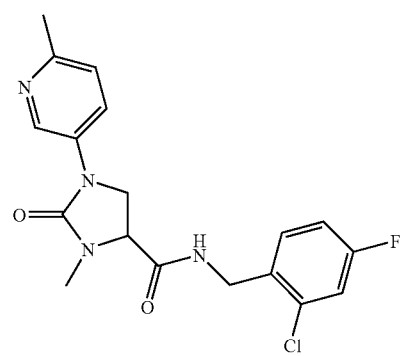

In a manner analogous to that described in Example 13 above N-[(2-chloro-4-fluorophenyl)methyl]-3-methyl-1-(6-methyl-3-pyridinyl)-2-oxo-4-imidazolidinecarboxamide was prepared substituting [(2-chloro-4-fluorophenyl)methyl]amine for the {[2-chloro-3-(trifluoromethyl)phenyl]methyl}amine used in the above procedure. LC/MS [M+H]$^+$=377, retention time=1.71 minutes.

Example 15

N-{[2-Chloro-3-(trifluoromethyl)phenyl]methyl}-3-methyl-1-(2-methyl-4-pyridinyl)-2-oxo-4-imidazolidinecarboxamide (E15) (in a form obtainable or prepared from (4S)-2-oxo-3-{[(phenylmethyl)oxy]carbonyl}-4-imidazolidinecarboxylic acid)

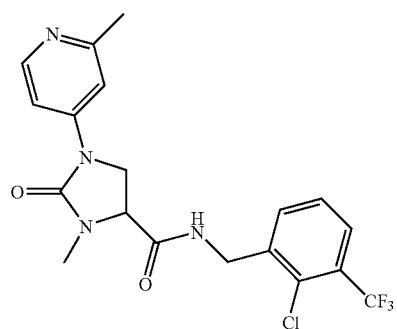

In a manner analogous to that described in Example 13 above N-{[2-chloro-3-(trifluoromethyl)phenyl]methyl}-3-methyl-1-(2-methyl-4-pyridinyl)-2-oxo-4-imidazolidinecarboxamide was prepared substituting 4-bromo-2-methylpyridine for 5-bromo-2-methylpyridine used in Step (iv) of the above procedure. LC/MS [M+H]⁺=427, retention time=1.91 minutes.

Example 16

N-{[2-Chloro-3-(trifluoromethyl)phenyl]methyl}-3-methyl-1-(6-methyl-2-pyridinyl)-2-oxo-4-imidazolidinecarboxamide (E16) (in a form obtainable or prepared from (4S)-2-oxo-3-{[(phenylmethyl)oxy]carbonyl}-4-imidazolidinecarboxylic acid)

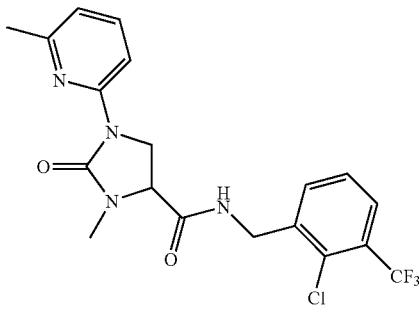

A mixture of 3-methyl-1-(6-methyl-2-pyridinyl)-2-oxo-4-imidazolidinecarboxylic acid TFA salt (147 mg, 0.42 mmol), 1-hydroxybenzotriazole hydrate (96 mg, 0.63 mmol), 1-ethyl-3-(3-dimethylaminopropyl)carbodiimide hydrochloride (121 mg, 0.63 mmol) and N-ethyl morpholine (0.27 ml, 2.1 mmol) in dichloromethane (8 ml) was stirred at room temperature for 10 minutes. A solution of {[2-chloro-3-(trifluoromethyl)phenyl]methyl}amine (88 mg, 0.42 mmol) in dichloromethane (2 ml) was added and the reaction stirred at room temperature for 4 hours. The mixture was partitioned between dichloromethane and saturated sodium hydrogen carbonate solution. The organic phase was separated, washed with water and brine, dried and evaporated. The residue was purified by silica gel chromatography eluting with 0-10% methanol in dichloromethane to give N-{[2-chloro-3-(trifluoromethyl)phenyl]methyl}-3-methyl-1-(6-methyl-2-pyridinyl)-2-oxo-4-imidazolidinecarboxamide (110 mg, 61%). LC/MS [M+H]⁺=427, retention time=2.66 minutes.

The 3-methyl-1-(6-methyl-2-pyridinyl)-2-oxo-4-imidazolidinecarboxylic acid TFA salt used in the method described above was prepared as follows:
(i) A solution of 1,1-dimethylethyl 3-methyl-2-oxo-4-imidazolidinecarboxylate (300 mg, 1.5 mmol) (prepared as described in step (iii) of Example 13, starting from (4S)-2-oxo-3-{[(phenylmethyl)oxy]carbonyl}-4-imidazolidinecarboxylic acid) and 2-bromo-6-methylpyridine (258 mg, 1.5 mmol) in 1,4-dioxane (10 ml) was treated with cesium carbonate (733 mg, 2.25 mmol), Xantphos™ (65.1 mg, 0.113 mmol) and tris(dibenzylideneacetone)dipalladium(0) (34.3 mg, 0.038 mmol) and the mixture was heated under reflux under argon for 18 hours. After cooling to room temperature, the reaction mixture was diluted with water and extracted with ethyl acetate. The organic layers were combined, washed with water and brine and evaporated in vacuo. The residue was purified by silica gel chromatography eluting with 0-100% ethyl acetate in isohexane to give 1,1-dimethylethyl 3-methyl-1-(6-methyl-2-pyridinyl)-2-oxo-4-imidazolidinecarboxylate (246 mg, 56%). LC/MS [M+H]⁺=292.
(ii) A solution of 1,1-dimethylethyl 3-methyl-1-(6-methyl-2-pyridinyl)-2-oxo-4-imidazolidinecarboxylate (246 mg, 0.84 mmol) in TFA/DCM (1:2, 6 ml) was stirred at room temperature for 6 hours. The solution was evaporated and the residue was dried to give 3-methyl-1-(6-methyl-2-pyridinyl)-2-oxo-4-imidazolidinecarboxylic acid TFA salt (assume ~0.84 mmol) which was used in the next step. LC/MS [M+H]⁺=236.

Example 17

N-[(2-Chloro-4-fluorophenyl)methyl]-3-methyl-1-(6-methyl-2-pyridinyl)-2-oxo-4-imidazolidinecarboxamide (E17) (in a form obtainable or prepared from (4S)-2-oxo-3-{[(phenylmethyl)oxy]carbonyl}-4-imidazolidinecarboxylic acid)

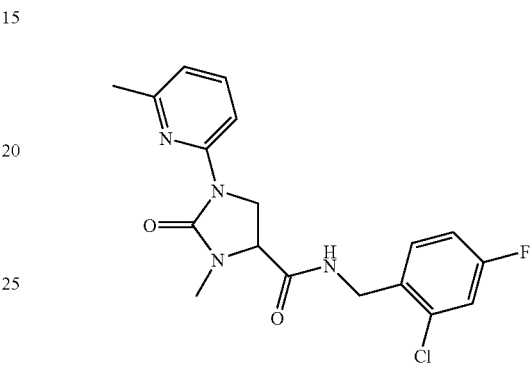

In a manner analogous to that described in Example 16 above N-[(2-chloro-4-fluorophenyl)methyl]-3-methyl-1-(6-methyl-2-pyridinyl)-2-oxo-4-imidazolidinecarboxamide was prepared substituting [(2-chloro-4-fluorophenyl)methyl]amine for the {[2-chloro-3-(trifluoromethyl)phenyl]methyl}amine used in the above procedure. LC/MS [M+H]⁺=377, retention time=2.33 minutes.

Example 18

N-[(2,4-Dichlorophenyl)methyl]-3-methyl-1-(2-methyl-3-pyridinyl)-2-oxo-4-imidazolidinecarboxamide (E18) (in a form obtainable or prepared from (4S)-2-oxo-3-{[(phenylmethyl)oxy]carbonyl}-4-imidazolidinecarboxylic acid)

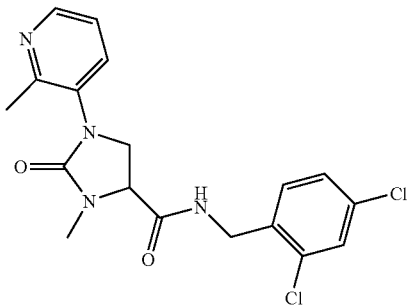

A mixture of 3-methyl-1-(2-methyl-3-pyridinyl)-2-oxo-4-imidazolidinecarboxylic acid TFA salt (279 mg, 0.8 mmol), 1-hydroxybenzotriazole hydrate (147 mg, 0.96 mmol), 1-ethyl-3-(3-dimethylaminopropyl)carbodiimide hydrochloride (184 mg, 0.96 mmol) and N-ethyl morpholine (0.613 ml, 4.8 mmol) in dichloromethane (18 ml) was stirred at room temperature for 10 minutes. A solution of [1-(2,4-dichlorophenyl)methyl]amine (141 mg, 0.8 mmol) in dichloromethane (2 ml) was added and the reaction stirred at room temperature for 4 hours. The mixture was partitioned between dichloromethane and saturated sodium hydrogen carbonate solution. The organic phase was separated, washed with water and brine, dried and evaporated. The residue was purified by silica gel chromatography eluting with 0-10% methanol in dichloromethane to give N-[(2,4-dichlorophenyl)methyl]-3-methyl-1-(2-methyl-3-pyridinyl)-2-oxo-4-imidazolidinecarboxamide (147 mg, 47%). LC/MS [M+H]$^+$=393, retention time=1.76 minutes.

Enantiomeric excess=95.7%, as determined by chiral chromatography Method (C), indicative of (4S)—N-[(2,4-dichlorophenyl)methyl]-3-methyl-1-(2-methyl-3-pyridinyl)-2-oxo-4-imidazolidinecarboxamide, retention time=8.06 minutes.

The 3-methyl-1-(2-methyl-3-pyridinyl)-2-oxo-4-imidazolidinecarboxylic acid TFA salt used in the method described above was prepared as follows:

(i) A solution of 1,1-dimethylethyl 3-methyl-2-oxo-4-imidazolidinecarboxylate (600 mg, 3.00 mmol) (prepared as described in step (iii) of Example 13) and 3-bromo-2-methylpyridine (515 mg, 3.00 mmol) in 1,4-dioxane (20 ml) was treated with cesium carbonate (1464 mg, 4.49 mmol), Xantphos™ (130 mg, 0.225 mmol) and tris(dibenzylideneacetone)dipalladium(0) (68.6 mg, 0.075 mmol) and the mixture was heated under reflux under argon for 18 hours. After cooling to room temperature, the reaction mixture was diluted with water and extracted with ethyl acetate. The organic layers were combined, washed with water and brine and evaporated in vacuo. The residue was purified by silica gel chromatography eluting with 0-10% methanol in dichloromethane to give 1,1-dimethylethyl 3-methyl-1-(2-methyl-3-pyridinyl)-2-oxo-4-imidazolidinecarboxylate (738 mg, 85%). LC/MS [M+H]$^+$=292.

(ii) A solution of 1,1-dimethylethyl 3-methyl-1-(2-methyl-3-pyridinyl)-2-oxo-4-imidazolidinecarboxylate (738 mg, 2.53 mmol) in TFA/DCM (1:2, 12 ml) was stirred at room temperature for 6 hours. The solution was evaporated and the residue was co-evaporated with toluene and dried to give crude 3-methyl-1-(2-methyl-3-pyridinyl)-2-oxo-4-imidazolidinecarboxylic acid TFA salt (assume ~2.5 mmol) which was used in the next step.

Examples 19-22

In forms obtainable or prepared from (4S)-2-oxo-3-{[(phenylmethyl)oxy]carbonyl}-4-imidazolidinecarboxylic acid In a manner analogous to that described for Example 18 above the compounds tabulated below (Table 2) were prepared by substituting the appropriate amine (or salt thereof) for the [(2,4-dichlorophenyl)methyl]amine used in the above procedure. All of the amines used to make the amines shown in Table 2 are available from commercial sources or can be prepared using routes described previously in the chemical literature or analogous methods.

TABLE 2

| Example no. | Chemical name | [M + H]$^+$ | Retention time (mins) |
|---|---|---|---|
| E19 | 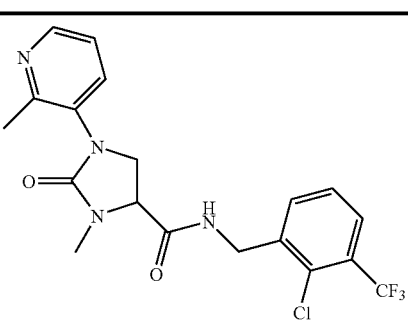<br>N-{[2-Chloro-3-(trifluoromethyl)phenyl]methyl}-3-methyl-1-(2-methyl-4-pyridinyl)-2-oxo-4-imidazolidinecarboxamide | 427 | 1.97 |
| E20 | 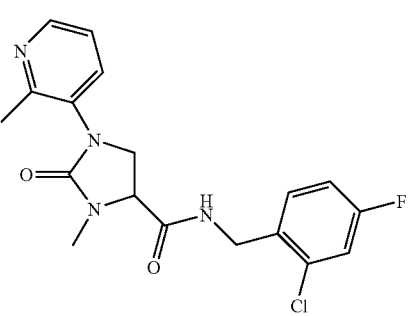<br>N-[(2-Chloro-4-fluorophenyl)methyl]-3-methyl-1-(2-methyl-3-pyridinyl)-2-oxo-4-imidazolidinecarboxamide | 377 | 1.69 |

TABLE 2-continued

| Example no. | Chemical name | [M + H]+ | Retention time (mins) |
|---|---|---|---|
| E21 | 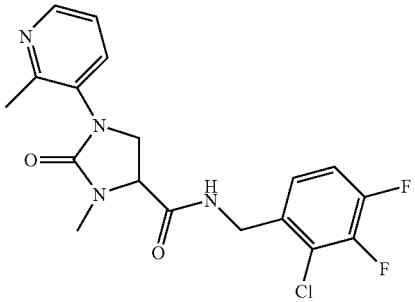<br>N-[(2-Chloro-3,4-difluorophenyl)methyl]-3-methyl-1-(2-methyl-3-pyridinyl)-2-oxo-4-imidazolidinecarboxamide | 395 | 1.65 |
| E22 | 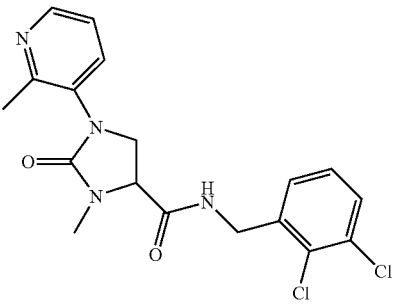<br>N-[(2,3-Dichlorophenyl)methyl]-3-methyl-1-(2-methyl-3-pyridinyl)-2-oxo-4-imidazolidinecarboxamide | 393 | 1.73 |

Example 23

N-{[2-Chloro-3-(trifluoromethyl)phenyl]methyl}-3-methyl-2-oxo-1-(2-pyridinyl)-4-imidazolidinecarboxamide (E23) (in a form obtainable or prepared from (4S)-2-oxo-3-{[(phenylmethyl)oxy]carbonyl}-4-imidazolidinecarboxylic acid)

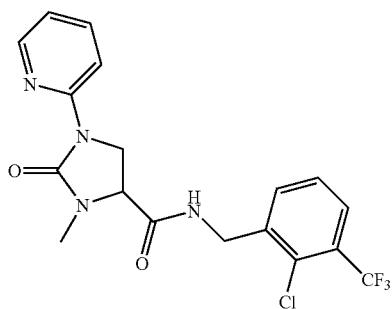

A mixture of 3-methyl-2-oxo-1-(2-pyridinyl)-4-imidazolidinecarboxylic acid TFA salt (117 mg, 0.35 mmol), 1-hydroxybenzotriazole hydrate (80 mg, 0.525 mmol), 1-ethyl-3-(3-dimethylaminopropyl)carbodiimide hydrochloride (101 mg, 0.525 mmol) and N-ethyl morpholine (0.224 ml, 1.75 mmol) in dichloromethane (8 ml) was stirred at room temperature for 10 minutes. A solution of {[2-chloro-3-(trifluoromethyl)phenyl]methyl}amine (73.4 mg, 0.35 mmol) in dichloromethane (2 ml) was added and the reaction stirred at room temperature for 18 hours. The mixture was partitioned between dichloromethane and saturated sodium hydrogen carbonate solution. The organic phase was separated, washed with water and brine, dried and evaporated. The residue was purified by silica gel chromatography eluting with 0-10% methanol in dichloromethane to give N-{[2-chloro-3-(trifluoromethyl)phenyl]methyl}-3-methyl-2-oxo-1-(2-pyridinyl)-4-imidazolidinecarboxamide (90 mg, 62%). LC/MS [M+H]+=413, retention time=2.55 minutes.

The 3-methyl-2-oxo-1-(2-pyridinyl)-4-imidazolidinecarboxylic acid TFA salt used in the method described above was prepared as follows:

(i) A solution of 1,1-dimethylethyl 3-methyl-2-oxo-4-imidazolidinecarboxylate (400 mg, 2 mmol) (prepared as described in step (iii) of Example 13) and 2-bromopyridine (316 mg, 2 mmol) in 1,4-dioxane (10 ml) was treated with cesium carbonate (977 mg, 3 mmol), Xantphos™ (87 mg, 0.15 mmol) and tris(dibenzylideneacetone)dipalladium(0) (45.8 mg, 0.05 mmol) and the mixture was heated under reflux under argon for 18 hours. After cooling to room temperature, the reaction mixture was diluted with water and extracted with ethyl acetate. The organic layers were combined, washed with water and brine and evaporated in vacuo. The residue was purified by silica gel chromatography eluting with 0-100% ethyl acetate in isohexane (2 columns required) to give 1,1-dimethylethyl 3-methyl-2-oxo-1-(2-pyridinyl)-4-imidazolidinecarboxylate (198 mg, 36%). LC/MS [M+H]+=278.

(ii) A solution of 1,1-dimethylethyl 3-methyl-2-oxo-1-(2-pyridinyl)-4-imidazolidinecarboxylate (198 mg, 0.71 mmol) in TFA/DCM (1:2, 4.5 ml) was stirred at room temperature for 8 hours. The solution was evaporated and the residue was dried to give 3-methyl-2-oxo-1-(2-pyridinyl)-4-imidazolidinecarboxylic acid TFA salt (assume ~0.71 mmol)) which was used in the next step. LC/MS [M+H]$^+$=222.

Example 24

N-[(2-Chloro-4-fluorophenyl)methyl]-3-methyl-2-oxo-1-(2-pyridinyl)-4-imidazolidinecarboxamide (E24) (in a form obtainable or prepared from (4S)-2-oxo-3-{[(phenylmethyl)oxy]carbonyl}-4-imidazolidinecarboxylic acid)

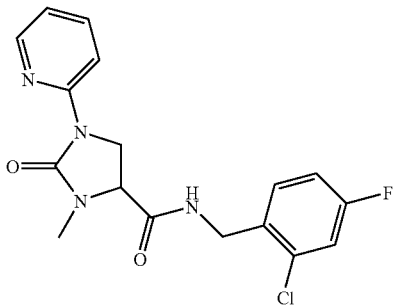

In a manner analogous to that described in Example 23 above N-[(2-chloro-4-fluorophenyl)methyl]-3-methyl-2-oxo-1-(2-pyridinyl)-4-imidazolidinecarboxamide was prepared substituting [(2-chloro-4-fluorophenyl)methyl]amine for the {[2-chloro-3-(trifluoromethyl)phenyl]methyl}amine used in the above procedure. LC/MS [M+H]$^+$=363, retention time=2.21 minutes.

Example 25

N-[(2-Chloro-3,4-difluorophenyl)methyl]-3-methyl-1-(3-methyl-2-pyridinyl)-2-oxo-4-imidazolidinecarboxamide (E25) (in a form obtainable or prepared from (4S)-2-oxo-3-{[(phenylmethyl)oxy]carbonyl}-4-imidazolidinecarboxylic acid)

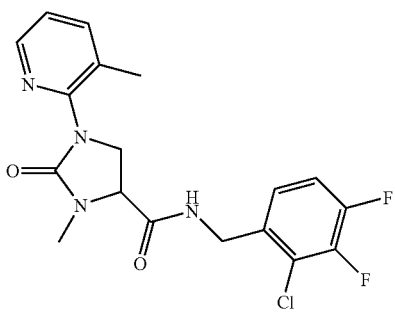

A mixture of 3-methyl-1-(3-methyl-2-pyridinyl)-2-oxo-4-imidazolidinecarboxylic acid TFA salt (279 mg, 0.8 mmol), 1-hydroxybenzotriazole hydrate (147 mg, 0.96 mmol), 1-ethyl-3-(3-dimethylaminopropyl)carbodiimide hydrochloride (184 mg, 0.96 mmol) and N-ethyl morpholine (0.613 ml, 4.8 mmol) in dichloromethane (20 ml) was stirred at room temperature for 10 minutes. [(2-Chloro-3,4-difluorophenyl)methyl]amine hydrochloride (171 mg, 0.8 mmol) was added and the reaction stirred at room temperature for 18 hours. The mixture was diluted with dichloromethane and was washed with 3N citric acid solution. The organic phase was separated, washed with brine, dried and evaporated. The residue was purified by mass-directed automated HPLC to give N-[(2-chloro-3,4-difluorophenyl)methyl]-3-methyl-1-(3-methyl-2-pyridinyl)-2-oxo-4-imidazolidinecarboxamide (145 mg, 46%). LC/MS [M+H]$^+$=395, retention time=2.36 minutes.

The 3-methyl-1-(3-methyl-2-pyridinyl)-2-oxo-4-imidazolidinecarboxylic acid TFA salt used in the method described above was prepared as follows:

(i) A solution of 1,1-dimethylethyl 3-methyl-2-oxo-4-imidazolidinecarboxylate (600 mg, 3 mmol) (prepared as described in step (iii) of Example 13, starting from (4S)-2-oxo-3-{[(phenylmethyl)oxy]carbonyl}-4-imidazolidinecarboxylic acid) and 2-bromo-3-methylpyridine (515 mg, 3 mmol) in 1,4-dioxane (20 ml) was treated with cesium carbonate (1464 mg, 4.5 mmol), Xantphos™ (130 mg, 0.225 mmol) and tris(dibenzylideneacetone)dipalladium(0) (68.6 mg, 0.075 mmol) and the mixture was heated under reflux under argon for 18 hours. After cooling to room temperature, the reaction mixture was diluted with water and extracted with ethyl acetate. The organic layers were combined, washed with water and brine and evaporated in vacuo. The residue was purified by silica gel chromatography eluting with 0-100% ethyl acetate in isohexane to give 1,1-dimethylethyl 3-methyl-1-(3-methyl-2-pyridinyl)-2-oxo-4-imidazolidinecarboxylate (700 mg, 80%). LC/MS [M+H]$^+$=292.

(ii) A solution of 1,1-dimethylethyl 3-methyl-1-(3-methyl-2-pyridinyl)-2-oxo-4-imidazolidinecarboxylate (700 mg, 2.4 mmol) in TFA/DCM (1:2, 12 ml) was stirred at room temperature for 6 hours. The solution was evaporated and the residue was co-evaporated with toluene and dried to give 3-methyl-1-(3-methyl-2-pyridinyl)-2-oxo-4-imidazolidinecarboxylic acid TFA salt (assume ~2.4 mmol) which was used in the next step. LC/MS [M+H]$^+$=236.

Examples 26-27

In forms obtainable or prepared from (4S)-2-oxo-3-{[(phenylmethyl)oxy]carbonyl}-4-imidazolidinecarboxylic acid In a manner analogous to that described for Example 25 above the compounds tabulated below (Table 3) were prepared by substituting the appropriate amine (or salt thereof) for the [(2-chloro-3,4-difluorophenyl)methyl]amine hydrochloride used in the above procedure. All of the amines used to make the amines shown in Table 3 are available from commercial sources or can be prepared using routes described previously in the chemical literature or analogous methods.

TABLE 3

Retention

| Example no. | Chemical name | [M + H]+ | time (mins) |
|---|---|---|---|
| E26 | N-{[2-Chloro-3-(trifluoromethyl)phenyl]methyl}-3-methyl-1-(3-methyl-2-pyridinyl)-2-oxo-4-imidazolidinecarboxamide | 427 | 2.54 |
| E27 | N-[(2,4-Dichlorophenyl)methyl]-3-methyl-1-(3-methyl-2-pyridinyl)-2-oxo-4-imidazolidinecarboxamide | 393 | 2.47 |

Example 28

N-[(2-Chloro-3,4-difluorophenyl)methyl]-3-methyl-2-oxo-4-imidazolidinecarboxamide (E28) (in a form obtainable or prepared from (4S)-2-oxo-3-{[(phenylmethyl)oxy]carbonyl}-4-imidazolidinecarboxylic acid)

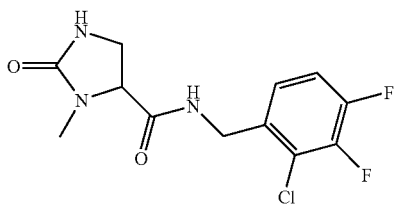

A mixture of 3-methyl-2-oxo-4-imidazolidinecarboxylic acid (115 mg, 0.8 mmol), 1-hydroxybenzotriazole hydrate (147 mg, 0.96 mmol), 1-ethyl-3-(3-dimethylaminopropyl)carbodiimide hydrochloride (184 mg, 0.96 mmol) and N-ethyl morpholine (0.613 ml, 4.8 mmol) in dichloromethane (18 ml) was stirred at room temperature for 10 minutes. A solution of [(2-chloro-3,4-difluorophenyl)methyl]amine (142 mg, 0.8 mmol) in dichloromethane (2 ml) was added and the reaction stirred at room temperature for 18 hours. The mixture was diluted with dichloromethane (60 ml) and the mixture was washed with 3N citric acid solution (30 ml). The organic phase was separated, washed with brine, dried and evaporated. The residue was purified by mass-directed automated HPLC to give N-[(2-Chloro-3,4-difluorophenyl)methyl]-3-methyl-2-oxo-4-imidazolidinecarboxamide (95 mg, 39%). LC/MS [M+H]+=304, retention time=1.99 minutes.

The 3-methyl-2-oxo-4-imidazolidinecarboxylic acid used in the method described above was prepared as follows:
A solution of 1,1-dimethylethyl 3-methyl-2-oxo-4-imidazolidinecarboxylate (801 mg, 4 mmol) (prepared as described in step (iii) of Example 13, starting from (4S)-2-oxo-3-{[(phenylmethyl)oxy]carbonyl}-4-imidazolidinecarboxylic acid) in TFA/DCM (trifluoroacetic acid/dichloromethane) (1:2, 9 ml) was stirred at room temperature for 6 hours. The solution was evaporated, the residue was co-evaporated with toluene and dried to give crude 3-methyl-2-oxo-4-imidazolidinecarboxylic acid (assume ~4 mmol) which was used in the next step. LC/MS [M+H]+=145.

Examples 29-30

In forms obtainable or prepared from (4S)-2-oxo-3-{[(phenylmethyl)oxy]carbonyl}-4-imidazolidinecarboxylic acid In a manner analogous to that described for Example 28 above the compounds tabulated below (Table 4) were prepared by substituting the appropriate amine (or salt thereof) for the [(2-chloro-3,4-difluorophenyl)methyl]amine used in the above procedure. All of the amines used to make the amines shown in Table 4 are available from commercial sources or can be prepared using routes described previously in the chemical literature or analogous methods.

TABLE 4

| Example no. | Chemical name | [M + H]⁺ | Retention time (mins) |
|---|---|---|---|
| E29 | 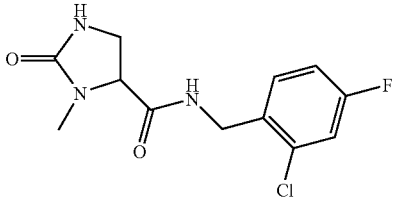<br>N-[(2-Chloro-4-fluorophenyl)methyl]-3-methyl-2-oxo-4-imidazolidinecarboxamide | 286 | 1.89 |
| E30 | 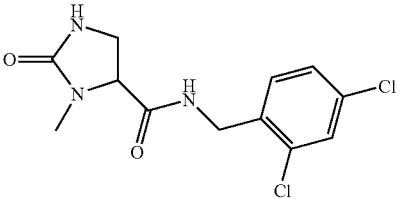<br>N-[(2,4-Dichlorophenyl)methyl]-3-methyl-2-oxo-4-imidazolidinecarboxamide | 302 | 2.10 |

Example 31

N-[(2-Chloro-4-fluorophenyl)methyl]-3-methyl-2-oxo-1-(3-pyridinyl)-4-imidazolidinecarboxamide (E31) (in a form obtainable or prepared from (4S)-2-oxo-3-{[(phenylmethyl)oxy]carbonyl}-4-imidazolidinecarboxylic acid)

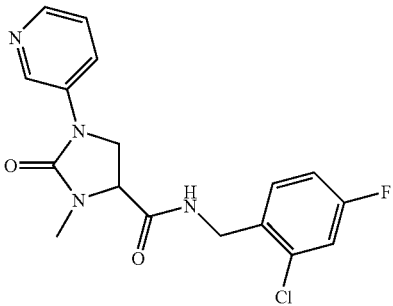

A solution of N-[(2-chloro-4-fluorophenyl)methyl]-3-methyl-2-oxo-4-imidazolidinecarboxamide (28.6 mg, 0.1 mmol) (prepared as described in Example 29) and 3-bromopyridine (15.8 mg, 0.1 mmol) in 1,4-dioxane (3 ml) was treated with cesium carbonate (81 mg, 0.25 mmol), Xantphos™ (4.3 mg, 0.075 mmol) and tris(dibenzylideneacetone)dipalladium(0) (2.3 mg, 0.025 mmol) and the mixture was heated under reflux under argon for 18 hours. After cooling to room temperature, the reaction mixture was diluted with saturated sodium hydrogen carbonate solution and extracted with dichloromethane. The organic layers were combined, washed with water and brine and evaporated in vacuo. The residue was purified by silica gel chromatography eluting with 0-10% methanol in dichloromethane. The resulting residue was triturated with ether, the solid collected and dried to give N-[(2-chloro-4-fluorophenyl)methyl]-3-methyl-2-oxo-1-(3-pyridinyl)-4-imidazolidinecarboxamide (18 mg, 50%). LC/MS [M+H]⁺=363, retention time 1.68 minutes.

Example 32

N-[(2,4-Dichlorophenyl)methyl]-3-methyl-2-oxo-1-(2-pyrimidinyl)-4-imidazolidinecarboxamide (E32) (in a form obtainable or prepared from (4S)-2-oxo-3-{[(phenylmethyl)oxy]carbonyl}-4-imidazolidinecarboxylic acid)

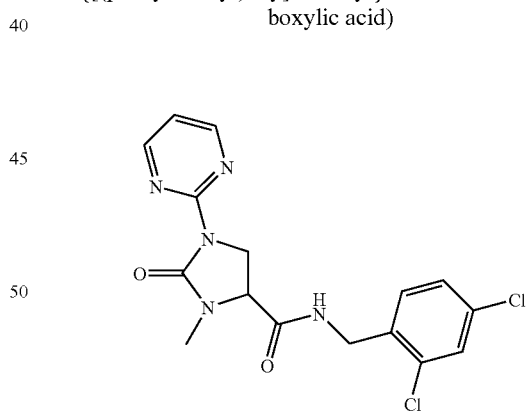

A mixture of 3-methyl-2-oxo-1-(2-pyrimidinyl)-4-imidazolidinecarboxylic acid TFA salt (168 mg, 0.5 mmol), 1-hydroxybenzotriazole hydrate (101 mg, 0.75 mmol), 1-ethyl-3-(3-dimethylaminopropyl)carbodiimide hydrochloride (144 mg, 0.75 mmol) and N-ethyl morpholine (0.316 ml, 2.5 mmol) in dichloromethane (8 ml) was stirred at room temperature for 10 minutes. A solution of [1-(2,4-dichlorophenyl)methyl]amine (0.067 ml, 0.5 mmol) in dichloromethane (2 ml) was added and the reaction stirred at room temp for 4 hours. The mixture was partitioned between dichloromethane and saturated sodium hydrogen carbonate, The organic phase was separated, washed with water and brine, dried and evaporated. The residue was purified by silica gel chromatography eluting with 0-10% methanol in dichloromethane to give N-[(2,4-dichlorophenyl)methyl]-3-methyl-2-oxo-1-(2-pyrimidinyl)-4-imidazolidinecarboxamide (20 mg, 10.5% yield). LC/MS [M+H]$^+$=380, retention time=2.22 minutes.

The 3-methyl-2-oxo-1-(2-pyrimidinyl)-4-imidazolidinecarboxylic acid TFA salt used in the method described above was prepared as follows:

(i) A solution of 1,1-dimethylethyl 3-methyl-2-oxo-4-imidazolidinecarboxylate (801 mg, 4 mmol) (prepared as described in step (iii) of Example 13, starting from (4S)-2-oxo-3-{[(phenylmethyl)oxy]carbonyl}-4-imidazolidinecarboxylic acid) and 2-bromopyrimidine (636 mg, 4 mmol) in 1,4-dioxane (20 ml) was treated with cesium carbonate (1955 mg, 6 mmol), Xantphos™ (174 mg, 0.3 mmol) and tris(dibenzylideneacetone)dipalladium(0) (92 mg, 0.1 mmol) and the mixture was heated under reflux under argon for 1 hour. After cooling to room temperature, the reaction mixture was diluted with water and extracted with ethyl acetate. The organic layers were combined, washed with water and brine and evaporated in vacuo. The residue was purified by silica gel chromatography eluting with 0-20% methanol in ethyl acetate to 1,1-dimethylethyl 3-methyl-2-oxo-1-(2-pyrimidinyl)-4-imidazolidinecarboxylate (360 mg, 32%). LC/MS [M+H]$^+$=279.

(ii) A solution of 1,1-dimethylethyl 3-methyl-2-oxo-1-(2-pyrimidinyl)-4-imidazolidinecarboxylate (0.557 g, 2 mmol) in TFA/DCM (1:2, 7.5 ml) was stirred at room temperature for 6 hours. The solution was evaporated and the residue was dried to give crude (4S)-3-methyl-2-oxo-1-(2-pyrimidinyl)-4-imidazolidinecarboxylic acid TFA salt (assume ~2 mmol) which was used in the next step. LC/MS [M+H]$^+$=223.

Examples 33-35

In forms obtainable or prepared from (4S)-2-oxo-3-{[(phenylmethyl)oxy]carbonyl}-4-imidazolidinecarboxylic acid In a manner analogous to that described for Example 32 above the compounds tabulated below (Table 5) were prepared by substituting the appropriate amine (or salt thereof) for the [1-(2,4-dichlorophenyl)methyl]amine used in the above procedure. All of the amines used to make the amines shown in Table 5 are available from commercial sources or can be prepared using routes described previously in the chemical literature or analogous methods.

TABLE 5

| Example no. | Chemical name | [M + H]$^+$ | Retention time (mins) |
|---|---|---|---|
| E33 | 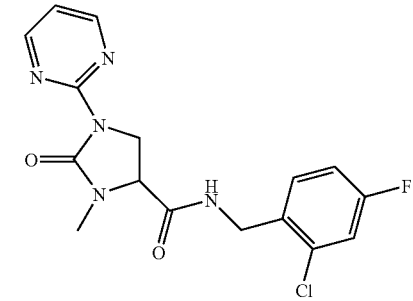<br>N-[(2-Chloro-4-fluorophenyl)methyl]-3-methyl-2-oxo-1-(2-pyrimidinyl)-4-imidazolidinecarboxamide | 366 | 2.03 |
| E34 | 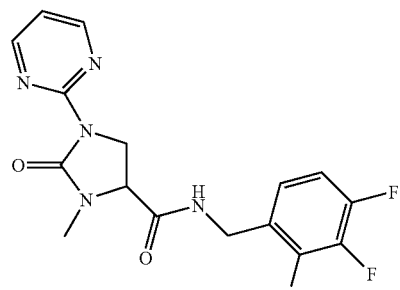<br>N-[(2-Chloro-3,4-difluorophenyl)methyl]-3-methyl-2-oxo-1-(2-pyrimidinyl)-4-imidazolidinecarboxamide | 382 | 2.11 |

TABLE 5-continued

| Example no. | Chemical name | [M + H]+ | Retention time (mins) |
|---|---|---|---|
| E35 | 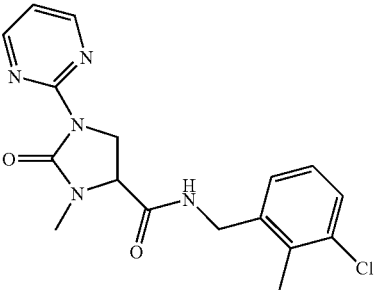<br>N-[(3-Chloro-2-methylphenyl)methyl]-3-methyl-2-oxo-1-(2-pyrimidinyl)-4-imidazolidinecarboxamide | 360 | 2.18 |

Example 36

N-[(2-Chloro-3,4-difluorophenyl)methyl]-3-methyl-1-(2-methyl-4-pyridinyl)-2-oxo-4-imidazolidinecarboxamide (E36) (in a form obtainable or prepared from (4S)-2-oxo-3-{[(phenylmethyl)oxy]carbonyl}-4-imidazolidinecarboxylic acid

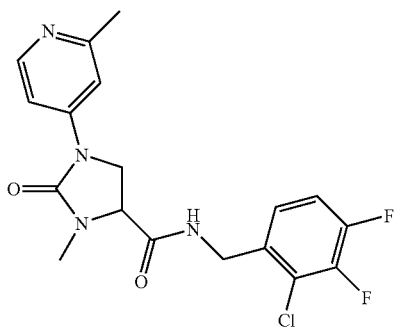

A solution of N-[(2-chloro-3,4-difluorophenyl)methyl]-3-methyl-2-oxo-4-imidazolidinecarboxamide (152 mg, 0.5 mmol) (prepared as described in Example 28) and 4-bromo-2-methylpyridine (86 mg, 0.5 mmol) in 1,4-dioxane (3 ml) was treated with cesium carbonate (244 mg, 0.75 mmol), Xantphos™ (21.7 mg, 0.038 mmol) and tris(dibenzylideneacetone)dipalladium(0) (11.5 mg, 0.013 mmol) and the mixture was heated under reflux under argon for 3 hours. After cooling to room temperature, the reaction mixture was diluted with saturated sodium hydrogen carbonate solution and extracted with dichloromethane. The organic layers were combined, washed with water and brine and evaporated in vacuo. The residue was purified by silica gel chromatography eluting with 0-10% methanol in dichloromethane. The resulting residue was triturated with ether, the solid was collected and dried to give N-[(2-chloro-3,4-difluorophenyl)methyl]-3-methyl-1-(2-methyl-4-pyridinyl)-2-oxo-4-imidazolidinecarboxamide (123 mg, 62%). LC/MS [M+H]+=395, retention time=1.68 minutes.

Example 37

N-[(2-Chloro-3,4-difluorophenyl)methyl]-3-methyl-1-[(4-methyl-1H-imidazol-5-yl)methyl]-2-oxo-4-imidazolidinecarboxamide (E37) (in a form obtainable or prepared from (4S)-2-oxo-3-{[(phenylmethyl)oxy]carbonyl}-4-imidazolidinecarboxylic acid)

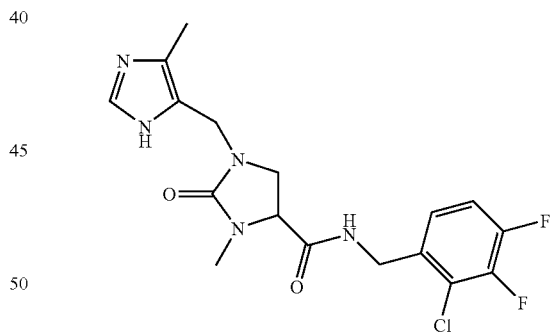

A solution of N-[(2-chloro-3,4-difluorophenyl)methyl]-3-methyl-2-oxo-4-imidazolidinecarboxamide (152 mg, 0.5 mmol) (prepared as described in Example 28), (4-methyl-1H-imidazol-5-yl)methanol hydrochloride (93 mg, 0.625 mmol) and p-toluene sulfonic acid monohydrate (19 mg, 0.100 mmol) in N-methyl-2-pyrrolidone (1 ml) was heated at 130° C. under argon for 3 h. The reaction mixture was cooled to room temperature and diluted with dichloromethane. The solution was washed with saturated sodium hydrogen carbonate solution and brine, dried and evaporated. The residue was purified by mass-directed automated HPLC, followed by trituration with ether to give N-[(2-chloro-3,4-difluorophenyl)methyl]-3-methyl-1-[(4-methyl-1H-imidazol-5-yl)methyl]-2-oxo-4-imidazolidinecarboxamide (147 mg, 74%). LC/MS [M+H]$^+$=398, retention time=1.57 minutes.

Example 38

N-[(2-Chloro-3,4-difluorophenyl)methyl]-3-methyl-1-[2-(4-morpholinyl)ethyl]-2-oxo-4-imidazolidinecarboxamide hydrochloride (E38)

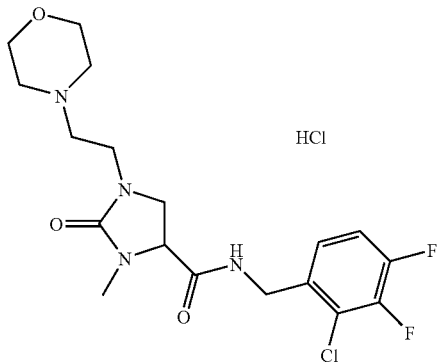

A mixture of N-[(2-chloro-3,4-difluorophenyl)methyl]-3-methyl-2-oxo-4-imidazolidinecarboxamide (100 mg, 0.33 mmol) (prepared as described in Example 28) and potassium carbonate (91 mg, 0.66 mmol) in DMF (1 ml) was stirred at room temperature for 10 minutes and 4-(2-chloroethyl)morpholine hydrochloride (61 mg, 0.33 mmol) was added. The mixture was stirred for 30 minutes and then heated at 60° C. for 3 h and 80° C. for 2 h. The mixture was cooled to room temperature and sodium hydride (40 mg, 60% dispersion in oil, 1 mmol) was added and the mixture heated at 50° C. for 16 h. The reaction mixture was cooled to room temperature and diluted with dichloromethane. The solution was washed with saturated sodium hydrogen carbonate solution and brine, dried and evaporated. The residue was purified by mass-directed automated HPLC to give two components with same molecular ion. Each component was converted to the corresponding HCl salt by dissolving the product from mass-directed automated HPLC in methanol/dichloromethane, adding an excess of 1M HCl in ether, evaporating the solvent, co-evaporating the residue with methanol and ether. The residue was triturated with ether/heptane and the solid collected and dried to give N-[(2-Chloro-3,4-difluorophenyl)methyl]-3-methyl-1-[2-(4-morpholinyl)ethyl]-2-oxo-4-imidazolidinecarboxamide hydrochloride (22 mg, 15%) (LC/MS [M+H]$^+$=417, retention time=1.40 minutes) and N-[(2-chloro-3,4-difluorophenyl)methyl]-3-methyl-1-[2-(4-morpholinyl) ethyl]-2-oxo-4-imidazolidinecarboxamide hydrochloride (6 mg, 4%) (LC/MS [M+H]$^+$=417, retention time=1.55 minutes).

Example 39

N-[(2-Chloro-3,4-difluorophenyl)methyl]-3-methyl-1-(1-methyl-1H-imidazol-4-yl)-2-oxo-4-imidazolidinecarboxamide (E39) (in a form obtainable or prepared from (4S)-2-oxo-3-{[(phenylmethyl)oxy]carbonyl}-4-imidazolidinecarboxylic acid)

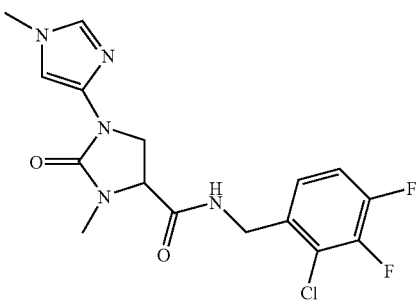

To a stirred mixture of N-[(2-chloro-3,4-difluorophenyl)methyl]-3-methyl-2-oxo-4-imidazolidinecarboxamide (100 mg, 0.33 mmol) (prepared as described in Example 28), 4-bromo-1-methyl-1H-imidazole (63.8 mg, 0.396 mmol) in 1,4-dioxane (6 ml) was added potassium phosphate (350 mg, 1.65 mmol), copper (I) iodide (62.8 mg, 0.33 mmol) and trans-N,N-dimethylcyclohexane-1,2-diamine (0.052 ml, 0.33 mmol) and the mixture was heated at reflux under argon for 1 h. The mixture was cooled to room temperature and partitioned between saturated sodium hydrogen carbonate solution and dichloromethane. The organic extracts were separated, washed with water and brine, dried and evaporated. The residue was purified by silica gel chromatography eluting with 0-20% methanol in dichloromethane, followed by mass-directed automated HPLC to give N-[(2-chloro-3,4-difluorophenyl)methyl]-3-methyl-1-(1-methyl-1H-imidazol-4-yl)-2-oxo-4-imidazolidinecarboxamide (15 mg, 12%). LC/MS [M+H]$^+$=384, retention time=1.71 minutes.

Example 40

N-[(2-Chloro-3,4-difluorophenyl)methyl]-3-methyl-1-(1-methyl-1H-imidazol-2-yl)-2-oxo-4-imidazolidinecarboxamide (E40) (in a form obtainable or prepared from (4S)-2-oxo-3-{[(phenylmethyl)oxy]carbonyl}-4-imidazolidinecarboxylic acid)

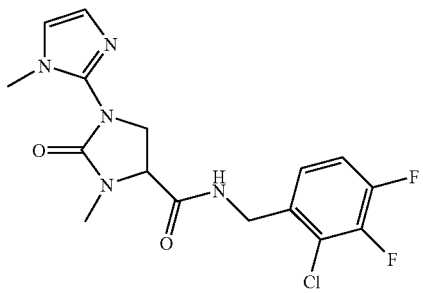

To a stirred mixture of N-[(2-chloro-3,4-difluorophenyl)methyl]-3-methyl-2-oxo-4-imidazolidinecarboxamide (91 mg, 0.3 mmol) (prepared as described in Example 28) and 2-bromo-1-methyl-1H-imidazole (48.3 mg, 0.3 mmol) in 1,4-dioxane (6 ml) was added potassium phosphate (318 mg, 1.5 mmol), copper (I) iodide (57.1 mg, 0.3 mmol) and trans-N,N-dimethylcyclohexane-1,2-diamine (0.047 ml, 0.3 mmol) and the mixture was heated at reflux under argon for 3 hours. The mixture was cooled to room temperature and partitioned between saturated sodium hydrogen carbonate solution and dichloromethane. The organic extracts were separated, washed with water and brine, dried and evaporated. The residue was purified by mass-directed automated HPLC to give N-[(2-chloro-3,4-difluorophenyl)methyl]-3-methyl-1-(1-methyl-1H-imidazol-2-yl)-2-oxo-4-imidazolidinecarboxamide (22 mg, 19%). LC/MS [M+H]$^+$=384, retention time=1.69 minutes.

Example 41

N-[(2-Chloro-3,4-difluorophenyl)methyl]-3-methyl-1-(1-methyl-1H-pyrazol-5-yl)-2-oxo-4-imidazolidinecarboxamide (E41) (in a form obtainable or prepared from (4S)-2-oxo-3-{[(phenylmethyl)oxy]carbonyl}-4-imidazolidinecarboxylic acid)

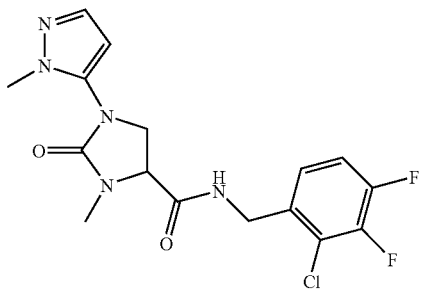

To a stirred mixture of N-[(2-chloro-3,4-difluorophenyl)methyl]-3-methyl-2-oxo-4-imidazolidinecarboxamide (60.7 mg, 0.2 mmol) (prepared as described in Example 28), 5-iodo-1-methyl-1H-pyrazole (41.6 mg, 0.2 mmol) in 1,4-dioxane (4 ml) was added potassium phosphate (212 mg, 1 mmol), copper (I) iodide (38.1 mg, 0.2 mmol) and trans-N,N-dimethylcyclohexane-1,2-diamine (0.032 ml, 0.2 mmol) and the mixture was heated at reflux under argon for 1 h. The mixture was cooled to room temperature and partitioned between saturated sodium hydrogen carbonate solution and dichloromethane. The organic extracts were separated, washed with water and brine, dried and evaporated. The residue was purified by mass-directed automated HPLC to give N-[(2-chloro-3,4-difluorophenyl)methyl]-3-methyl-1-(1-methyl-1H-pyrazol-5-yl)-2-oxo-4-imidazolidinecarboxamide (18 mg, 23%). LC/MS [M+H]$^+$=384, retention time=2.22 minutes.

Example 42

N-{[2-Chloro-3-(trifluoromethyl)phenyl]methyl}-3-methyl-1-[2-(4-morpholinyl)ethyl]-2-oxo-4-imidazolidinecarboxamide hydrochloride (E42)

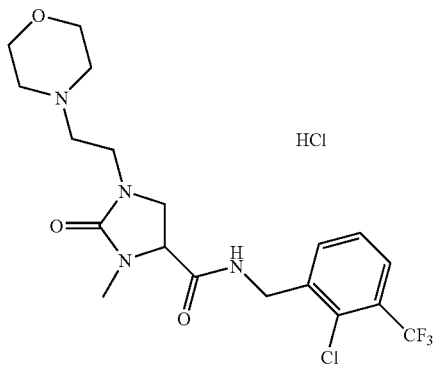

A mixture of 3-methyl-1-[2-(4-morpholinyl)ethyl]-2-oxo-4-imidazolidinecarboxylic acid TFA salt (186 mg, 0.5 mmol), N-ethyl morpholine (0.383 ml, 3 mmol), 1-hydroxybenzotriazole hydrate (92 mg, 0.6 mmol) and 1-ethyl-3-(3-dimethylaminopropyl)carbodiimide hydrochloride (115 mg, 0.6 mmol) in dichloromethane (9 ml) was stirred at room temperature for 10 minutes. A solution of {[2-chloro-3-(trifluoromethyl)phenyl]methyl}amine (105 mg, 0.5 mmol) in dichloromethane (1 ml) was added and the reaction stirred at room temperature for 18 hours. The mixture was diluted with dichloromethane and was washed with saturated sodium hydrogen carbonate solution. The organic phase was separated, washed with brine, dried and evaporated. The residue was purified by mass-directed automated HPLC. The product from mass-directed automated HPLC was dissolved in methanol (2 ml) and an excess of 1M hydrogen chloride in ether (0.5 ml) was added. The solvent was evaporated, the residue was triturated with ether and the solid collected and dried to give N-{[2-chloro-3-(trifluoromethyl)phenyl]methyl}-3-methyl-1-[2-(4-morpholinyl)ethyl]-2-oxo-4-imidazolidinecarboxamide hydrochloride (73 mg, 30%). LC/MS [M+H]$^+$=449, retention time=1.80 minutes.

The 3-methyl-1-[2-(4-morpholinyl)ethyl]-2-oxo-4-imidazolidinecarboxylic acid TFA salt used in the method described above was prepared as follows:

(i) To a stirred solution of 1,1-dimethylethyl 3-methyl-2-oxo-4-imidazolidinecarboxylate (1.0 g, 5 mmol) (prepared as described in step (iii) of Example 13) in N,N-dimethylformamide (20 ml) at 0° C. was added sodium hydride (60% dispersion in oil) (220 mg, 5.5 mmol). After 10 minutes a solution of 4-(2-chloroethyl)morpholine (898 mg, 6 mmol) in N,N-dimethylformamide (2 ml) and potassium iodide (166 mg, 1 mmol) was added and the mixture was heated at 70° C. for 2 hours. After cooling to room temperature water was added and the mixture was partitioned between saturated sodium hydrogen carbonate solution and dichloromethane. The organic extracts were separated, washed with water and brine, dried and evaporated. The residue was purified by silcia gel chromatography eluting with 5-10% 2M ammonia in methanol and dichloromethane to give 1,1-dimethylethyl-3-methyl-1-[2-(4-morpholinyl)ethyl]-2-oxo-4-imidazolidinecarboxylate (740 mg, 47%) as an oil. LC/MS [M+H]$^+$=314.

(ii) A solution of 1,1-dimethylethyl-3-methyl-1-[2-(4-morpholinyl)ethyl]-2-oxo-4-imidazolidinecarboxylate (740 mg, 2.361 mmol) in TFA/DCM (1:2, 6 ml) was stirred at room temperature for 5 hours. The solution was evaporated and the residue was co-evaporated with DCM and dried to give crude 3-methyl-1-[2-(4-morpholinyl)ethyl]-2-oxo-4-imidazolidinecarboxylic acid TFA salt (assume ~2.3 mmol) which was used in the next step. LC/MS [M+H]$^+$=258.

Examples 43-44

In a manner analogous to that described for Example 42 above the compounds tabulated below (Table 6) were prepared by substituting the appropriate amine (or salt thereof) for the {[2-chloro-3-(trifluoromethyl)phenyl]methyl}amine used in the above procedure. All of the amines used to make the amines shown in Table 6 are available from commercial sources or can be prepared using routes described previously in the chemical literature or analogous methods.

TABLE 6

| Example no. | Chemical name | [M + H]$^+$ | Retention time (mins) |
|---|---|---|---|
| E43 | 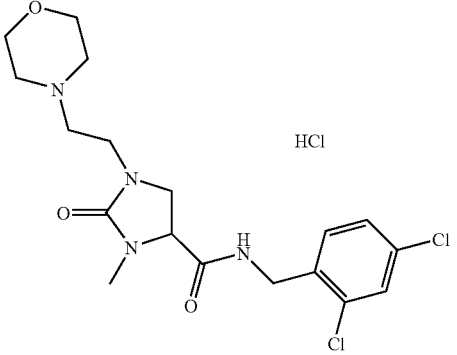 N-[(2,4-Dichlorophenyl)methyl]-3-methyl-1-[2-(4-morpholinyl)ethyl]-2-oxo-4-imidazolidinecarboxamide hydrochloride | 415 | 1.71 |
| E44 | 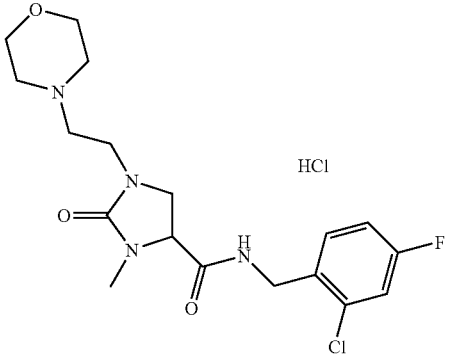 N-[(2-Chloro-4-fluorophenyl)methyl]-3-methyl-1-[2-(4-morpholinyl)ethyl]-2-oxo-4-imidazolidinecarboxamide hydrochloride | 399 | 1.51 |

Example 45

N-{[2-Chloro-3-(trifluoromethyl)phenyl]methyl}-3-methyl-2-oxo-1-(5-pyrimidinyl)-4-imidazolidinecarboxamide (E45) (in a form obtainable or prepared from (4S)-2-oxo-3-{[(phenylmethyl)oxy]carbonyl}-4-imidazolidinecarboxylic acid)

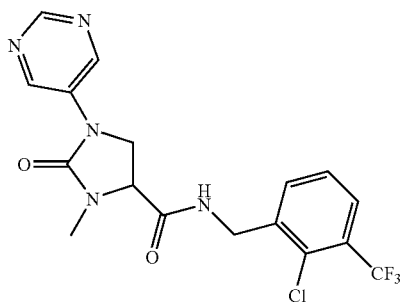

A solution of 3-methyl-2-oxo-1-(5-pyrimidinyl)-4-imidazolidinecarboxylic acid (0.6 mmol) in dichloromethane (6 ml) was treated with N-ethyl morpholine (0.460 ml, 3.60 mmol), 1-hydroxybenzotriazole hydrate (110 mg, 0.720 mmol) and 1-ethyl-3-(3-dimethylaminopropyl)carbodiimide hydrochloride (138 mg, 0.720 mmol) and the mixture was stirred at room temperature for 10 minutes. A solution of {[2-chloro-3-(trifluoromethyl)phenyl]methyl}amine (126 mg, 0.600 mmol) in dichloromethane (1 ml) was added and the reaction stirred at room temperature for 3 hours. The mixture was diluted with dichloromethane and the solution was washed with 3N citric acid, water, saturated sodium bicarbonate solution and brine, dried and evaporated. The residue was purified by mass-directed automated HPLC to give N-{[2-chloro-3-(trifluoromethyl)phenyl]methyl}-3-methyl-2-oxo-1-(5-pyrimidinyl)-4-imidazolidinecarboxamide (54 mg, 22%). LC/MS [M+H]$^+$=414, retention time 2.37 minutes.

The 3-methyl-2-oxo-1-(5-pyrimidinyl)-4-imidazolidinecarboxylic acid used in the method described above was prepared as follows:

(i) A solution of 1,1-dimethylethyl 3-methyl-2-oxo-4-imidazolidinecarboxylate (601 mg, 3 mmol) (prepared as described in step (iii) of Example 13, starting from (4S)-2-oxo-3-{[(phenylmethyl)oxy]carbonyl}-4-imidazolidinecarboxylic acid) and 5-bromopyrimidine (477 mg, 3.00 mmol) in 1,4-dioxane (20 ml) was treated with cesium carbonate (1466 mg, 4.50 mmol), Xantphos™ (130 mg, 0.225 mmol) and tris(dibenzylideneacetone)dipalladium(0) (68.7 mg, 0.075 mmol) and the mixture was heated under reflux under argon for 3 hours. After cooling to room temperature, the reaction mixture was diluted with water and extracted with ethyl acetate. The organic layers were combined, washed with water and brine and evaporated in vacuo. The residue was purified by silica gel chromatography eluting with 0-100% ethyl acetate in isohexane to give 1,1-dimethylethyl 3-methyl-2-oxo-1-(5-pyrimidinyl)-4-imidazolidinecarboxylate (349 mg, 42%). LC/MS [M+H]$^+$=279.

(ii) A solution of 1,1-dimethylethyl 3-methyl-2-oxo-1-(5-pyrimidinyl)-4-imidazolidinecarboxylate (630 mg, 2.264 mmol) in TFA/DCM (1:2, 9 ml) was stirred at room temperature for 8 hours. The solution was evaporated and the residue was co-evaporated with toluene and dried to give crude 3-methyl-2-oxo-1-(5-pyrimidinyl)-4-imidazolidinecarboxylic acid (assume ~2.2 mmol) which was used in the next step. LC/MS [M+H]$^+$=223.

Examples 46-47

In forms obtainable or prepared from (4S)-2-oxo-3-{[(phenylmethyl)oxy]carbonyl}-4-imidazolidinecarboxylic acid In a manner analogous to that described for Example 45 above the compounds tabulated below (Table 6) were prepared by substituting the appropriate amine (or salt thereof) for the {[2-chloro-3-(trifluoromethyl)phenyl]methyl}amine used in the above procedure. All of the amines used to make the amines shown in Table 7 are available from commercial sources or can be prepared using routes described previously in the chemical literature or analogous methods.

TABLE 7

| Example no. | Chemical name | [M + H]$^+$ | Retention time (mins) |
|---|---|---|---|
| E46 | N-[(2,4-Dichlorophenyl)methyl]-3-methyl-2-oxo-1-(5-pyrimidinyl)-4-imidazolidinecarboxamide | 380 | 2.28 |

TABLE 7-continued

| Example no. | Chemical name | [M + H]+ | Retention time (mins) |
|---|---|---|---|
| E47 | N-[(2-Chloro-4-fluorophenyl)methyl]-3-methyl-2-oxo-1-(5-pyrimidinyl)-4-imidazolidinecarboxamide | 364 | 2.08 |

Example 48

N-{[2-Chloro-3-(trifluoromethyl)phenyl]methyl}-3-methyl-1-[3-(4-morpholinyl)propyl]-2-oxo-4-imidazolidinecarboxamide hydrochloride (E48)

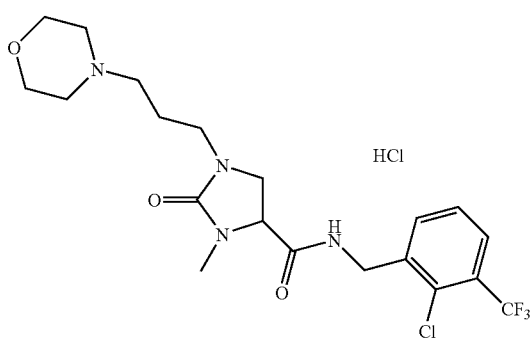

In a manner analogous to that described in Example 42 above N-{[2-chloro-3-(trifluoromethyl)phenyl]methyl}-3-methyl-1-[3-(4-morpholinyl)propyl]-2-oxo-4-imidazolidinecarboxamide hydrochloride was prepared substituting 4-(3-chloropropyl)morpholine for 4-(2-chloroethyl)morpholine used in Step (i) of the Example 42 procedure. LC/MS [M+H]+=463, retention time=1.82 minutes.

Example 49

N-{[2-Chloro-3-(trifluoromethyl)phenyl]methyl}-1-methyl-2-oxo-4-imidazolidinecarboxamide (E49) (in a form obtainable or prepared from (4S)-2-oxo-3-{[(phenylmethyl)oxy]carbonyl}-4-imidazolidinecarboxylic acid)

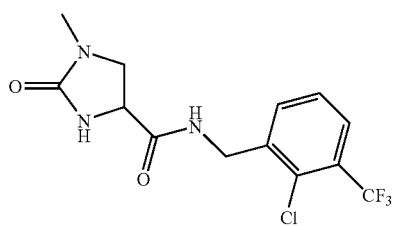

A mixture of 1-methyl-2-oxo-4-imidazolidinecarboxylic acid (144 mg, 1 mmol), N-ethyl morpholine (0.767 ml, 6.00 mmol), 1-hydroxybenzotriazole hydrate (184 mg, 1.200 mmol) and 1-ethyl-3-(3-dimethylaminopropyl)carbodiimide hydrochloride (230 mg, 1.200 mmol) in dichloromethane (18 ml) was stirred at room temperature for 10 minutes. A solution of {[2-chloro-3-(trifluoromethyl)phenyl]methyl}amine (210 mg, 1.000 mmol) in dichloromethane (2 ml) was added and the reaction stirred at room temperature for hours. The mixture was diluted with dichloromethane and the mixture was washed with 3N citric acid solution. The organic phase was separated, washed with brine, dried and evaporated. The residue was purified by mass-directed automated HPLC to give the N-{[2-chloro-3-(trifluoromethyl)phenyl]methyl}-1-methyl-2-oxo-4-imidazolidinecarboxamide (150 mg, 55%). LC/MS [M+H]+=336, retention time=2.22 minutes.

The 1-methyl-2-oxo-4-imidazolidinecarboxylic acid used in the method described above was prepared as follows:
(i) A solution of 5-(1,1-dimethylethyl)1-(phenylmethyl)3-methyl-2-oxo-1,5-imidazolidinedicarboxylate (3.8 g, 11.36 mmol) (prepared as described in step (ii) of Example 13, starting from (4S)-2-oxo-3-{[(phenylmethyl)oxy]carbonyl}-4-imidazolidinecarboxylic acid) in methanol (50 ml) containing Pd/C (10% paste, 400 mg) was hydrogenated at room temperature and pressure for 18 hours. The mixture was filtered through a filter pad and the pad washed with methanol. The filtrates were combined, evaporated and dried to give 1,1-dimethylethyl 1-methyl-2-oxo-4-imidazolidinecarboxylate (1.001 g, 5 mmol) (2.17 g, 95%); LC/MS [M+H]$^+$=201. (ii) A solution of 1,1-dimethylethyl 1-methyl-2-oxo-4-imidazolidinecarboxylate (1.001 g, 5 mmol) in TFA/DCM (1:2, 7.5 ml) was stirred at room temperature for 6 hours. The solution was evaporated and the residue was dried to give crude 1-methyl-2-oxo-4-imidazolidinecarboxylic acid (assume 5 mmol), which was used in the next step. LC/MS [M+H]$^+$=145.

Example 50

N-[(2-Chloro-4-fluorophenyl)methyl]-1-methyl-2-oxo-4-imidazolidinecarboxamide (E50) (in a form obtainable or prepared from (4S)-2-oxo-3-{[(phenylmethyl)oxy]carbonyl}-4-imidazolidinecarboxylic acid)

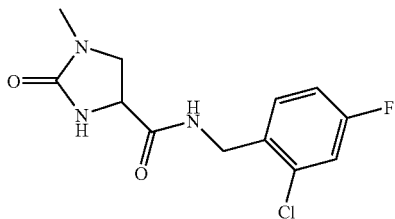

In a manner analogous to that described in Example 49 above N-[(2-chloro-4-fluorophenyl)methyl]-1-methyl-2-oxo-4-imidazolidinecarboxamide was prepared substituting [(2-chloro-4-fluorophenyl)methyl]amine for the {[2-chloro-3-(trifluoromethyl)phenyl]methyl}amine used in the above procedure. LC/MS [M+H]$^+$=286, retention time=1.90 minutes.

Example 51

N-{[2-Chloro-3-(trifluoromethyl)phenyl]methyl}-3-methyl-2-oxo-1-[4-(trifluoromethyl)-2-pyrimidinyl]-4-imidazolidinecarboxamide (E51) (in a form obtainable or prepared from (4S)-2-oxo-3-{[(phenylmethyl)oxy]carbonyl}-4-imidazolidinecarboxylic acid)

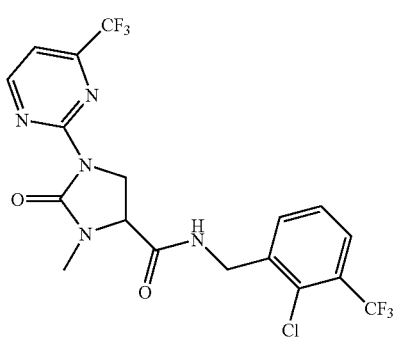

A mixture of crude 3-methyl-2-oxo-1-[4-(trifluoromethyl)-2-pyrimidinyl]-4-imidazolidinecarboxylic acid (10 ml of 0.05M solution in DCM, 0.5 mmol), N-ethylmorpholine (0.383 ml, 3.00 mmol), 1-hydroxybenzotriazole hydrate (92 mg, 0.600 mmol) and 1-ethyl-3-(3-dimethylaminopropyl)carbodiimide hydrochloride (115 mg, 0.600 mmol) was stirred at room temperature for 10 minutes. A solution of {[2-chloro-3-(trifluoromethyl)phenyl]methyl}amine (105 mg, 0.5 mmol) in dichloromethane (1 ml) was added and the reaction stirred at room temperature for 18 hours. The reaction mixture was diluted with dichloromethane and the solution was washed with saturated sodium hydrogen carbonate solution, water, aqueous citric acid, water and brine, dried and evaporated. The residue was purified by silica gel chromatography eluting with 0-10% methanol in dichloromethane. The residue was triturated with ether and the resulting solid was collected and dried to give N-{[2-chloro-3-(trifluoromethyl)phenyl]methyl}-3-methyl-2-oxo-1-[4-(trifluoromethyl)-2-pyrimidinyl]-4-imidazolidinecarboxamide (150 mg, 62%). LC/MS [M+H]$^+$=482, retention time 2.81 minutes.

The 3-methyl-2-oxo-1-[4-(trifluoromethyl)-2-pyrimidinyl]-4-imidazolidinecarboxylic acid used in the method described above was prepared as follows:

(i) A solution of 1,1-dimethylethyl 3-methyl-2-oxo-4-imidazolidinecarboxylate (600 mg, 3 mmol) (prepared as described in step (iii) of Example 13, starting from (4S)-2-oxo-3-{[(phenylmethyl)oxy]carbonyl}-4-imidazolidinecarboxylic acid) and 2-chloro-4-(trifluoromethyl)pyrimidine (547 mg, 3.00 mmol) in 1,4-dioxane (20 ml) was treated with cesium carbonate (1464 mg, 4.49 mmol), Xantphos™ (130 mg, 0.225 mmol) and tris(dibenzylideneacetone)dipalladium(0) (68.6 mg, 0.075 mmol) and the mixture was heated at reflux under argon for 6 hours. After cooling to room temperature, the reaction mixture was diluted with water and extracted with ethyl acetate. The organic layers were combined, washed with water and brine and evaporated. The residue was purified by silica gel chromatography eluting with 0-100% ethyl acetate in isohexane to give 1,1-dimethylethyl 3-methyl-2-oxo-1-[4-(trifluoromethyl)-2-pyrimidinyl]-4-imidazolidinecarboxylate (506 mg, 49%). LC/MS [M+H]$^+$=347.

(ii) A solution of 1,1-dimethylethyl 3-methyl-2-oxo-1-[4-(trifluoromethyl)-2-pyrimidinyl]-4-imidazolidinecarboxylate (506 mg, 1.46 mmol) in TFA/DCM (1:2, 9 ml) was stirred at room temperature for 16 hours. The solution was evaporated and the residue was co-evaporated with toluene and dried to give crude 3-methyl-2-oxo-1-[4-(trifluoromethyl)-2-pyrimidinyl]-4-imidazolidinecarboxylic acid (assume ~1.5 mmol) which was used in the next step. LC/MS [M+H]$^+$=291.

Examples 52-53

In forms obtainable or prepared from (4S)-2-oxo-3-{[(phenylmethyl)oxy]carbonyl}-4-imidazolidinecarboxylic acid)

In a manner analogous to that described for Example 51 above the compounds tabulated below (Table 8) were prepared by substituting the appropriate amine (or salt thereof) for the {[2-chloro-3-(trifluoromethyl)phenyl]methyl}amine used in the above procedure. All of the amines used in Table 8 are available from commercial sources or can be prepared using routes described previously in the chemical literature or analogous methods.

TABLE 8

| Example no. | Chemical name | [M + H]⁺ | Retention time (mins) |
|---|---|---|---|
| E52 | 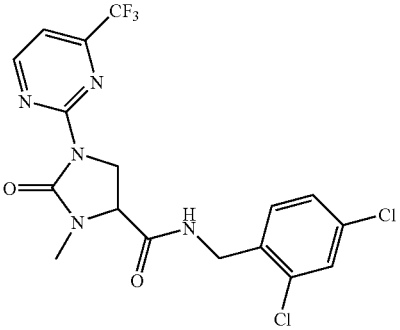<br>N-[(2,4-Dichlorophenyl)methyl]-3-methyl-2-oxo-1-[4-(trifluoromethyl)-2-pyrimidinyl]-4-imidazolidinecarboxamide | 448 | 2.77 |
| E53 | 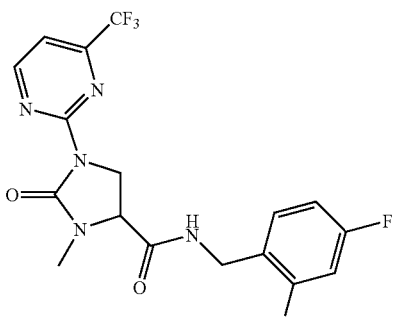<br>N-[(2-Chloro-4-fluorophenyl)methyl]-3-methyl-2-oxo-1-[4-(trifluoromethyl)-2-pyrimidinyl]-4-imidazolidinecarboxamide | 432 | 2.60 |

Example 54

N-{[2-Chloro-3-(trifluoromethyl)phenyl]methyl}-1-(2,6-dimethyl-3-pyridinyl)-3-methyl-2-oxo-4-imidazolidinecarboxamide (E54) (in a form obtainable or prepared from (4S)-2-oxo-3-{[(phenylmethyl)oxy]carbonyl}-4-imidazolidinecarboxylic acid)

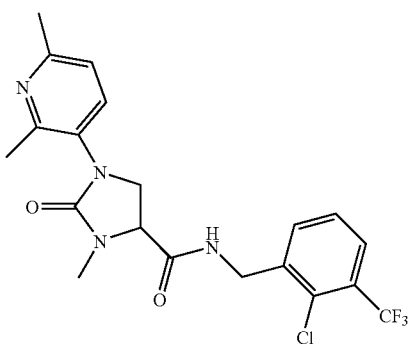

A mixture of crude 1-(2,6-dimethyl-3-pyridinyl)-3-methyl-2-oxo-4-imidazolidinecarboxylic acid TFA salt (10 ml of 0.05M solution in DCM, 0.5 mmol), N-ethylmorpholine (0.383 ml, 3.00 mmol), 1-hydroxybenzotriazole hydrate (92 mg, 0.600 mmol) and 1-ethyl-3-(3-dimethylaminopropyl)carbodiimide hydrochloride (115 mg, 0.600 mmol) was stirred at room temperature for 10 minutes. A solution of {[2-chloro-3-(trifluoromethyl)phenyl]methyl}amine (105 mg, 0.5 mmol) in dichloromethane (1 ml) was added and the reaction stirred at room temperature for 18 hours. The reaction mixture was diluted with dichloromethane and the solution was washed with saturated sodium hydrogen carbonate solution, water and brine, dried and evaporated. The residue was purified by silica gel chromatography eluting with 0-10% methanol in dichloromethane. The residue was triturated with ether and the resulting solid was collected and dried to give N-{[2-chloro-3-(trifluoromethyl)phenyl]methyl}-1-(2,6-dimethyl-3-pyridinyl)-3-methyl-2-oxo-4-imidazolidinecarboxamide (104 mg, 47%). LC/MS [M+H]⁺=441, retention time=1.86 minutes.

The 1-(2,6-dimethyl-3-pyridinyl)-3-methyl-2-oxo-4-imidazolidinecarboxylic acid TFA salt used in the method described above was prepared as follows:

(i) A solution of 1,1-dimethylethyl 3-methyl-2-oxo-4-imidazolidinecarboxylate (600 mg, 3.00 mmol) (prepared as described in step (iii) of Example 13, starting from (4S)-2-oxo-3-{[(phenylmethyl)oxy]carbonyl}-4-imidazolidinecarboxylic acid) and 3-bromo-2,6-dimethylpyridine (557 mg, 3.00 mmol) in 1,4-dioxane (20 ml) was treated with cesium carbonate (1464 mg, 4.49 mmol), Xantphos™ (130 mg, 0.225 mmol) and tris(dibenzylideneacetone)dipalladium(0) (68.6 mg, 0.075 mmol) and the mixture was heated at reflux under argon for 3 hours. After cooling to room temperature, the reaction mixture was diluted with water and extracted with ethyl acetate. The organic layers were combined, washed with water and brine and evaporated in vacuo. The residue was purified by silica gel chromatography eluting with 0-10% methanol in dichloromethane. The residue was dissolved in methanol and applied to a SCX ion exchange cartridge and washed with methanol and then 2M ammonia in methanol. The basic fractions were combined and evaporated Examples 55-56

In forms obtainable or prepared from (4S)-2-oxo-3-{[(phenylmethyl)oxy]carbonyl}-4-imidazolidinecarboxylic acid)

In a manner analogous to that described for Example 54 above the compounds tabulated below (Table 9) were prepared by substituting the appropriate amine (or salt thereof) for the {[2-chloro-3-(trifluoromethyl)phenyl]methyl}amine used in the above procedure. All of the amines used in Table 9 are available from commercial sources or can be prepared using routes described previously in the chemical literature or analogous methods.

TABLE 9

| Example no. | Chemical name | [M + H]+ | Retention time (mins) |
|---|---|---|---|
| E55 | 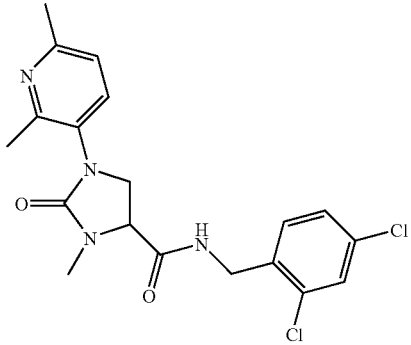<br>N-[(2,4-Dichlorophenyl)methyl]-1-(2,6-dimethyl-3-pyridinyl)-3-methyl-2-oxo-4-imidazolidinecarboxamide | 407 | 1.77 |
| 56 | 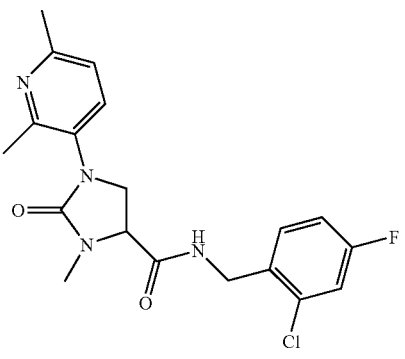<br>N-[(2-Chloro-4-fluorophenyl)methyl]-1-(2,6-dimethyl-3-pyridinyl)-3-methyl-2-oxo-4-imidazolidinecarboxamide | 391 | 1.61 | to give 1,1-dimethylethyl 1-(2,6-dimethyl-3-pyridinyl)-3-methyl-2-oxo-4-imidazolidinecarboxylate (493 mg, 54%). LC/MS [M+H]+=306.

(ii) A solution of 1,1-dimethylethyl 1-(2,6-dimethyl-3-pyridinyl)-3-methyl-2-oxo-4-imidazolidinecarboxylate (0.489 g, 1.6 mmol) in TFA/DCM (1:2, 9 ml) was stirred at room temperature for 16 hours. The solution was evaporated and the residue was co-evaporated with toluene and dried to give crude 1-(2,6-dimethyl-3-pyridinyl)-3-methyl-2-oxo-4-imidazolidinecarboxylic acid TFA salt, (assume ~1.6 mmol) which was used in the next step. LC/MS [M+H]+=250.

Example 57

N-{[2-Chloro-3-(trifluoromethyl)phenyl]methyl}-3-methyl-1-(1-methyl-1H-imidazol-4-yl)-2-oxo-4-imidazolidinecarboxamide (E57) (in a form obtainable or prepared from (4S)-2-oxo-3-{[(phenylmethyl)oxy]carbonyl}-4-imidazolidinecarboxylic acid)

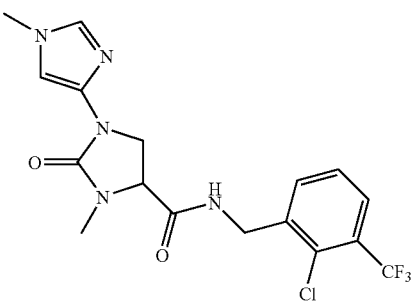

A solution of 3-methyl-1-(1-methyl-1H-imidazol-4-yl)-2-oxo-4-imidazolidinecarboxylic acid trifluoroacetate salt (145 mg, 0.647 mmol) in dichloromethane (4 ml) was treated with 1-hydroxyorthobenzatriazole hydrate (119 mg, 0.776 mmol), 1-ethyl-3-(3-dimethylaminopropyl)carbodiimide hydrochloride (149 mg, 0.776 mmol) & N-ethylmorpholine (0.491 ml, 3.88 mmol) and the mixture stirred at room temp for 10 minutes. 1-{[2-Chloro-3-(trifluoromethyl)phenyl]methyl}amine (136 mg, 0.647 mmol) was then added and the reaction stirred at room temp over the weekend. The reaction was diluted with dichloromethane and washed with 3N citric acid, saturated sodium hydrogen carbonate solution, water and brine, separated through a hydrophobic frit and the organic layer reduced under vacuum. The residue was purified by mass-directed automated HPLC and freeze dried to give N-{[2-chloro-3-(trifluoromethyl)phenyl]methyl}-3-methyl-1-(1-methyl-1H-imidazol-4-yl)-2-oxo-4-imidazolidinecarboxamide (30 mg, 10.6% yield). LC/MS [M+H]$^+$=416, retention time=1.92 minutes.

The 3-methyl-1-(1-methyl-1H-imidazol-4-yl)-2-oxo-4-imidazolidinecarboxylic acid trifluoroacetate salt used in the method described above was prepared as follows:
(i) To a stirred mixture of 1,1-dimethylethyl 3-methyl-2-oxo-4-imidazolidinecarboxylate (200 mg, 0.999 mmol) (prepared as described in step (iii) of Example 13, starting from (4S)-2-oxo-3-{[(phenylmethyl)oxy]carbonyl}-4-imidazolidinecarboxylic acid) and 4-bromo-1-methyl-1H-imidazole (193 mg, 1.199 mmol) in 1,4-dioxane (8 ml) was added potassium phosphate (1060 mg, 4.99 mmol), copper(I) iodide (190 mg, 0.999 mmol) and trans-N,N-dimethylcyclohexane-1,2-diamine (0.158 ml, 0.999 mmol) and the reaction mixture was stirred at reflux under argon for 3 hours. The mixture was cooled to room temperature and diluted with dichloromethane (20 mL) and filtered and washed through with dichloromethane. The filtrate was concentrated under vacuum and taken up in dichloromethane. The solution was washed with 0.880 ammonia (×3), water then brine and separated by hydrophobic frit and the organic layer was reduced under vacuum. The residue was purified by Flashmaster automated silica gel chromatography eluting with 0-20% methanol in dichloromethane to leave an oil which crystallised on standing. The residue was dried under vacuum overnight to give 1,1-dimethylethyl 3-methyl-1-(1-methyl-1H-imidazol-4-yl)-2-oxo-4-imidazolidinecarboxylate (285 mg, 87% yield). LC/MS [M+H]$^+$=281.

(ii) Trifluoroacetic acid (1.0 ml, 12.98 mmol) was added to a solution of 1,1-dimethylethyl 3-methyl-1-(1-methyl-1H-imidazol-4-yl)-2-oxo-4-imidazolidinecarboxylate (220 mg, 0.785 mmol) in DCM (2 ml) and the reaction mixture was stirred at room temperature for 5 hours. The solvent was evaporated under vacuum, azeotroping with toluene and the residue was dried under vacuum over the weekend to give crude 3-methyl-1-(1-methyl-1H-imidazol-4-yl)-2-oxo-4-imidazolidinecarboxylic acid trifluoroacetate salt which was taken through to next step without further purification. LC/MS [M+H]$^+$=225.

Example 58

N-[(2,4-Dichlorophenyl)methyl]-3-methyl-1-(1-methyl-1H-imidazol-4-yl)-2-oxo-4-imidazolidinecarboxamide (E58) (in a form obtainable or prepared from (4S)-2-oxo-3-{[(phenylmethyl)oxy]carbonyl}-4-imidazolidinecarboxylic acid)

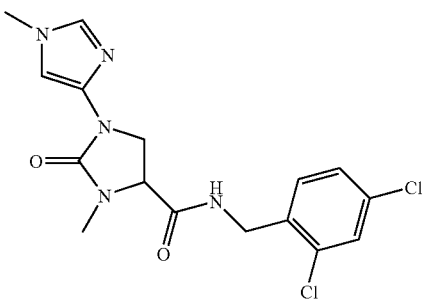

A solution of 3-methyl-1-(1-methyl-1H-imidazol-4-yl)-2-oxo-4-imidazolidinecarboxylic acid trifluoroacetate salt (0.105 g, 0.47 mmol) (prepared as described in step (ii) of Example 57) and N-ethyl morpholine (0.361 ml, 2.82 mmol) in dichloromethane (5 ml) was treated with 1-hydroxybenzotriazole hydrate (0.086 g, 0.564 mmol) and 1-ethyl-3-(3-dimethylaminopropyl)carbodiimide hydrochloride (0.090 g, 0.470 mmol) and stirred at room temperature for 10 minutes. 1-(2,4-Dichlorophenyl)methanamine (0.063 ml, 0.470 mmol) was added and the reaction mixture was stirred over the weekend. The reaction mixture was diluted with dichloromethane and washed with saturated sodium hydrogen carbonate solution, water and brine and separated using a hydrophobic frit. The filtrate was concentrated under vacuum and purified by mass-directed automated HPLC to give N-[(2,4-dichlorophenyl)methyl]-3-methyl-1-(1-methyl-1H-imidazol-4-yl)-2-oxo-4-imidazolidinecarboxamide (26 mg, 13.75% yield). LC/MS [M+H]⁺=382, retention time=1.83 minutes.

Example 59

N-{[2-Chloro-3-(trifluoromethyl)phenyl]methyl}-3-methyl-1-(1-methyl-1H-imidazol-2-yl)-2-oxo-4-imidazolidinecarboxamide (E59) (in a form obtainable or prepared from (4S)-2-oxo-3-{[(phenylmethyl)oxy]carbonyl}-4-imidazolidinecarboxylic acid)

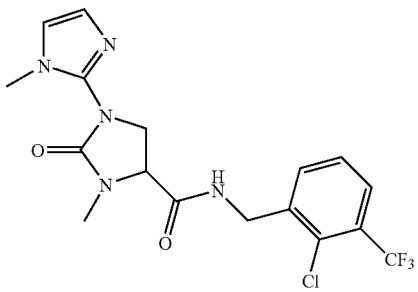

A solution of 3-methyl-1-(1-methyl-1H-imidazol-2-yl)-2-oxo-4-imidazolidinecarboxylic acid (166 mg, 0.517 mmol) and N-ethyl morpholine (0.397 ml, 3.10 mmol) in dichloromethane (5 ml) was treated with 1-hydroxybenzotriazole hydrate (95 mg, 0.620 mmol) and 1-ethyl-3-(3-dimethylaminopropyl)carbodiimide hydrochloride (99 mg, 0.517 mmol) and stirred at room temperature for 10 minutes. 1-[2-Chloro-3-(trifluoromethyl)phenyl]methanamine (108 mg, 0.517 mmol) was then added and the reaction stirred overnight at room temperature. The reaction mixture was diluted with dichloromethane and washed with saturated sodium hydrogen carbonate solution, water and brine, separated through a hydrophobic frit and the organic layer was reduced under vacuum. The residue was purified by mass-directed automated HPLC to give N-{[2-chloro-3-(trifluoromethyl)phenyl]methyl}-3-methyl-1-(1-methyl-1H-imidazol-2-yl)-2-oxo-4-imidazolidinecarboxamide (67 mg, 29.6% yield). LC/MS [M+H]⁺=416, retention time=1.89 minutes.

The 3-methyl-1-(1-methyl-1H-imidazol-2-yl)-2-oxo-4-imidazolidinecarboxylic acid used in the method described above was prepared as follows:
(i) To a stirred solution of 1,1-dimethylethyl 3-methyl-2-oxo-4-imidazolidinecarboxylate (0.200 g, 1.00 mmol) (prepared as described in step (iii) of Example 13, starting from (4S)-2-oxo-3-{[(phenylmethyl)oxy]carbonyl}-4-imidazolidinecarboxylic acid) and 2-bromo-1-methyl-1H-imidazole (0.146 ml, 1.500 mmol) in 1,4-dioxane (8 ml) was added potassium phosphate (1.062 g, 5.00 mmol), copper(I) iodide (0.190 g, 1.000 mmol) and trans-N,N-dimethylcyclohexane-1,2-diamine (0.155 ml, 1.000 mmol) and the mixture heated at reflux under argon overnight. The mixture was cooled to room temperature and diluted with dichloromethane. The solid was filtered off, washed with dichloromethane and the filtrate reduced under vacuum. The residue was re-dissolved in dichloromethane and washed with 0.880 ammonia solution (×2), water then brine and passed through a hydrophobic frit and the organic layer reduced under vacuum. The residue was purified by Flashmaster automated silica gel chromatography eluting with 0-10% methanol in dichloromethane to give 1,1-dimethylethyl 3-methyl-1-(1-methyl-1H-imidazol-2-yl)-2-oxo-4-imidazolidinecarboxylate (145 mg, 37.8% yield). LC/MS [M+H]⁺=281.
(ii) Trifluoroacetic acid (0.059 ml, 0.517 mmol) was added to a solution of 1,1-dimethylethyl 3-methyl-1-(1-methyl-1H-imidazol-2-yl)-2-oxo-4-imidazolidinecarboxylate (145 mg, 0.517 mmol) in DCM (2 ml) and the reaction stirred at room temperature overnight. The reaction mixture was co-evaporated with toluene and dried to give 3-methyl-1-(1-methyl-1H-imidazol-2-yl)-2-oxo-4-imidazolidinecarboxylic acid (assume ~0.517 mmol) which was used which was used in the next step. LC/MS [M+H]⁺=225.

Example 60

N-[(2,4-Dichlorophenyl)methyl]-3-methyl-1-(1-methyl-1H-imidazol-5-yl)-2-oxo-4-imidazolidinecarboxamide (E60) (in a form obtainable or prepared from (4S)-2-oxo-3-{[(phenylmethyl)oxy]carbonyl}-4-imidazolidinecarboxylic acid)

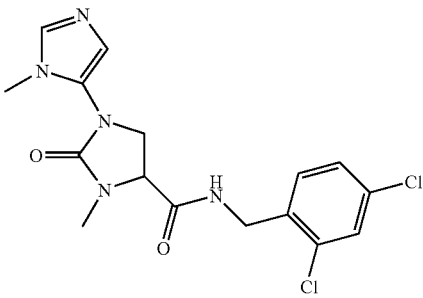

A solution of 3-methyl-1-(1-methyl-1H-imidazol-5-yl)-2-oxo-4-imidazolidinecarboxylic acid (155 mg, 0.458 mmol) and N-ethylmorpholine (0.348 ml, 2.75 mmol) in dichloromethane (5 ml) was treated with 1-hydroxybenzotriazole hydrate (84 mg, 0.550 mmol) and 1-ethyl-3-(3-dimethylaminopropyl)carbodiimide hydrochloride (88 mg, 0.458 mmol) and stirred at room temperature for 10 minutes. 1-(2,4-Dichlorophenyl)methanamine (81 mg, 0.458 mmol) was then added and the reaction mixture was stirred at room temperature for 6 hours. The reaction mixture was diluted with dichloromethane and washed with saturated sodium hydrogen carbonate solution, water and brine, separated through a hydrophobic frit and the organic layer reduced under vacuum. The residue was purified by mass-directed automated HPLC to give N-[(2,4-dichlorophenyl)methyl]-3-methyl-1-(1-methyl-1H-imidazol-5-yl)-2-oxo-4-imidazolidinecarboxamide (63 mg, 34.2% yield). LC/MS [M+H]⁺=382, retention time=1.71 minutes.

The 3-methyl-1-(1-methyl-1H-imidazol-2-yl)-2-oxo-4-imidazolidinecarboxylic acid used in the method described above was prepared as follows:
(i) To a stirred solution of 1,1-dimethylethyl 3-methyl-2-oxo-4-imidazolidinecarboxylate (801 mg, 4.00 mmol) (prepared as described in step (iii) of Example 13, starting from (4S)-2-oxo-3-{[(phenylmethyl)oxy]carbonyl}-4-imidazolidinecarboxylic acid) and 5-bromo-1-methylimidazole (644 mg, 4.00 mmol) in 1,4-dioxane (30 ml) was added potassium phosphate (4246 mg, 20.00 mmol), trans-N,N-dimethylcyclohexane-1,2-diamine (0.631 ml, 4.00 mmol) and copper(I) iodide (762 mg, 4.00 mmol) and the mixture stirred at reflux overnight. The reaction mixture was diluted with dichloromethane and filtered through celite. The filter pad was washed with dichloromethane and the filtrate was reduced under vacuum. The residue was re-dissolved in dichloromethane, washed with 0.880 ammonia (×2), water then brine and passed through a hydrophobic frit and the solution was concentrated under vacuum. The residue was purified by Flashmaster automated silica gel chromatography eluting with 0-10% methanol in dichloromethane to give 1,1-dimethylethyl 3-methyl-1-(1-methyl-1H-imidazol-5-yl)-2-oxo-4-imidazolidinecarboxylate (393 mg, 32.6% yield). LC/MS [M+H]⁺=281.

(ii) Trifluoroacetic acid (2 ml) was added to a solution of 1,1-dimethylethyl (4S)-3-methyl-1-(1-methyl-1H-imidazol-5-yl)-2-oxo-4-imidazolidinecarboxylate (390 mg, 1.391 mmol) in dichloromethane (4 ml) and stirred at room temperature for 2 hours, then allowed to stand overnight. The solvent was evaporated and the residue was co-evaporated with toluene and dried under heated vacuum (40° C.) overnight to give 3-methyl-1-(1-methyl-1H-imidazol-5-yl)-2-oxo-4-imidazolidinecarboxylic acid TFA salt (assume ~1.4 mmol) which was used which was used in the next step. LC/MS [M+H]⁺=225.

Example 61

N-{[2-Chloro-3-(trifluoromethyl)phenyl]methyl}-3-methyl-1-(1-methyl-1H-imidazol-5-yl)-2-oxo-4-imidazolidinecarboxamide (E61) (in a form obtainable or prepared from (4S)-2-oxo-3-{[(phenylmethyl)oxy]carbonyl}-4-imidazolidinecarboxylic acid)

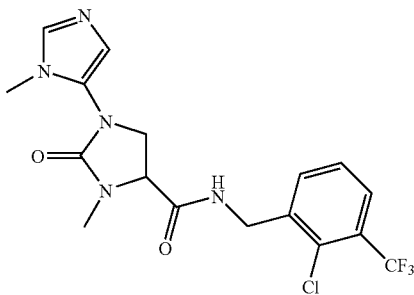

In a manner analogous to that described in Example 60 above N-{[2-chloro-3-(trifluoromethyl)phenyl]methyl}-3-methyl-1-(1-methyl-1H-imidazol-5-yl)-2-oxo-4-imidazolidinecarboxamide was prepared substituting 1-(2,4-dichlorophenyl)methanamine for the {[2-chloro-3-(trifluoromethyl)phenyl]methyl}amine used in the above procedure. LC/MS [M+H]⁺=416, retention time=1.75 minutes.

Example 62

N-[(2-Chloro-3,4-difluorophenyl)methyl]-3-methyl-2-oxo-1-[6-(trifluoromethyl)-4-pyrimidinyl]-4-imidazolidinecarboxamide (E62) (in a form obtainable or prepared from (4S)-2-oxo-3-{[(phenylmethyl)oxy]carbonyl}-4-imidazolidinecarboxylic acid)

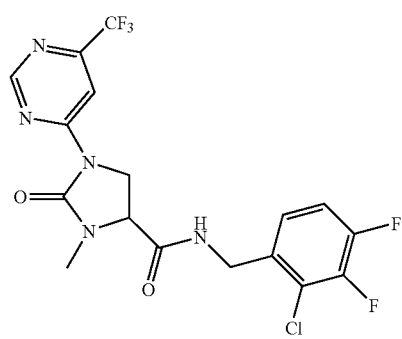

To a suspension of 3-methyl-2-oxo-1-[6-(trifluoromethyl)-4-pyrimidinyl]-4-imidazolidinecarboxylic acid (200 mg, 0.612 mmol) and N-ethylmorpholine (0.465 ml, 3.67 mmol) in dichloromethane (10 ml)/DMF (1 ml) was added 1-hydroxybenzotriazole hydrate (113 mg, 0.735 mmol) and 1-ethyl-3-(3-dimethylaminopropyl)carbodiimide hydrochloride (117 mg, 0.612 mmol) and the reaction mixture was stirred for 1 hour at room temperature. 1-(2-Chloro-3,4-difluorophenyl)methanamine (131 mg, 0.612 mmol) was then added and the reaction stirred overnight. Additional 1-ethyl-3-(3-dimethylaminopropyl)carbodiimide hydrochloride (117 mg, 0.612 mmol) was added and the reaction mixture was stirred for 3 hours. The reaction mixture was diluted with dichloromethane and washed with saturated sodium hydrogen carbonate solution, water, 3N citric acid solution, water then brine and separated through a hydrophobic frit and the organic layer concentrated under vacuum. The residue was purified by SP4 automated silica gel chromatography eluting with 10-100% ethyl acetate in isohexane to give N-[(2-chloro-3,4-difluorophenyl)methyl]-3-methyl-2-oxo-1-[6-(trifluoromethyl)-4-pyrimidinyl]-4-imidazolidinecarboxamide (95 mg, 33.8% yield). LC/MS [M+H]⁺=450, retention time=2.93 minutes.

The 3-methyl-2-oxo-1-[6-(trifluoromethyl)-4-pyrimidinyl]-4-imidazolidinecarboxylic acid used in the method described above was prepared as follows:

(i) A solution of 1,1-dimethylethyl 3-methyl-2-oxo-4-imidazolidinecarboxylate (800 mg, 4.00 mmol) (prepared as described in step (iii) of Example 13, starting from (4S)-2-oxo-3-{[(phenylmethyl)oxy]carbonyl}-4-imidazolidinecarboxylic acid) and 4-chloro-6-(trifluoromethyl)pyrimidine (729 mg, 4.00 mmol) in 1,4-dioxane (40 ml) was treated with cesium carbonate (1953 mg, 5.99 mmol), Xantphos™ (173 mg, 0.300 mmol) and tris(dibenzylideneacetone)dipalladium (0) (91 mg, 0.100 mmol) and the reaction mixture was heated at reflux under argon overnight. After cooling the reaction was diluted with water and extracted with ethyl acetate (×2). The organic layers were combined and washed with water and brine, dried over anhydrous sodium sulfate and reduced under vacuum. The residue was purified by Flashmaster automated silica gel chromatography eluting with 0-30% ethyl acetate in isohexane to give 1,1-dimethylethyl 3-methyl-2-oxo-1-[6-(trifluoromethyl)-4-pyrimidinyl]-4-imidazolidinecarboxylate (983 mg, 67.5% yield). LC/MS [M+H]$^+$=347.

(ii) Trifluoroacetic acid (4 ml, 51.9 mmol) was added to a solution of 1,1-dimethylethyl 3-methyl-2-oxo-1-[6-(trifluoromethyl)-4-pyrimidinyl]-4-imidazolidinecarboxylate (980 mg, 2.83 mmol) in dichloromethane (8 ml) and the solution was stirred at room temperature for 6 hours. The solvent was evaporated and the residue was co-evaporated with toluene. The residue was dissolved in saturated sodium hydrogen carbonate solution and the solution was loaded onto an amino column eluting with 10% 2N hydrochloric acid in methanol. Product-containing fractions were combined and reduced under vacuum and the residue was triturated with methanol and the solid was filtered off. The filtrate was reduced under vacuum to give 3-methyl-2-oxo-1-[6-(trifluoromethyl)-4-pyrimidinyl]-4-imidazolidinecarboxylic acid hydrochloride salt (893 mg, assume ~2.8 mmol) which was used in the next step. LC/MS [M+H]$^+$=291.

Examples 63-64

In forms obtainable or prepared from (4S)-2-oxo-3-{[(phenylmethyl)oxy]carbonyl}-4-imidazolidinecarboxylic acid In a manner analogous to that described for Example 62 above the compounds tabulated below (Table 10) were prepared by substituting the appropriate amine (or salt thereof) for the 1-(2-chloro-3,4-difluorophenyl)methanamine used in the above procedure. All of the amines used in Table 10 are available from commercial sources or can be prepared using routes described previously in the chemical literature or analogous methods.

TABLE 10

| Example no. | Chemical name | [M + H]$^+$ | Retention time (mins) |
|---|---|---|---|
| E63 | 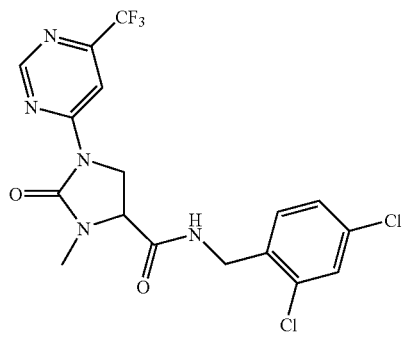<br>N-[(2,4-Dichlorophenyl)methyl]-3-methyl-2-oxo-1-[6-(trifluoromethyl)-4-pyrimidinyl]-4-imidazolidinecarboxamide | 448 | 3.04 |
| E64 | 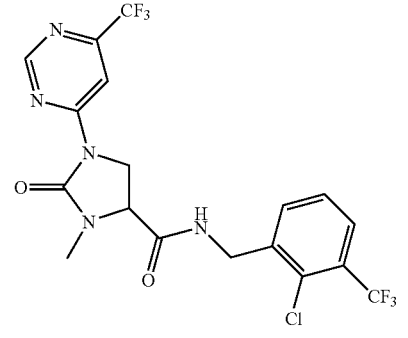<br>N-{[2-Chloro-3-(trifluoromethyl)phenyl]methyl}-3-methyl-2-oxo-1-[6-(trifluoromethyl)-4-pyrimidinyl]-4-imidazolidinecarboxamide | 482 | 3.08 |

Example 65

N-[(2,4-Dichlorophenyl)methyl]-1-(6-fluoro-3-pyridinyl)-3-methyl-2-oxo-4-imidazolidinecarboxamide (E65) (in a form obtainable or prepared from (4S)-2-oxo-3-{[(phenylmethyl)oxy]carbonyl}-4-imidazolidinecarboxylic acid)

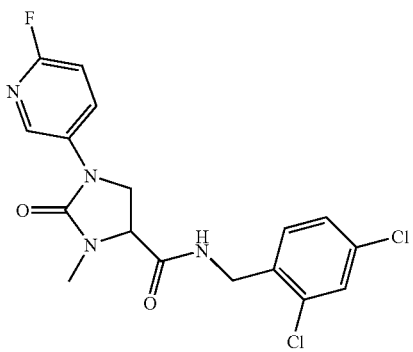

To a solution of 1-(6-fluoro-3-pyridinyl)-3-methyl-2-oxo-4-imidazolidinecarboxylic acid TFA salt (200 mg, 0.836 mmol) and N-ethylmorpholine (0.635 ml, 5.02 mmol) in dichloromethane (10 ml) was added 1-hydroxybenzotriazole hydrate (128 mg, 0.836 mmol) and 1-ethyl-3-(3-dimethylaminopropyl)carbodiimide hydrochloride (160 mg, 0.836 mmol) and the mixture was stirred for 10 minutes. 1-(2,4-Dichlorophenyl)methanamine (147 mg, 0.836 mmol) was added and the reaction stirred at room temperature overnight. The reaction mixture was diluted with dichloromethane and washed with saturated sodium hydrogen carbonate solution, water and brine, separated through a hydrophobic frit and the organic layer was reduced under vacuum. The residue was purified by FFlashmaster automated silica gel chromatography eluting with 10-100% ethyl acetate in isohexane to give N-[(2,4-dichlorophenyl)methyl]-1-(6-fluoro-3-pyridinyl)-3-methyl-2-oxo-4-imidazolidinecarboxamide (60 mg, 18% yield). LC/MS $[M+H]^+$=397, retention time=2.63 minutes.

The 1-(6-fluoro-3-pyridinyl)-3-methyl-2-oxo-4-imidazolidinecarboxylic acid TFA salt used in the method described above was prepared as follows:
(i) To a solution of 1,1-dimethylethyl 3-methyl-2-oxo-4-imidazolidinecarboxylate (400 mg, 1.998 mmol) (prepared as described in step (iii) of Example 13, starting from (4S)-2-oxo-3-{[(phenylmethyl)oxy]carbonyl}-4-imidazolidinecarboxylic acid) and 5-bromo-2-fluoropyridine (352 mg, 1.998 mmol) in 1,4-dioxane (20 ml) was added trans-N,N-dimethylcyclohexane-1,2-diamine (0.062 ml, 0.400 mmol), potassium phosphate (1272 mg, 5.99 mmol) and copper(I) iodide (38.0 mg, 0.200 mmol) and the reaction mixture was heated at reflux under argon overnight. The reaction mixture was allowed to cool and the solvent was evaporated. The residue was partitioned between dichloromethane and water. The organic layer was separated and washed with water (~50 ml) containing 0.880 ammonia solution (~5 ml), then brine and passed through a hydrophobic frit and the organic layer was reduced under vacuum. The residue was purified by SP4 automated silica gel chromatography eluting with 10-80% ethyl acetate in isohexane to give 1,1-dimethylethyl 1-(6-fluoro-3-pyridinyl)-3-methyl-2-oxo-4-imidazolidinecarboxylate (422 mg, 68.7% yield). LC/MS $[M+H]^+$=296.

(ii) Trifluoroacetic acid (2 ml) was added to a solution of 1,1-dimethylethyl 1-(6-fluoro-3-pyridinyl)-3-methyl-2-oxo-4-imidazolidinecarboxylate (420 mg, 1.422 mmol) in dichloromethane (5 ml) and the mixture was stirred at room temperature for 36 hours. The reaction mixture was reduced under vacuum and the residue was azeotroped with toluene and dried under heated vacuum to give 1-(6-fluoro-3-pyridinyl)-3-methyl-2-oxo-4-imidazolidinecarboxylic acid TFA salt (assume ~1.4 mmol) which was used in the next step. LC/MS $[M+H]^+$=240.

Example 66

N-{[2-Chloro-3-(trifluoromethyl)phenyl]methyl}-1-(6-fluoro-3-pyridinyl)-3-methyl-2-oxo-4-imidazolidinecarboxamide (E66) (in a form obtainable or prepared from (4S)-2-oxo-3-{[(phenylmethyl)oxy]carbonyl}-4-imidazolidinecarboxylic acid)

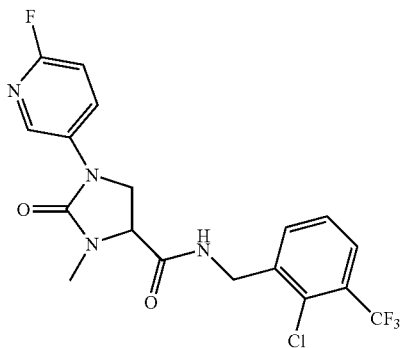

In a manner analogous to that described in Example 65 above N-{[2-chloro-3-(trifluoromethyl)phenyl]methyl}-1-(6-fluoro-3-pyridinyl)-3-methyl-2-oxo-4-imidazolidinecarboxamide was prepared substituting {[2-chloro-3-(trifluoromethyl)phenyl]methyl}amine for the 1-(2,4-dichlorophenyl)methanamine used in the above procedure. LC/MS $[M+H]^+$=431, retention time=2.69 minutes.

Example 67

N-[(2,4-Dichlorophenyl)methyl]-1-(2-fluoro-3-pyridinyl)-3-methyl-2-oxo-4-imidazolidinecarboxamide (E67) (in a form obtainable or prepared from (4S)-2-oxo-3-{[(phenylmethyl)oxy]carbonyl}-4-imidazolidinecarboxylic acid)

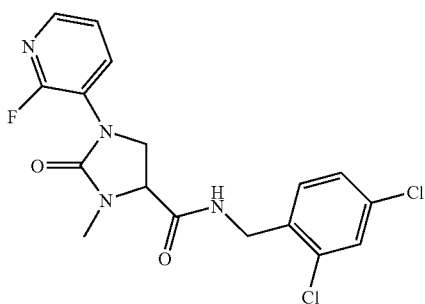

To a solution of 1-(2-fluoro-3-pyridinyl)-3-methyl-2-oxo-4-imidazolidinecarboxylic acid TFA salt (182 mg, 0.761 mmol) and N-ethylmorpholine (0.578 ml, 4.57 mmol) in dichloromethane (5 ml) was added 1-hydroxybenzotriazole hydrate (117 mg, 0.761 mmol) and 1-ethyl-3-(3-dimethylaminopropyl)carbodiimide hydrochloride (146 mg, 0.761 mmol) and the reaction mixture was stirred for 10 minutes at room temperature. 1-(2,4-Dichlorophenyl)methanamine (134 mg, 0.761 mmol) was added and the reaction was stirred at room temperature overnight. The reaction mixture was diluted with dichloromethane and the solution was washed with saturated sodium hydrogen carbonate solution, water and brine, separated through a hydrophobic frit and the organic layer was reduced under vacuum. The residue was purified by SP4 automated silica gel chromatography eluting with 10-100% ethyl acetate in isohexane to give N-[(2,4-dichlorophenyl)methyl]-1-(2-fluoro-3-pyridinyl)-3-methyl-2-oxo-4-imidazolidinecarboxamide (125 mg, 40.5% yield)

LC/MS [M+H]$^+$=397, retention time=2.51 minutes.

The 1-(2-fluoro-3-pyridinyl)-3-methyl-2-oxo-4-imidazolidinecarboxylic acid TFA salt used in the method described above was prepared as follows:

(i) To a solution of 1,1-dimethylethyl 3-methyl-2-oxo-4-imidazolidinecarboxylate (400 mg, 1.998 mmol) (prepared as described in step (iii) of Example 13, starting from (4S)-2-oxo-3-{[(phenylmethyl)oxy]carbonyl}-4-imidazolidinecarboxylic acid) and 2-fluoro-3-iodopyridine (352 mg, 1.998 mmol) in 1,4-dioxane (20 ml) was added trans-N,N-dimethylcyclohexane-1,2-diamine (0.062 ml, 0.400 mmol), potassium phosphate (1272 mg, 5.99 mmol) and copper(I) iodide (38.0 mg, 0.200 mmol) and the reaction mixture was heated at reflux under argon overnight. The reaction mixture was allowed to cool and the solvent was evaporated. The residue was partitioned between dichloromethane and water. The organic layer was separated and washed with water (~50 ml) containing 0.880 ammonia solution (~5 ml), then brine and passed through a hydrophobic frit and the organic layer was reduced under vacuum. The residue was purified by SP4 automated silica gel chromatography eluting with 10-80% ethyl acetate in isohexane to give 1,1-dimethylethyl 1-(2-fluoro-3-pyridinyl)-3-methyl-2-oxo-4-imidazolidinecarboxylate (405 mg, 67.3% yield). LC/MS [M+H]$^+$=296.

(ii) Trifluoroacetic acid (2 ml) was added to a solution of 1,1-dimethylethyl (4S)-1-(2-fluoro-3-pyridinyl)-3-methyl-2-oxo-4-imidazolidinecarboxylate (400 mg, 1.355 mmol) in dichloromethane (5 ml) and the solution was stirred at room temperature for 36 hours. The reaction mixture was reduced under vacuum and the residue was azeotroped with toluene and dried under heated vacuum to give 1-(2-fluoro-3-pyridinyl)-3-methyl-2-oxo-4-imidazolidinecarboxylic acid TFA salt (assume ~1.35 mmol) which was used in the next step. LC/MS [M+H]$^+$=240.

Example 68

N-{[2-Chloro-3-(trifluoromethyl)phenyl]methyl}-1-(2-fluoro-3-pyridinyl)-3-methyl-2-oxo-4-imidazolidinecarboxamide (E68) (in a form obtainable or prepared from (4S)-2-oxo-3-{[(phenylmethyl)oxy]carbonyl}-4-imidazolidinecarboxylic acid)

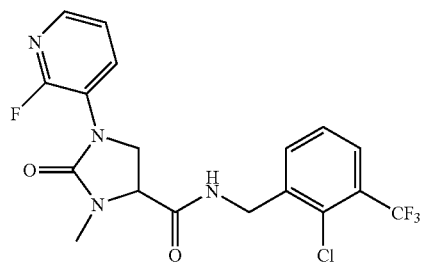

In a manner analogous to that described in Example 65 above N-{[2-chloro-3-(trifluoromethyl)phenyl]methyl}-1-(2-fluoro-3-pyridinyl)-3-methyl-2-oxo-4-imidazolidinecarboxamide was prepared substituting {[2-chloro-3-(trifluoromethyl)phenyl]methyl}amine for the 1-(2,4-dichlorophenyl)methanamine used in the above procedure. LC/MS [M+H]$^+$=431, retention time=2.56 minutes.

Example 69

N-[(2,4-Dichlorophenyl)methyl]-3-methyl-1-[6-(methyloxy)-3-pyridinyl]-2-oxo-4-imidazolidinecarboxamide (E69) (in a form obtainable or prepared from (4S)-2-oxo-3-{[(phenylmethyl)oxy]carbonyl}-4-imidazolidinecarboxylic acid)

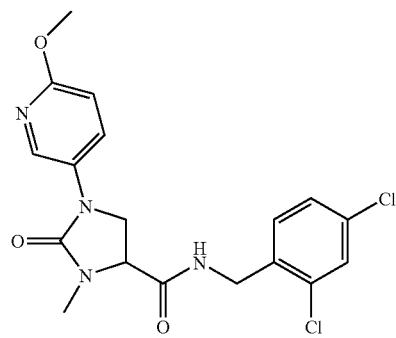

To a solution of 3-methyl-1-[6-(methyloxy)-3-pyridinyl]-2-oxo-4-imidazolidinecarboxylic acid TFA salt (145 mg, 0.404 mmol) and N-ethylmorpholine (0.307 ml, 2.424 mmol) in dichloromethane (5 ml) was added 1-hydroxybenzotriazole hydrate (61.9 mg, 0.404 mmol) and 1-ethyl-3-(3-dimethylaminopropyl)carbodiimide hydrochloride (77 mg, 0.404 mmol) and the reaction mixture was stirred for 10 minutes at room temperature. 1-(2,4-Dichlorophenyl)methanamine (71.1 mg, 0.404 mmol) was added and the reaction was stirred at room temperature overnight. The reaction mixture was diluted with dichloromethane and the solution was washed with saturated sodium hydrogen carbonate solution, water and brine, separated through a hydrophobic frit and the organic layer was reduced under vacuum. The residue was purified by SP4 automated silica gel chromatography eluting with 10-100% ethyl acetate in isohexane to give N-[(2,4-dichlorophenyl)methyl]-3-methyl-1-[6-(methyloxy)-3-pyridinyl]-2-oxo-4-imidazolidinecarboxamide (101 mg, 59.9% yield). LC/MS $[M+H]^+=409$, retention time=2.34 minutes.

The 1-(2-fluoro-3-pyridinyl)-3-methyl-2-oxo-4-imidazolidinecarboxylic acid TFA salt used in the method described above was prepared as follows:

(i) To a solution of 1,1-dimethylethyl 3-methyl-2-oxo-4-imidazolidinecarboxylate (400 mg, 1.998 mmol) (prepared as described in step (iii) of Example 13, starting from (4S)-2-oxo-3-{[(phenylmethyl)oxy]carbonyl}-4-imidazolidinecarboxylic acid) and 5-bromo-2-(methyloxy)pyridine (0.259 ml, 1.998 mmol) in 1,4-dioxane (20 ml) was added cesium carbonate (2604 mg, 7.99 mmol), Xantphos™ (87 mg, 0.150 mmol) and tris(dibenzylideneacetone)dipalladium(0) (91 mg, 0.100 mmol) and the reaction was stirred at reflux overnight. After cooling the solvent was removed under vacuum and the residue was partitioned between dichloromethane and water. The organic layer was separated, washed with saturated sodium hydrogen carbonate solution, water and then brine and passed through a hydrophobic frit. The organic layer was reduced under vacuum and the residue was purified by Flashmaster automated silica gel chromatography eluting with 0-30% ethyl acetate in isohexane to give 1,1-dimethylethyl 3-methyl-1-[6-(methyloxy)-3-pyridinyl]-2-oxo-4-imidazolidinecarboxylate (272 mg, 43.4% yield). LC/MS $[M+H]^+=308$.

(ii) Trifluoroacetic acid (1 ml) was added to a solution of 1,1-dimethylethyl 3-methyl-1-[6-(methyloxy)-3-pyridinyl]-2-oxo-4-imidazolidinecarboxylate (270 mg, 0.878 mmol) in dichloromethane (2 ml) and the solution was stirred at room temperature overnight. The reaction mixture reduced to dryness under vacuum azeotroping with toluene and then dried under heated vacuum overnight to give 3-methyl-1-[6-(methyloxy)-3-pyridinyl]-2-oxo-4-imidazolidinecarboxylic acid TFA salt (assume ~0.88 mmol). LC/MS $[M+H]^+=252$.

Example 70

N-{[2-Chloro-3-(trifluoromethyl)phenyl]methyl}-3-methyl-1-[6-(methyloxy)-3-pyridinyl]-2-oxo-4-imidazolidinecarboxamide (E70) (in a form obtainable or prepared from (4S)-2-oxo-3-{[(phenylmethyl)oxy]carbonyl}-4-imidazolidinecarboxylic acid)

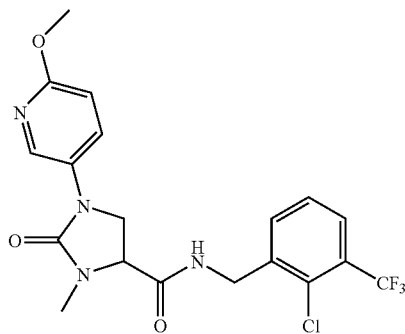

In a manner analogous to that described in Example 69 above N-{[2-chloro-3-(trifluoromethyl)phenyl]methyl}-3-methyl-1-[6-(methyloxy)-3-pyridinyl]-2-oxo-4-imidazolidinecarboxamide was prepared substituting {[2-chloro-3-(trifluoromethyl)phenyl]methyl}amine for the 1-(2,4-dichlorophenyl)methanamine used in the above procedure. LC/MS $[M+H]^+=443$, retention time=2.41 minutes.

Example 72

N-[(2,4-Dichlorophenyl)methyl]-1-methyl-2-oxo-3-(2,2,2-trifluoroethyl)-4-imidazolidinecarboxamide (E72) (in a form obtainable or prepared from (4S)-2-oxo-3-{[(phenylmethyl)oxy]carbonyl}-4-imidazolidinecarboxylic acid)

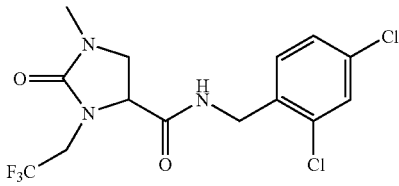

A mixture of 1-methyl-2-oxo-3-(2,2,2-trifluoroethyl)-4-imidazolidinecarboxylic acid (84 mg, 0.37 mmol), 1-hydroxybenzotriazole hydrate (68.0 mg, 0.444 mmol), 1-ethyl-3-(3-dimethylaminopropyl)carbodiimide hydrochloride (85 mg, 0.444 mmol) and N-ethyl morpholine (0.189 ml, 1.480 mmol) in dichloromethane (9 ml) was stirred at room temperature for 10 minutes. A solution of [1-(2,4-dichlorophenyl)methyl]amine (65.1 mg, 0.37 mmol) in dichloromethane (1 ml) was added and the reaction mixture was stirred at room temperature for 18 hours. The reaction mixture was diluted with dichloromethane (10 ml) and the solution was washed with saturated sodium hydrogen carbonate solution (10 ml), water (10 ml), citric acid solution (10 ml) and brine (10 ml), dried and evaporated. The residue was purified by mass-directed automated HPLC. The residue was triturated with ether and the resulting solid was collected and dried to give N-[(2,4-dichlorophenyl)methyl]-1-methyl-2-oxo-3-(2,2,2-trifluoroethyl)-4-imidazolidinecarboxamide (60 mg, 42%). LC/MS $[M+H]^+=384$, retention time=2.64 minutes.

The 1-methyl-2-oxo-3-(2,2,2-trifluoroethyl)-4-imidazolidinecarboxylic acid used in the method described above was prepared as follows:

(i) A solution of 1,1-dimethylethyl 1-methyl-2-oxo-4-imidazolidinecarboxylate (180 mg, 0.9 mmol) (prepared as described in step (i) of Example 49 from 5-(1,1-dimethylethyl)1-(phenylmethyl)3-methyl-2-oxo-1,5-imidazolidinedicarboxylate, itself prepared as described in step (ii) of Example 13, starting originally from (4S)-2-oxo-3-{[(phenylmethyl)oxy]carbonyl}-4-imidazolidinecarboxylic acid) in N,N-dimethylformamide (10 ml), under argon at −35° C., was treated with sodium hydride (60% dispersion in oil) (36.0 mg, 0.900 mmol). The mixture was stirred at −35° C. for 15 minutes and then 2,2,2-trifluoroethyl trichloromethanesulfonate (507 mg, 1.800 mmol) was added and the reaction mixture was stirred at −35° C. for 2 hours (the temperature increased slowly to −15° C.). The reaction was quenched with water (5 ml) and allowed to warm to room temperature and the reaction mixture was extracted with ethyl acetate (2×20 ml). The organic layer was separated, washed with saturated sodium hydrogen carbonate solution (10 ml), water (2×10 ml)

and brine (20 ml) and evaporated. The residue was purified by silica gel chromatography eluting with 10-100% ethyl acetate in isohexane to give 1,1-dimethylethyl 1-methyl-2-oxo-3-(2,2,2-trifluoroethyl)-4-imidazolidinecarboxylate (107 mg, 42%). LC/MS [M+H]$^+$=283.

(ii) A solution of 1,1-dimethylethyl 1-methyl-2-oxo-3-(2,2,2-trifluoroethyl)-4-imidazolidinecarboxylate (107 mg, 0.379 mmol) in TFA/DCM (1:2, 3 ml) was stirred at room temperature for 4 hours. The solution was evaporated and the residue was co-evaporated with dichloromethane and dried to give crude 1-methyl-2-oxo-3-(2,2,2-trifluoroethyl)-4-imidazolidinecarboxylic acid (assume ~0.38 mmol) which was used in the next reaction. LC/MS [M+H]$^+$=227.

Example 73

N-[(2,4-Dichlorophenyl)methyl]-3-ethyl-1-methyl-2-oxo-4-imidazolidinecarboxamide (E73) (in a form obtainable or prepared from (4S)-2-oxo-3-{[(phenylmethyl)oxy]carbonyl}-4-imidazolidinecarboxylic acid)

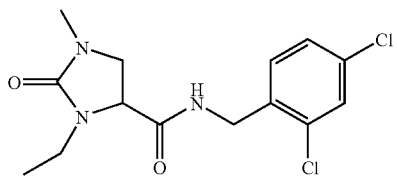

A mixture of 3-ethyl-1-methyl-2-oxo-4-imidazolidinecarboxylic acid (138 mg, 0.800 mmol), 1-hydroxybenzotriazole hydrate (147 mg, 0.960 mmol), 1-ethyl-3-(3-dimethylaminopropyl)carbodiimide hydrochloride (184 mg, 0.960 mmol) and N-ethyl morpholine (0.409 ml, 3.20 mmol) in dichloromethane (9 ml) was stirred at room temperature for 10 minutes. A solution of [1-(2,4-dichlorophenyl)methyl]amine (141 mg, 0.8 mmol) in dichloromethane (1 ml) was added and the reaction mixture was stirred at room temperature for 18 hours. The reaction mixture was diluted with dichloromethane (10 ml) and the solution was washed with saturated sodium hydrogen carbonate solution (10 ml), water (10 ml), citric acid solution (10 ml) and brine (10 ml), dried and evaporated. The residue was purified by mass-directed automated HPLC. The residue was triturated with ether and the resulting solid was collected and dried to give N-[(2,4-dichlorophenyl)methyl]-3-ethyl-1-methyl-2-oxo-4-imidazolidinecarboxamide (141 mg, 53%). LC/MS [M+H]$^+$=330, retention time=2.36 minutes.

The 3-ethyl-1-methyl-2-oxo-4-imidazolidinecarboxylic acid used in the method described above was prepared as follows:

(i) A stirred solution of 1,1-dimethylethyl 1-methyl-2-oxo-4-imidazolidinecarboxylate (0.501 g, 2.5 mmol) (prepared as described in step (i) of Example 49 from 5-(1,1-dimethylethyl)1-(phenylmethyl)3-methyl-2-oxo-1,5-imidazolidinedicarboxylate, itself prepared as described in step (ii) of Example 13, starting originally from (4S)-2-oxo-3-{[(phenylmethyl)oxy]carbonyl}-4-imidazolidinecarboxylic acid) in N,N-dimethylformamide (10 ml) was cooled to −10° C. under argon and treated with iodoethane (0.404 ml, 5.00 mmol). Sodium hydride (60% dispersion in oil) (0.100 g, 2.500 mmol) was added portion wise. The mixture was allowed stirred warm to room temperature over 3 hours. The solvent was evaporated in vacuo and the residue was partitioned between ethyl acetate (20 ml) and brine (10 ml). The aqueous layer was re-extracted with ethyl acetate (20 ml) and the organic extracts were combined, washed with saturated sodium hydrogen carbonate solution (20 ml), water (2×20 ml) and brine (20 ml), dried and evaporated. The residue was purified by silica gel chromatography eluting with 25-100% ethyl acetate in isohexane to give 1,1-dimethylethyl 3-ethyl-1-methyl-2-oxo-4-imidazolidinecarboxylate (433 mg, 76%). LC/MS [M+H]$^+$=229.

(ii) A solution of 1,1-dimethylethyl 3-ethyl-1-methyl-2-oxo-4-imidazolidinecarboxylate (433 mg, 1.897 mmol) in TFA/DCM (1:2, 6 ml) was stirred at room temperature for 18 hours. The solution was evaporated and the residue was co-evaporated with dichloromethane and dried to give crude 3-ethyl-1-methyl-2-oxo-4-imidazolidinecarboxylic acid, (assume ~1.9 mmol). LC/MS [M+H]$^+$=173.

Examples 74-75

In forms obtainable or prepared from (4S)-2-oxo-3-{[(phenylmethyl)oxy]carbonyl}-4-imidazolidinecarboxylic acid In a manner analogous to that described for Example 73 above the compounds tabulated below (Table 11) were prepared by substituting the appropriate amine (or salt thereof) for the [1-(2,4-dichlorophenyl)methyl]amine used in the above procedure. All of the amines used in Table 11 are available from commercial sources or can be prepared using routes described previously in the chemical literature or analogous methods.

TABLE 11

| Example no. | Chemical name | [M + H]$^+$ | Retention time (mins) |
|---|---|---|---|
| E74 | N-{[2-Chloro-3-(trifluoromethyl)phenyl]methyl}-3-ethyl-1- | 364 | 2.44 |

TABLE 11-continued

| Example no. | Chemical name | [M + H]+ | Retention time (mins) |
|---|---|---|---|
| E75 | ![structure] N-[(2-Chloro-4-fluorophenyl)methyl]-3-ethyl-1-methyl-2-oxo-4-imidazolidinecarboxamide | 314 | 2.15 |

Example 76

N-{[2-Chloro-3-(trifluoromethyl)phenyl]methyl}-3-methyl-2-oxo-1-(2-pyrazinyl)-4-imidazolidinecarboxamide (E76) (in a form obtainable or prepared from (4S)-2-oxo-3-{[(phenylmethyl)oxy]carbonyl}-4-imidazolidinecarboxylic acid)

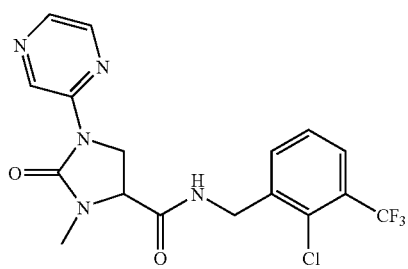

To a solution of 3-methyl-2-oxo-1-(2-pyrazinyl)-4-imidazolidinecarboxylic acid (145 mg, 0.561 mmol) and N-ethylmorpholine (0.426 ml, 3.36 mmol) in dichloromethane (5 ml) was added 1-hydroxybenzotriazole hydrate (86 mg, 0.561 mmol) and 1-ethyl-3-(3-dimethylaminopropyl)carbodiimide hydrochloride (107 mg, 0.561 mmol) and the reaction mixture was stirred for 10 minutes at room temperature. 1-[2-Chloro-3-(trifluoromethyl)phenyl]methanamine (141 mg, 0.673 mmol) was added and the reaction mixture was stirred at room temperature overnight. The reaction mixture was diluted with dichloromethane and washed with saturated sodium hydrogen carbonate solution, water and brine and separated by hydrophobic frit and the organic layer reduced under vacuum. The residue was purified by SP4 automated silica gel chromatography eluting with 10-100% ethyl acetate in isohexane to give N-{[2-chloro-3-(trifluoromethyl)phenyl]methyl}-3-methyl-2-oxo-1-(2-pyrazinyl)-4-imidazolidinecarboxamide (45 mg, 19% yield). LC/MS [M+H]+=413, retention time=2.21 minutes.

The 3-methyl-2-oxo-1-(2-pyrazinyl)-4-imidazolidinecarboxylic acid used in the method described above was prepared as follows:
(i) To a solution of 1,1-dimethylethyl 3-methyl-2-oxo-4-imidazolidinecarboxylate (400 mg, 1.998 mmol) (prepared as described in step (iii) of Example 13, starting from (4S)-2-oxo-3-{[(phenylmethyl)oxy]carbonyl}-4-imidazolidinecarboxylic acid) and 2-chloropyrazine (0.179 ml, 1.998 mmol) in 1,4-dioxane (20 ml) was added cesium carbonate (2604 mg, 7.99 mmol), tris(dibenzylideneacetone)dipalladium(0) (91 mg, 0.100 mmol) and Xantphos™ (87 mg, 0.150 mmol) and the reaction mixture was stirred at reflux overnight. The reaction mixture was allowed to cool to room temperature and the solvent was removed under vacuum and the residue was partitioned between dichloromethane and water. The organic layer was washed with saturated sodium hydrogen carbonate solution, water and brine and separated by hydrophobic frit. The solution was reduced under vacuum and the residue purified by silica gel chromatography eluting with 10-75% ethyl acetate in isohexane to give the crude 1,1-dimethylethyl 3-methyl-2-oxo-1-(2-pyrazinyl)-4-imidazolidinecarboxylate (322 mg, 38.2% yield) which was used in the next step. LC/MS [M+H]+=279.

(ii) Trifluoroacetic acid (1 ml) was added to a solution of 1,1-dimethylethyl 3-methyl-2-oxo-1-(2-pyrazinyl)-4-imidazolidinecarboxylate (290 mg, 0.709 mmol) in dichloromethane and the solution was stirred at room temperature overnight. The reaction mixture was reduced to dryness azeotroping with toluene and dried under heated vacuum. The residue was taken up in dichloromethane and extracted with saturated sodium hydrogen carbonate solution (×3) and aqueous layer reduced under vacuum. The residue was taken up in water and the solution acidified to pH 4 by the slow addition of 2N hydrochloric acid. The solution was washed with dichloromethane (×2) and the solvent was reduced under vacuum. The residue was triturated with the minimal amount of methanol, the solid was filtered off and the filtrate reduced under vacuum to leave a white solid which was dried under heated vacuum to give 3-methyl-2-oxo-1-(2-pyrazinyl)-4- imidazolidinecarboxylic acid (242 mg, ~0.7 mmol) which was used in the next step. LC/MS [M+H]+=223.

Example 77

1-(2-Chloro-3-pyridinyl)-N-[(2,4-dichlorophenyl)methyl]-3-methyl-2-oxo-4-imidazolidinecarboxamide (E77) (in a form obtainable or prepared from (4S)-2-oxo-3-{[(phenylmethyl)oxy]carbonyl}-4-imidazolidinecarboxylic acid)

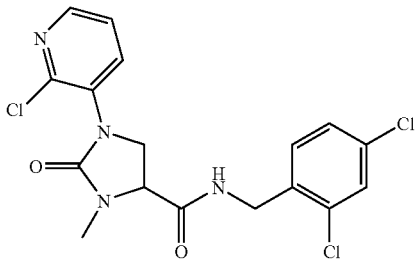

To a solution of 1-(2-chloro-3-pyridinyl)-3-methyl-2-oxo-4-imidazolidinecarboxylic acid (179 mg, 0.484 mmol) and N-ethylmorpholine (0.368 ml, 2.91 mmol) in dichloromethane (5 ml) was added 1-hydroxybenzotriazole hydrate (111 mg, 0.726 mmol) and 1-ethyl-3-(3-dimethylaminopropyl)carbodiimide hydrochloride (139 mg, 0.726 mmol) and the mixture was stirred for 10 minutes at room temperature. 1-(2,4-Dichlorophenyl)methanamine (128 mg, 0.726 mmol) was added and the reaction mixture was stirred at room temperature overnight. The reaction mixture was diluted with dichloromethane and washed with saturated sodium hydrogen carbonate solution, water and brine and separated by hydrophobic frit and the solution was reduced under vacuum. The residue was purified by SP4 automated silica gel chromatography eluting with 10-100% ethyl acetate in isohexane to give 1-(2-chloro-3-pyridinyl)-N-[(2,4-dichlorophenyl)methyl]-3-methyl-2-oxo-4-imidazolidinecarboxamide (60 mg, 27.6% yield). LC/MS [M+H]+=413, retention time=2.21 minutes The 1-(2-chloro-3-pyridinyl)-3-methyl-2-oxo-4-imidazolidinecarboxylic acid used in the method described above was prepared as follows:

(i) To a solution of 1,1-dimethylethyl 3-methyl-2-oxo-4-imidazolidinecarboxylate (650 mg, 3.25 mmol) (prepared as described in step (iii) of Example 13, starting from (4S)-2-oxo-3-{[(phenylmethyl)oxy]carbonyl}-4-imidazolidinecarboxylic acid) and 3-bromo-2-chloropyridine (625 mg, 3.25 mmol) in 1,4-dioxane (30 ml) was added cesium carbonate (4231 mg, 12.98 mmol), tris(dibenzylideneacetone)dipalladium(0) (149 mg, 0.162 mmol) and Xantphos™ (141 mg, 0.243 mmol) and the reaction stirred at reflux overnight. The reaction mixture was allowed to cool and solvent was removed under vacuum and the residue partitioned between ethyl acetate and water. The organic layer was separated and washed with saturated sodium hydrogen carbonate solution, water and brine and separated by hydrophobic frit. The organic solution was reduced under vacuum and the residue purified by SP4 automated silica gel chromatography eluting with 10-80% ethyl acetate in iso-hexane to give 1,1-dimethylethyl 1-(2-chloro-3-pyridinyl)-3-methyl-2-oxo-4-imidazolidinecarboxylate (579 mg, 51.5% yield)

LC/MS [M+H]+=312.

(ii) Trifluoroacetic acid (2.5 ml) was added to a solution of 1,1-dimethylethyl 1-(2-chloro-3-pyridinyl)-3-methyl-2-oxo-4-imidazolidinecarboxylate (579 mg, 1.857 mmol) in dichloromethane (10 ml) and the solution was stirred at room temperature for 36 hours. The solvent was evaporated under vacuum azeotroping with toluene and the residue dried under heated vacuum overnight 1-(2-chloro-3-pyridinyl)-3-methyl-2-oxo-4-imidazolidinecarboxylic acid (537 mg, 70.4% yield) which was used crude in the next step. LC/MS MH+=256.

Examples 78-79

In forms obtainable or prepared from (4S)-2-oxo-3-{[(phenylmethyl)oxy]carbonyl}-4-imidazolidinecarboxylic acid In a manner analogous to that described for Example 77 above the compounds tabulated below (Table 12) were prepared by substituting the appropriate amine (or salt thereof) for the [1-(2,4-dichlorophenyl)methyl]amine used in the above procedure. All of the amines used in Table 12 are available from commercial sources or can be prepared using routes described previously in the chemical literature or analogous methods.

TABLE 12

| Example no. | Chemical name | [M + H]+ | Retention time (mins) |
|---|---|---|---|
| E78 | ![structure] N-[(2-Chloro-3,4-difluorophenyl)methyl]-1-(2-chloro-3-pyridinyl)-3-methyl-2-oxo- | 415 | 2.07 |

TABLE 12-continued

| Example no. | Chemical name | [M + H]+ | Retention time (mins) |
|---|---|---|---|
| E79 | 4-imidazolidinecarboxamide 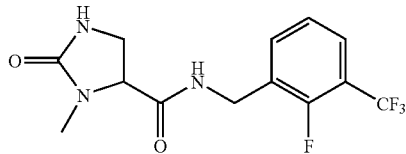 1-(2-Chloro-3-pyridinyl)-N-{[2-chloro-3-(trifluoromethyl)phenyl]methyl}-3-methyl-2-oxo-4-imidazolidinecarboxamide | 447 | 2.29 |

Example 80

N-{[2-Fluoro-3-(trifluoromethyl)phenyl]methyl}-3-methyl-2-oxo-4-imidazolidinecarboxamide (E80) (in a form obtainable or prepared from (4S)-2-oxo-3-{[(phenylmethyl)oxy]carbonyl}-4-imidazolidinecarboxylic acid)

A mixture of 3-methyl-2-oxo-4-imidazolidinecarboxylic acid (86 mg, 0.6 mmol) (prepared as described in Example 28 from 1,1-dimethylethyl 3-methyl-2-oxo-4-imidazolidinecarboxylate, itself prepared as described in step (iii) of Example 13, starting originally from (4S)-2-oxo-3-{[(phenylmethyl)oxy]carbonyl}-4-imidazolidinecarboxylic acid), N-ethyl morpholine (0.380 ml, 3.00 mmol), 1-hydroxybenzotriazole hydrate (110 mg, 0.720 mmol) and 1-ethyl-3-(3-dimethylaminopropyl)carbodiimide hydrochloride (138 mg, 0.720 mmol) in dichloromethane (9 ml) was stirred at room temperature for 10 minutes, under an argon atmosphere. {[2-Fluoro-3-(trifluoromethyl)phenyl]methyl}amine (0.1 ml, 0.684 mmol) was added and the reaction was stirred overnight under an argon atmosphere. The reaction mixture was diluted with dichloromethane (10 ml) and the solution was washed with saturated sodium hydrogen carbonate solution (10 ml), water (10 ml), citric acid solution (10 ml) and brine (10 ml). The citric acid layer was re-extracted with dichloromethane and the dichloromethane extracts were combined, dried and evaporated. The residue was purified by mass-directed automated HPLC. Fractions containing product were collected and the solvent was evaporated in vacuo to give N-{[2-fluoro-3-(trifluoromethyl)phenyl]methyl}-3-methyl-2-oxo-4-imidazolidinecarboxamide (16 mg, 8% yield) as a white solid. LC/MS [M+H]+=320, retention time=1.85 minutes.

Examples 81-83

In forms obtainable or prepared from (4S)-2-oxo-3-{[(phenylmethyl)oxy]carbonyl}-4-imidazolidinecarboxylic acid In a manner analogous to that described for Example 80 above the compounds tabulated below (Table 13) were prepared by substituting the appropriate amine (or salt thereof) for the {[2-fluoro-3-(trifluoromethyl)phenyl]methyl}amine used in the above procedure. All of the amines used in Table 13 are available from commercial sources or can be prepared using routes described previously in the chemical literature or analogous methods.

TABLE 13

| Example no. | Chemical name | [M + H]+ | Retention time (mins) |
|---|---|---|---|
| E81 | | 316 | 1.94 |

TABLE 13-continued

| Example no. | Chemical name | [M + H]+ | Retention time (mins) |
|---|---|---|---|
| E82 | 3-Methyl-N-{[2-methyl-3-(trifluoromethyl)phenyl]methyl}-2-oxo-4-imidazolidinecarboxamide | 302 | 1.78 |
| E83 | N-[(2,3-Dichlorophenyl)methyl]-3-methyl-2-oxo-4-imidazolidinecarboxamide | 336 | 2.00 |
| | N-{[4-Chloro-3-(trifluoromethyl)phenyl]methyl}-3-methyl-2-oxo-4-imidazolidinecarboxamide | | |

Example 84

N-{[4-Fluoro-3-(trifluoromethyl)phenyl]methyl}-3-methyl-2-oxo-4-imidazolidinecarboxamide (E84) (in a form obtainable or prepared from (4S)-2-oxo-3-{[(phenylmethyl)oxy]carbonyl}-4-imidazolidinecarboxylic acid)

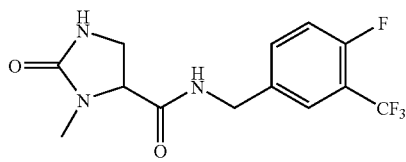

A mixture of 3-methyl-2-oxo-4-imidazolidinecarboxylic acid (86 mg, 0.6 mmol) (prepared as described in Example 28 from 1,1-dimethylethyl 3-methyl-2-oxo-4-imidazolidinecarboxylate, itself prepared as described in step (iii) of Example 13, starting originally from (4S)-2-oxo-3-{[(phenylmethyl)oxy]carbonyl}-4-imidazolidinecarboxylic acid), N-ethyl morpholine (0.380 ml, 3.00 mmol), 1-hydroxybenzotriazole hydrate (110 mg, 0.720 mmol) and 1-ethyl-3-(3-dimethylaminopropyl)carbodiimide hydrochloride (138 mg, 0.720 mmol) in dichloromethane (9 ml) was stirred at room temperature for 10 minutes, under an argon atmosphere. {[4-Fluoro-3-(trifluoromethyl)phenyl]methyl}amine (127 mg, 0.660 mmol) was added and the reaction was stirred overnight under an argon atmosphere. The reaction mixture was diluted with dichloromethane (10 ml) and the solution was washed with saturated sodium hydrogen carbonate solution (10 ml), water (10 ml) and brine (10 ml). The organic solution was dried and the solvent was evaporated in vacuo. The residue was purified by mass-directed automated HPLC. Fractions containing product were collected and the solvent was evaporated in vacuo to give N-{[4-fluoro-3-(trifluoromethyl)phenyl]methyl}-3-methyl-2-oxo-4-imidazolidinecarboxamide (8 mg, 4% yield) as a white solid. LC/MS [M+H]+=320, retention time=1.87 minutes.

Examples 85-87

In forms obtainable or prepared from (4S)-2-oxo-3-{[(phenylmethyl)oxy]carbonyl}-4-imidazolidinecarboxylic acid In a manner analogous to that described for Example 84 above the compounds tabulated below (Table 14) were prepared by substituting the appropriate amine (or salt thereof) for the {[4-fluoro-3-(trifluoromethyl)phenyl]methyl}amine used in the above procedure. All of the amines used in Table 14 are available from commercial sources or can be prepared using routes described previously in the chemical literature or analogous methods.

TABLE 14

| Example no. | Chemical name | [M + H]+ | Retention time (mins) |
|---|---|---|---|
| E85 | N-[(3-Chloro-2-methylphenyl)methyl]-3-methyl-2-oxo-4-imidazolidinecarboxamide | 282 | 1.78 |
| E86 | N-[(2,4-Dichloro-6-methylphenyl)methyl]-3-methyl-2-oxo-4-imidazolidinecarboxamide | 316 | 1.97 |
| E87 | N-[(4-Chloro-2-methylphenyl)methyl]-3-methyl-2-oxo-4-imidazolidinecarboxamide | 282 | 1.87 |

Example 88

N-[(2,4-Dichlorophenyl)methyl]-1-(5-fluoro-2-pyrimidinyl)-3-methyl-2-oxo-4-imidazolidinecarboxamide (E88) (in a form obtainable or prepared from (4S)-2-oxo-3-{[(phenylmethyl)oxy]carbonyl}-4-imidazolidinecarboxylic acid)

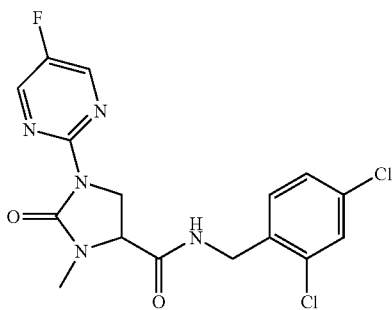

1-(5-Fluoro-2-pyrimidinyl)-3-methyl-2-oxo-4-imidazolidinecarboxylic acid (211 mg, 0.878 mmol) was suspended in dichloromethane (5 ml) under argon and treated with N-ethylmorpholine (0.667 ml, 5.27 mmol), 1-hydroxybenzotriazole hydrate (161 mg, 1.054 mmol), and 1-ethyl-3-(3-dimethylaminopropyl)carbodiimide hydrochloride (202 mg, 1.054 mmol) and stirred at room temperature for ~5 minutes. The mixture was then treated with 1-(2,4-dichlorophenyl)methanamine (0.117 ml, 0.878 mmol) and left to stir overnight at room temperature. The mixture was diluted with dichloromethane (~10 ml) and washed with saturated sodium hydrogen carbonate solution, water, 10% aqueous citric acid, water, and brine, then filtered through a hydrophobic frit and evaporated. Trituration of the resulting oil with diethyl ether gave N-[(2,4-dichlorophenyl)methyl]-1-(5-fluoro-2-pyrimidinyl)-3-methyl-2-oxo-4-imidazolidinecarboxamide (187 mg, 53.5% yield) as a white solid which was collected by filtration and dried in vacuo. LC/MS [M+H]+=398, retention time=2.12 minutes.

The 1-(5-fluoro-2-pyrimidinyl)-3-methyl-2-oxo-4-imidazolidinecarboxylic acid used in the method described above was prepared as follows:

(i) A solution of 1,1-dimethylethyl 3-methyl-2-oxo-4-imidazolidinecarboxylate (300 mg, 1.498 mmol) (prepared as described in step (iii) of Example 13, starting from (4S)-2-oxo-3-{[(phenylmethyl)oxy]carbonyl}-4-imidazolidinecarboxylic acid) and 2-chloro-5-fluoropyrimidine (0.194 ml, 1.573 mmol) in 1,4-dioxane (10 ml) was treated with cesium carbonate (732 mg, 2.247 mmol), Xantphos™ (65.0 mg, 0.112 mmol), and tris(dibenzylideneacetone)dipalladium(0) (34.3 mg, 0.037 mmol) and then heated at reflux for ~3 hrs. The mixture was cooled to room temperature, diluted with water (~25 ml) and extracted with ethyl acetate (3×). The combined ethyl acetate layers were washed with water and then with brine and evaporated to give a yellow/brown residue. This was purified by automated silica-gel column chromatography (Biotage SP-4), eluting with a 0-100% gradient of ethyl acetate in isohexane (8 column volumes), to give 1,1-dimethylethyl 1-(5-fluoro-2-pyrimidinyl)-3-methyl-2-oxo-4-imidazolidinecarboxylate (232 mg, 52.3% yield) as a white solid.

(ii) 1,1-Dimethylethyl 1-(5-fluoro-2-pyrimidinyl)-3-methyl-2-oxo-4-imidazolidinecarboxylate (232 mg, 0.783 mmol) was dissolved in a mixture of trifluoroacetic acid (2 ml, 26.0 mmol) and dichloromethane (4 ml) at 0° C. and then left to warm to room temperature and stirred overnight. The mixture was evaporated (azeotroping with toluene and then with dichloromethane to remove all TFA traces) to give 1-(5-fluoro-2-pyrimidinyl)-3-methyl-2-oxo-4-imidazolidinecarboxylic acid (211 mg) as a white solid which was used without further purification in subsequent chemistry. LC/MS MH+=240.85.

Example 89

N-[(2,4-Dichlorophenyl)methyl]-3-ethyl-2-oxo-4-imidazolidinecarboxamide (E89) (in a form obtainable or prepared from (4S)-2-oxo-3-{[(phenylmethyl)oxy]carbonyl}-4-imidazolidinecarboxylic acid)

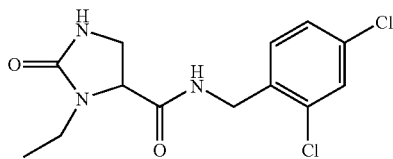

A mixture of 3-ethyl-2-oxo-4-imidazolidinecarboxylic acid (127 mg, 0.800 mmol), 1-hydroxybenzotriazole hydrate (147 mg, 0.960 mmol), 1-ethyl-3-(3-dimethylaminopropyl)carbodiimide hydrochloride (184 mg, 0.960 mmol) and N-ethyl morpholine (0.409 ml, 3.20 mmol) in dichloromethane (9 ml) was stirred at room temperature for 10 minutes. A solution of [1-(2,4-dichlorophenyl)methyl]amine (141 mg, 0.8 mmol) in dichloromethane (1 ml) was added and the reaction mixture was stirred at room temperature for 18 hours. The reaction mixture was diluted with dichloromethane (20 ml) and the mixture was washed with 3N citric acid solution (10 ml). The organic phase was separated, washed with brine (10 ml) and evaporated. The residue was purified by mass-directed automated HPLC. The residue was triturated with ether and the resulting solid was collected and dried to give the product as a white solid (45 mg, 18%). LCMS [M+H]+=316, retention time 1.93 minutes.

The 3-ethyl-2-oxo-4-imidazolidinecarboxylic acid used in the method described above was prepared as follows:

(i) To a stirred solution of 5-(1,1-dimethylethyl)1-(phenylmethyl)2-oxo-1,5-imidazolidinedicarboxylate (1602 mg, 5 mmol) (prepared as described in step (ii) of Example 13, starting from (4S)-2-oxo-3-{[(phenylmethyl)oxy]carbonyl}-4-imidazolidinecarboxylic acid) in tetrahydrofuran (20 ml) under argon at 0° C. was added sodium hydride (60% dispersion in oil, 210 mg, 5.25 mmol) (portion wise). The reaction mixture was stirred at 10° C. for 1 hour. Acetic acid (1 ml, 17.47 mmol) was added dropwise and the solvent was evaporated. The residue was partitioned between in ethyl acetate (30 ml) and brine (15 ml). The organic extracts were combined, dried and evaporated. The residue was purified by silica gel chromatography eluting with 50-100% ethyl acetate in isohexane to give 4-(1,1-dimethylethyl)1-(phenylmethyl) 2-oxo-1,4-imidazolidinedicarboxylate (780 mg, 49%). LC/MS [M+H]+=321.

(ii) A stirred solution of 4-(1,1-dimethylethyl)1-(phenylmethyl)2-oxo-1,4-imidazolidinedicarboxylate (0.769 g, 2.4 mmol) in N,N-dimethylformamide (10 ml) was cooled to −10° C. under argon and treated with iodoethane (0.194 ml, 2.400 mmol). Sodium hydride (60% dispersion in oil) (0.096 g, 2.400 mmol) was added portion wise. The mixture was allowed to warm to room temperature over 3 hours and stirred at room temperature for 16 hours. The solvent was evaporated and the residue was partitioned between ethyl acetate (20 ml) and brine (10 ml). The aqueous layer was re-extracted with ethyl acetate (20 ml) and the organic extracts were combined, washed with saturated sodium hydrogen carbonate solution (20 ml), water (2×20 ml) and brine (20 ml), dried and evaporated to give 4-(1,1-dimethylethyl)1-(phenylmethyl)3-ethyl-2-oxo-1,4-imidazolidinedicarboxylate (1.15 g) which was used crude in the next reaction. LC/MS [M+H]+=349.

(iii) A solution of 4-(1,1-dimethylethyl)1-(phenylmethyl)3-ethyl-2-oxo-1,4-imidazolidinedicarboxylate (836 mg, 2.4 mmol) in methanol (15 ml) containing palladium on carbon (10% paste, 200 mg) was hydrogenated at room temperature and pressure for 72 hours. The mixture was filtered through a filter pad and the pad washed with methanol. The filtrates were combined and evaporated to give 1,1-dimethylethyl 3-ethyl-2-oxo-4-imidazolidinecarboxylate which was used in the next reaction (540 mg). LC/MS [M+H]+=215.

(iv) A solution of 1,1-dimethylethyl 3-ethyl-2-oxo-4-imidazolidinecarboxylate (0.514 g, 2.4 mmol) in trifluoroacetic acid/dichloromethane (1:2, 6 ml) was stirred at room temperature for 18 hours. The solution was evaporated and the residue was co-evaporated with dichloromethane and dried to give 3-ethyl-2-oxo-4-imidazolidinecarboxylic acid (assume ~2.4 mmol). LC/MS [M+H]+=159.

Examples 90-91

In forms obtainable or prepared from (4S)-2-oxo-3-{[(phenylmethyl)oxy]carbonyl}-4-imidazolidinecarboxylic acid In a manner analogous to that described for Example 89 above the compounds tabulated below (Table 15) were prepared by substituting the appropriate amine (or salt thereof) for the [1-(2,4-dichlorophenyl)methyl]amine used in the above procedure. All of the amines used in Table 15 are available from commercial sources or can be prepared using routes described previously in the chemical literature or analogous methods.

TABLE 15

| Example no. | Chemical name | [M + H]⁺ | Retention time (mins) |
|---|---|---|---|
| E90 | N-[(2-Chloro-4-fluorophenyl)methyl]-3-ethyl-2-oxo-4-imidazolidinecarboxamide | 300 | 1.74 |
| E91 | N-{[2-Chloro-3-(trifluoromethyl)phenyl]methyl}-3-ethyl-2-oxo-4-imidazolidinecarboxamide | 350 | 2.05 |

Example 92

N-[(2,4-Dichlorophenyl)methyl]-3-methyl-1-[4-(methyloxy)-2-pyrimidinyl]-2-oxo-4-imidazolidinecarboxamide (E92) (in a form obtainable or prepared from (4S)-2-oxo-3-{[(phenylmethyl)oxy]carbonyl}-4-imidazolidinecarboxylic acid)

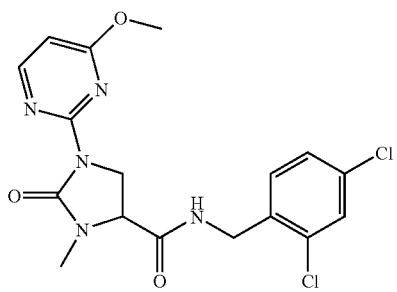

3-Methyl-1-[4-(methyloxy)-2-pyrimidinyl]-2-oxo-4-imidazolidinecarboxylic acid (76 mg, 0.3 mmol) (~0.3 mmol) in dichloromethane (4 ml) was treated with the 4A molecular sieves (200 mg, 0.300 mmol), and the mixture stirred at RT for 5 minutes. N-Ethylmorpholine (0.190 ml, 1.500 mmol), 1-hydroxybenzotriazole hydrate (55.1 mg, 0.360 mmol) and 1-ethyl-3-(3-dimethylaminopropyl)carbodiimide hydrochloride (82 mg, 0.360 mmol) were then added and the reaction stirred at RT under argon for 10 minutes. [(2,4-Dichlorophenyl)methyl]amine (58.1 mg, 0.330 mmol) was added and the reaction left to stir at RT under argon for 4 hours. The reaction mixture was diluted with dichloromethane (15 ml) and saturated sodium hydrogen carbonate solution (20 ml), and the product was extracted into dichloromethane (×2). The combined organic extracts were washed with water (20 ml), brine (20 ml) and then dried over magnesium sulphate. The solvent was evaporated in vacuo to give a yellow solid, which was purified by mass-directed automated HPLC. Fractions containing product were combined and solvent evaporated in vacuo, co-evaporated with diethyl ether to give N-[(2,4-dichlorophenyl)methyl]-3-methyl-1-[4-(methyloxy)-2-pyrimidinyl]-2-oxo-4-imidazolidinecarboxamide as a white solid (60 mg, 46.3% yield). LC/MS [M+H]⁺=410, retention time 1.73=minutes.

The 3-methyl-1-[4-(methyloxy)-2-pyrimidinyl]-2-oxo-4-imidazolidinecarboxylic acid used in the method described above was prepared as follows:

(i) A solution of 1,1-dimethylethyl 3-methyl-2-oxo-4-imidazolidinecarboxylate (500 mg, 2.497 mmol) (prepared as described in step (iii) of Example 13, starting from (4S)-2-oxo-3-{[(phenylmethyl)oxy]carbonyl}-4-imidazolidinecarboxylic acid) and 2-chloro-4-(methyloxy)pyrimidine (361 mg, 2.497 mmol) in 1,4-dioxane (20 ml) was treated with cesium carbonate (1220 mg, 3.75 mmol), Xantphos™ (108 mg, 0.187 mmol) and tris(dibenzylideneacetone)dipalladium (0) (57.2 mg, 0.062 mmol) and the mixture was heated at reflux under argon for 3 hours. After cooling to room temperature, the reaction mixture was diluted with water (15 ml) and extracted with ethyl acetate (×2, 20 ml). The organic layers were combined, washed with water (20 ml) and brine (20 ml), dried over magnesium sulphate and then evaporated in vacuo. The residue was purified by flash-silica gel chromatography eluting with 0-10% methanol in dichloromethane. The fractions containing product were combined and solvent evaporated in vacuo to give a yellow oil. The residue was purified again by flash-silica gel chromatography, eluting with 0-100% ethyl acetate in isohexane to give 1,1-dimethylethyl 3-methyl-1-[4-(methyloxy)-2-pyrimidinyl]-2-oxo-4-imidazolidinecarboxylate as a yellow oil (100 mg, 13% yield). LC/MS [M+H]⁺309.

(ii) A solution of 1,1-dimethylethyl 3-methyl-1-[4-(methyloxy)-2-pyrimidinyl]-2-oxo-4-imidazolidinecarboxylate (100 mg, 0.324 mmol) in dichloromethane (0.6 ml)/trifluoroacetic acid (0.300 ml) was stirred at room temperature for 24 hours. The solution was evaporated and the residue was co-evaporated with toluene (×3) and then dichloromethane (×4). The product was then dried in a vacuum oven (50° C.) to give crude 3-methyl-1-[4-(methyloxy)-2-pyrimidinyl]-2-oxo-4-imidazolidinecarboxylic acid as a yellow gum (95 mg, ~0.3 mmol) which was used in the next reaction. LC/MS [M+H]$^+$253.

Example 93

1-(5-Chloro-2-pyrimidinyl)-N-[(2,4-dichlorophenyl)methyl]-3-methyl-2-oxo-4-imidazolidinecarboxamide (E93) (in a form obtainable or prepared from (4S)-2-oxo-3-{[(phenylmethyl)oxy]carbonyl}-4-imidazolidinecarboxylic acid)

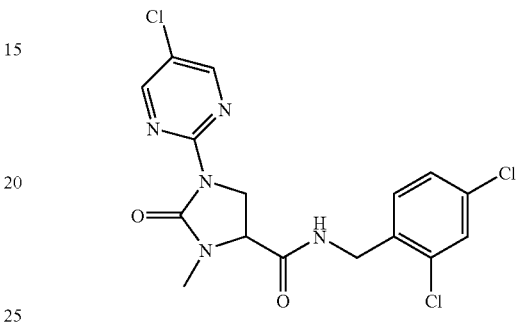

In a manner analogous to that described in Example 88 above 1-(5-chloro-2-pyrimidinyl)-N-[(2,4-dichlorophenyl)methyl]-3-methyl-2-oxo-4-imidazolidinecarboxamide was prepared substituting 2,5-dichloropyrimidine for 2-chloro-5-fluoropyrimidine used in step (i) of the above procedure. LC/MS [M+H]$^+$=4N3 retention time=2.34 minutes.

Examples 94-95

In a manner analogous to that described for Example 13 above the compounds tabulated below (Table 16) were prepared by substituting the appropriate amine (or salt thereof) for the {[2-chloro-3-(trifluoromethyl)phenyl]methyl}amine used in the above procedure. All of the amines used in Table 16 are available from commercial sources or can be prepared using routes described previously in the chemical literature or analogous methods.

| Example no. | In forms obtainable or prepared from (4S)-2-oxo-3-{[(phenylmethyl)oxy]carbonyl}-4-imidazolidinecarboxylic acid | | Retention time |
|---|---|---|---|
| 94 | N-[(2,4-Dichlorophenyl)methyl]-3-methyl-1-(6-methyl-3-pyridinyl)-2-oxo-4-imidazolidinecarboxamide | 393 | 2.27 |
| 95 | N-[(2-Chloro-3,4-difluorophenyl)methyl]-3-methyl-1-(6-methyl-3-pyridinyl)-2-oxo-4-imidazolidinecarboxamide | 395 | 2.11 |

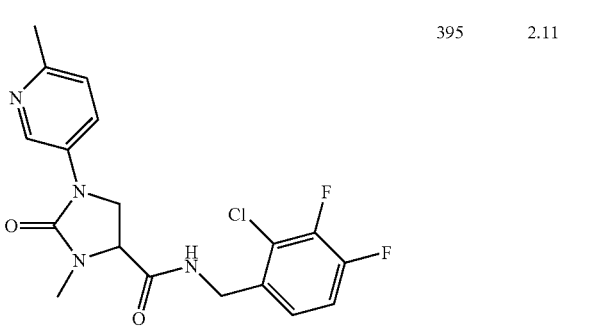

TABLE 16-continued

| Example no. | Chemical name | [M + H]$^+$ | Retention time (mins) |
|---|---|---|---|

Example 96

N-[(2,4-Dichlorophenyl)methyl]-1-(2-fluoro-4-pyridinyl)-3-methyl-2-oxo-4-imidazolidinecarboxamide (E96) (in a form obtainable or prepared from (4S)-2-oxo-3-{[(phenylmethyl)oxy]carbonyl}-4-imidazolidinecarboxylic acid)

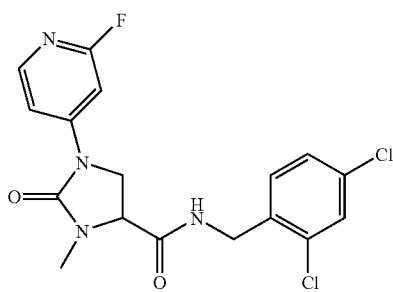

A solution of 1-(2-fluoro-4-pyridinyl)-3-methyl-2-oxo-4-imidazolidinecarboxylic acid (200 mg, 0.521 mmol) and N-ethyl morpholine (0.400 ml, 3.13 mmol) in dichloromethane (10 ml) was treated with 1-hydroxybenzotriazole hydrate (80 mg, 0.521 mmol) and 1-ethyl-3-(3-dimethylaminopropyl)carbodiimide hydrochloride (100 mg, 0.521 mmol) and the reaction mixture was stirred at room temperature for 10 minutes. [(2,4-Dichlorophenyl)methyl]amine (0.084 ml, 0.521 mmol) was then added and the reaction stirred overnight. The reaction mixture was diluted with dichloromethane and washed with saturated sodium hydrogen carbonate solution, water and brine and separated through a hydrophobic frit. The organic layer was reduced under vacuum. The residue was purified mass-directed automated HPLC to give N-[(2,4-dichlorophenyl)methyl]-1-(2-fluoro-4-pyridinyl)-3-methyl-2-oxo-4-imidazolidinecarboxamide (64 mg, 30.3% yield). LC/MS [M+H]$^+$=397, retention time=2.45 minutes.

The 1-(2-fluoro-4-pyridinyl)-3-methyl-2-oxo-4-imidazolidinecarboxylic acid used in the above procedure was prepared in a manner analogous to that described in Example 67 above substituting 4-bromo-2-fluoropyridine for 2-fluoro-3-iodopyridine used in step (i) of the Example 67 procedure.

Examples 97-98

In forms obtainable or prepared from (4S)-2-oxo-3-{[(phenylmethyl)oxy]carbonyl}-4-imidazolidinecarboxylic acid In a manner analogous to that described for Example 96 above the compounds tabulated below (Table 17) were prepared by substituting the appropriate amine (or salt thereof) for the [(2,4-dichlorophenyl)methyl]amine used in the above procedure. All of the amines used in Table 17 are available from commercial sources or can be prepared using routes described previously in the chemical literature or analogous methods.

TABLE 17

| Example no. | Chemical name | [M + H]$^+$ | Retention time (mins) |
|---|---|---|---|
| 97 | N-[(2-Chloro-3,4-difluorophenyl)methyl]-1-(2-fluoro-4-pyridinyl)-3-methyl-2-oxo-4-imidazolidinecarboxamide | 399 | 2.33 |

TABLE 17-continued

| Example no. | Chemical name | [M + H]+ | Retention time (mins) |
|---|---|---|---|
| 98 | 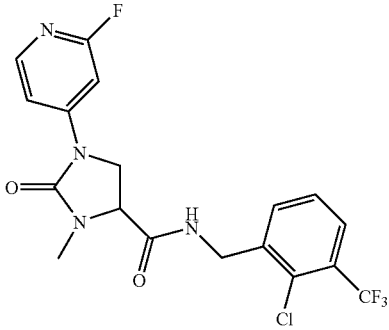<br>N-{[2-Chloro-3-(trifluoromethyl)phenyl]methyl}-1-(2-fluoro-4-pyridinyl)-3-methyl-2-oxo-4-imidazolidinecarboxamide | 431 | 2.28 |

Example 99

N-[(3-Chloro-2-methylphenyl)methyl]-1,3-dimethyl-2-oxo-4-imidazolidinecarboxamide (E99) (in a form obtainable or prepared from (4S)-2-oxo-3-{[(phenylmethyl)oxy]carbonyl}-4-imidazolidinecarboxylic acid)

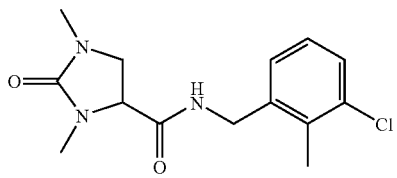

To 1,3-dimethyl-2-oxo-4-imidazolidinecarboxylic acid (6.000 ml, 0.600 mmol) (0.1M solution in dichloromethane) was added the N-ethylmorpholine (0.380 ml, 3.00 mmol), 1-hydroxybenzotriazole hydrate (110 mg, 0.720 mmol) and 1-ethyl-3-(3-dimethylaminopropyl)carbodiimide hydrochloride (138 mg, 0.720 mmol), and the reaction stirred at RT under argon for 10 minutes. [(3-Chloro-2-methylphenyl)methyl]amine (103 mg, 0.660 mmol) was then added and the reaction left to stir at RT under argon overnight. The reaction mixture was diluted with dichloromethane (15 ml) and then the solution was washed with saturated sodium hydrogen carbonate solution (20 ml), water (20 ml), 3N citric acid solution (20 ml), brine (20 ml) and then dried over magnesium sulphate. The solvent was evaporated in vacuo. The residue was purified by mass-directed automated HPLC. Fractions containing product were combined and solvent evaporated in vacuo, co-evaporated with diethyl ether to give the N-[(3-chloro-2-methylphenyl)methyl]-1,3-dimethyl-2-oxo-4-imidazolidinecarboxamide as a white solid (50 mg, 26.8% yield). LC/MS [M+H]+=296, retention time=1.96 minutes The 1,3-dimethyl-2-oxo-4-imidazolidinecarboxylic acid used in the method described above was prepared as follows:
(i) A stirred solution of 1,1-dimethylethyl 1-methyl-2-oxo-4-imidazolidinecarboxylate (1.75 g, 8.74 mmol) (prepared as described in step (i) of Example 49 from 5-(1,1-dimethylethyl)1-(phenylmethyl)3-methyl-2-oxo-1,5-imidazolidinedicarboxylate, itself prepared as described in step (ii) of Example 13, starting originally from (4S)-2-oxo-3-{[(phenylmethyl)oxy]carbonyl}-4-imidazolidinecarboxylic acid) in N,N-dimethylformamide (22 ml) was cooled to −10° C. under argon, and then the methyl iodide (2.186 ml, 35.0 mmol) was added. Sodium hydride (60% dispersion in oil) (0.329 g, 8.22 mmol) was then added portion wise. The reaction mixture was allowed to warm to RT while stirring under argon overnight. The solvent was evaporated in vacuo and then the residue partitioned between ethyl acetate (40 ml) and brine (30 ml). The aqueous layer was re-extracted with ethyl acetate (×2) and then the combined organic extracts were washed with water (×2, 50 ml), brine (50 ml) and dried over magnesium sulphate. The solvent was evaporated in vacuo. The crude product was purified by flash-silica gel chromatography, eluting with 25-100% ethyl acetate/iso-hexane. The fractions containing product were combined and solvent evaporated in vacuo to give a yellow oil, 1,1-dimethylethyl 1,3-dimethyl-2-oxo-4-imidazolidinecarboxylate (1.48 g, 79% yield).
(ii) A solution of 1,1-dimethylethyl 1,3-dimethyl-2-oxo-4-imidazolidinecarboxylate (1.92 g, 8.96 mmol) in dichloromethane (12 ml)/trifluoroacetic acid (6.00 ml) was stirred at room temperature for 24 hours. The solution was evaporated and the residue was co-evaporated with toluene (×3) and then dichloromethane (×2). The product was then dried to give crude 1,3-dimethyl-2-oxo-4-imidazolidinecarboxylic acid (1.65 g) which was dissolved in dichloromethane (90 ml) to give a ~0.1M solution in dichloromethane which was used in subsequent reactions. LC/MS [M+H]+=159.

Examples 100-108

In forms obtainable or prepared from (4S)-2-oxo-3-{[(phenylmethyl)oxy]carbonyl}-4-imidazolidinecarboxylic acid In a manner analogous to that described for Example 99 above the compounds tabulated below (Table 18) were prepared by substituting the appropriate amine (or salt thereof) for the [(3-chloro-2-methylphenyl)methyl]amine used in the above procedure. All of the amines used in Table 18 are available from commercial sources or can be prepared using routes described previously in the chemical literature or analogous methods.

TABLE 18

| Example no. | Chemical name | [M + H]⁺ | Retention time (mins) |
|---|---|---|---|
| E100 | 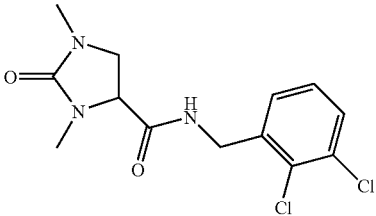<br>N-[(2,3-Dichlorophenyl)methyl]-1,3-dimethyl-2-oxo-4-imidazolidinecarboxamide | 316 | 1.97 |
| E101 | 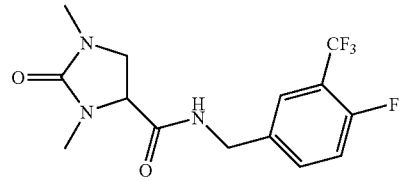<br>N-{[4-Fluoro-3-(trifluoromethyl)phenyl]methyl}-1,3-dimethyl-2-oxo-4-imidazolidinecarboxamide | 334 | 2.06 |
| E102 | 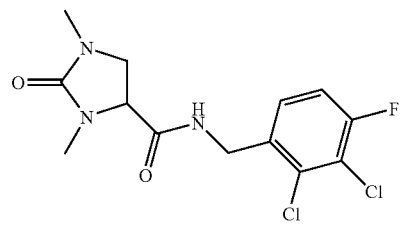<br>N-[(2,3-Dichloro-4-fluorophenyl)methyl]-1,3-dimethyl-2-oxo-4-imidazolidinecarboxamide | 334 | 2.05 |
| E103 | 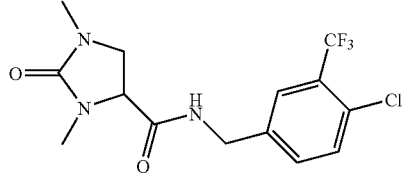<br>N-{[4-Chloro-3-(trifluoromethyl)phenyl]methyl}-1,3-dimethyl-2-oxo-4-imidazolidinecarboxamide | 350 | 2.19 |
| E104 | 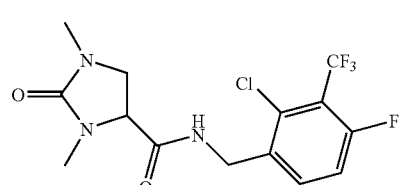<br>N-{[2-Chloro-4-fluoro-3- | 369 | 2.20 |

TABLE 18-continued

| Example no. | Chemical name | [M + H]⁺ | Retention time (mins) |
|---|---|---|---|
| | (trifluoromethyl)phenyl]methyl}-1,3-dimethyl-2-oxo-4-imidazolidinecarboxamide | | |
| E105 | N-[(2,4-Dichloro-6-methylphenyl)methyl]-1,3-dimethyl-2-oxo-4-imidazolidinecarboxamide | 330 | 2.17 |
| E106 | 1,3-Dimethyl-N-{[2-methyl-3-(trifluoromethyl)phenyl]methyl}-2-oxo-4-imidazolidinecarboxamide | 330 | 2.17 |
| E107 | N-[(4-Chloro-2-methylphenyl)methyl]-1,3-dimethyl-2-oxo-4-imidazolidinecarboxamide | 296 | 2.00 |
| E108 | N-[(2-Chloro-4-cyanophenyl)methyl]-1,3-dimethyl-2-oxo-4-imidazolidinecarboxamide | 307 | 1.68 |

Example 109

N-[(2,4-Dichlorophenyl)methyl]-3-methyl-1-[4-(1-methylethyl)-2-pyrimidinyl]-2-oxo-4-imidazolidinecarboxamide (E109) (in a form obtainable or prepared from (4S)-2-oxo-3-{[(phenylmethyl)oxy]carbonyl}-4-imidazolidinecarboxylic acid)

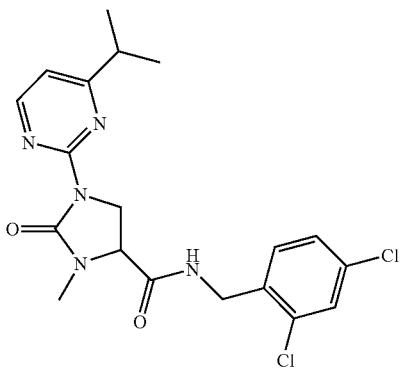

In a manner analogous to that described in Example 92 above N-[(2,4-dichlorophenyl)methyl]-3-methyl-1-[4-(1-methylethyl)-2-pyrimidinyl]-2-oxo-4-imidazolidinecarboxamide was prepared substituting 2-chloro-4-(1-methylethyl)pyrimidine for the 2-chloro-4-(methyloxy)pyrimidine used in step (i) of the Example 92 procedure. LC/MS [M+H]$^+$=422, retention time=2.42 minutes.

Example 110

N-[(2,4-Dichlorophenyl)methyl]-3-(2,2-difluoroethyl)-1-methyl-2-oxo-4-imidazolidinecarboxamide (E110) (in a form obtainable or prepared from (4S)-2-oxo-3-{[(phenylmethyl)oxy]carbonyl}-4-imidazolidinecarboxylic acid)

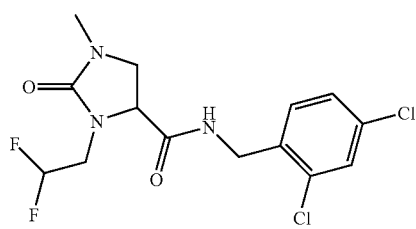

A mixture of 3-(2,2-difluoroethyl)-1-methyl-2-oxo-4-imidazolidinecarboxylic acid (105 mg, 0.505 mmol), 1-hydroxybenzotriazole hydrate (93 mg, 0.606 mmol), 1-ethyl-3-(3-dimethylaminopropyl)carbodiimide hydrochloride (116 mg, 0.606 mmol) and N-ethyl morpholine (0.258 ml, 2.020 mmol) in dichloromethane (7 ml) was stirred at room temperature for 10 minutes. [1-(2,4-Dichlorophenyl)methyl] amine (89 mg, 0.505 mmol) was added, a solid precipitated and DMF (1 ml) was added. The reaction mixture was stirred at room temperature for 18 hours, it was then diluted with dichloromethane (10 ml), washed with saturated sodium hydrogen carbonate solution (10 ml), water (10 ml), citric acid solution (10 ml) and brine (10 ml). The organic phase was dried (magnesium sulfate) and evaporated. The residue was purified by silica gel chromatography using 0-20% of methanol in dichloromethane followed by mass-directed automated HPLC. The fraction containing the desired product was evaporated and the residue was triturated with diethyl ether and dried to give a white solid (10 mg). LC/MS [M+H]$^+$=366, retention time 2.29 minutes.

The 3-(2,2-difluoroethyl)-1-methyl-2-oxo-4-imidazolidinecarboxylic acid used in the method described above was prepared as follows:
(i) To a solution of 1,1-dimethylethyl 1-methyl-2-oxo-4-imidazolidinecarboxylate (200 mg, 0.999 mmol) (prepared as described in step (i) of Example 49 from 5-(1,1-dimethylethyl)1-(phenylmethyl)3-methyl-2-oxo-1,5-imidazolidinedicarboxylate, itself prepared as described in step (ii) of Example 13, starting originally from (4S)-2-oxo-3-{[(phenylmethyl)oxy]carbonyl}-4-imidazolidinecarboxylic acid) in N,N-dimethylformamide (10 ml) at −35° C. under argon was added sodium hydride (39.9 mg, 0.999 mmol). The mixture was stirred for 15 minutes, 2,2-difluoroethyl trifluoromethanesulfonate (428 mg, 1.998 mmol) was added and the reaction mixture was stirred at −35° C. for 30 minutes then slowly warmed to −15° C. After 1 hour the reaction mixture was quenched with water (10 ml), warmed to room temperature and extracted with ethyl acetate (20 ml×2). The combined organic layers were washed with sodium hydrogen carbonate saturated solution (15 ml), water (10 ml×2) and brine (15 ml). The organic layer was then dried (magnesium sulfate), filtered and evaporated. The crude residue was purified by silica gel chromatography eluting with 10-100% of ethyl acetate in isohexane to give 1,1-dimethylethyl 3-(2,2-difluoroethyl)-1-methyl-2-oxo-4-imidazolidinecarboxylate (178 mg). LC/MS [M+H]$^+$=265.
(ii) 1,1-Dimethylethyl 3-(2,2-difluoroethyl)-1-methyl-2-oxo-4-imidazolidinecarboxylate (178 mg, 0.674 mmol) was dissolved in dichloromethane (3.00 ml) and trifluoroacetic acid (1 ml) was added. The solution was stirred at room temperature for 2 hours. The solvent was evaporated and the residue co-evaporated with dichloromethane and toluene to give a crude 3-(2,2-difluoroethyl)-1-methyl-2-oxo-4-imidazolidinecarboxylic acid (assume 0.674 mmol) which was used for the next reaction. LC/MS [M+H]$^+$=209.

Example 111

N-[(2,4-Dichlorophenyl)methyl]-1-(3-fluoro-2-pyridinyl)-3-methyl-2-oxo-4-imidazolidinecarboxamide (E111) (in a form obtainable or prepared from (4S)-2-oxo-3-{[(phenylmethyl)oxy]carbonyl}-4-imidazolidinecarboxylic acid)

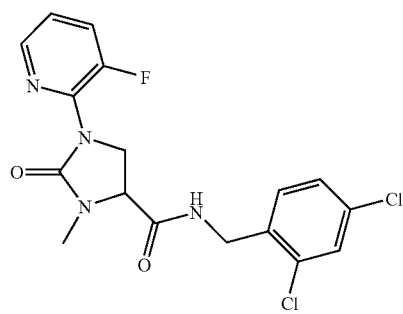

In a manner analogous to that described in Example 67 above N-[(2,4-dichlorophenyl)methyl]-1-(3-fluoro-2-pyridinyl)-3-methyl-2-oxo-4-imidazolidinecarboxamide was prepared substituting 2-bromo-3-fluoropyridine for 2-fluoro-3-iodopyridine used in step (i) of the Example 67 procedure. LC/MS [M+H]⁺=397, retention time=2.32 minutes.

Example 112

N-[(2,4-Dichlorophenyl)methyl]-3-methyl-1-(1-methyl-1H-pyrazol-5-yl)-2-oxo-4-imidazolidinecarboxamide (E112) (in a form obtainable or prepared from (4S)-2-oxo-3-{[(phenylmethyl)oxy]carbonyl}-4-imidazolidinecarboxylic acid)

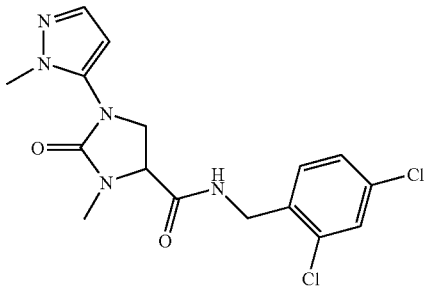

To a stirred mixture of N-[(2,4-dichlorophenyl)methyl]-3-methyl-2-oxo-4-imidazolidinecarboxamide (200 mg, 0.662 mmol) (prepared as described in Example 30), 5-iodo-1-methyl-1H-pyrazole (165 mg, 0.794 mmol) in 1,4-dioxane (20 ml) was added potassium phosphate (703 mg, 3.31 mmol), copper (I) iodide (126 mg, 0.662 mmol) and trans-N,N-dimethylcyclohexane-1,2-diamine (0.104 ml, 0.662 mmol) and the reaction mixture was heated at reflux under argon for 18 hours. After cooling to room temperature, ethyl acetate (20 ml), water (10 ml) and 0.880 ammonia solution (5 ml) were added. The organic layer was separated and the aqueous layer was extracted with ethyl acetate (2×20 ml). The organic extracts were combined, washed with citric acid solution (20 ml), water (10 ml) and brine (10 ml), dried and evaporated. The residue was purified by silica gel chromatography eluting with 0-10% methanol in dichloromethane followed by mass-directed automated HPLC to give N-[(2,4-dichlorophenyl)methyl]-3-methyl-1-(1-methyl-1H-pyrazol-5-yl)-2-oxo-4-imidazolidinecarboxamide (40 mg, 16%). LC/MS [M+H]⁺=382, retention time=2.12 minutes.

Example 113

1-(2-Cyano-3-pyridinyl)-N-[(2,4-dichlorophenyl)methyl]-3-methyl-2-oxo-4-imidazolidinecarboxamide (E113) (in a form obtainable or prepared from (4S)-2-oxo-3-{[(phenylmethyl)oxy]carbonyl}-4-imidazolidinecarboxylic acid)

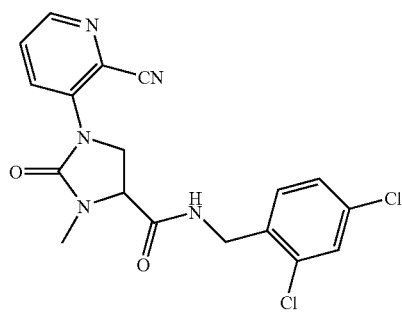

A suspension of N-[(2,4-dichlorophenyl)methyl]-3-methyl-2-oxo-4-imidazolidinecarboxamide (200 mg, 0.662 mmol) (prepared as described in Example 30) and 3-bromo-2-pyridinecarbonitrile (121 mg, 0.662 mmol) in 1,4-dioxane (5 ml) was treated with cesium carbonate (323 mg, 0.993 mmol), Xantphos™ (28.7 mg, 0.050 mmol) and tris(dibenzylideneacetone)dipalladium(0) (15.15 mg, 0.017 mmol) and the mixture was heated at reflux under argon for overnight. After cooling to room temperature, the reaction mixture was diluted with saturated sodium hydrogen carbonate solution and extracted with dichloromethane. The organic layers were combined, washed with water and brine and evaporated in vacuo. The residue was purified by silica gel chromatography eluting with 10-100% ethyl acetate in isohexane to give 1-(2-cyano-3-pyridinyl)-N-[(2,4-dichlorophenyl)methyl]-3-methyl-2-oxo-4-imidazolidinecarboxamide (212 mg, 78% yield). LC/MS [M+H]⁺=404, retention time=2.32 minutes.

Example 114

N-[(2,4-Dichlorophenyl)methyl]-3-methyl-1-(6-methyl-3-pyridazinyl)-2-oxo-4-imidazolidinecarboxamide (E114) (in a form obtainable or prepared from (4S)-2-oxo-3-{[(phenylmethyl)oxy]carbonyl}-4-imidazolidinecarboxylic acid)

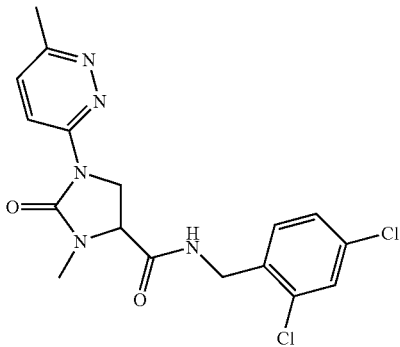

In a manner analogous to that described in Example 92 above N-[(2,4-dichlorophenyl)methyl]-3-methyl-1-(6-methyl-3-pyridazinyl)-2-oxo-4-imidazolidinecarboxamide was prepared substituting 3-chloro-6-methylpyridazine for 2-chloro-4-(methyloxy)pyrimidine used in step (i) of the Example 92 procedure. LC/MS [M+H]⁺=394, retention time=1.96 minutes.

Example 115

N-[(2,4-Dichlorophenyl)methyl]-1-(2,2-difluoroethyl)-3-methyl-2-oxo-4-imidazolidinecarboxamide (E115) (in a form obtainable or prepared from (4S)-2-oxo-3-{[(phenylmethyl)oxy]carbonyl}-4-imidazolidinecarboxylic acid)

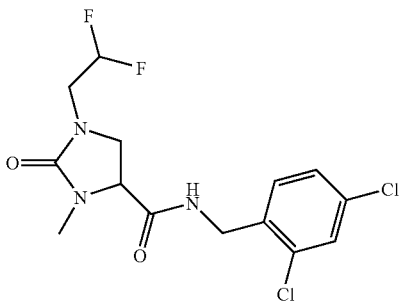

A mixture of 1-(2,2-difluoroethyl)-3-methyl-2-oxo-4-imidazolidinecarboxylic acid (125 mg, 0.6 mmol), 1-hydroxybenzotriazole hydrate (110 mg, 0.720 mmol), 1-ethyl-3-(3-dimethylaminopropyl)carbodiimide hydrochloride (138 mg, 0.720 mmol) and N-ethylmorpholine (0.305 ml, 2.400 mmol) in dichloromethane (5 ml) was stirred for 10 minutes. [(2,4-Dichlorophenyl)methyl]amine (106 mg, 0.600 mmol) was added and the solution was stirred at room temperature for 3 days. The reaction mixture was diluted with dichloromethane (10 ml), washed with saturated sodium hydrogen carbonate solution (10 ml), water (10 ml) and brine (10 ml). The organic phase was dried (magnesium sulphate) and evaporated. The residue was purified by the mass-directed automated HPLC. The fraction containing the desired product was evaporated and the residue was triturated with diethyl ether and dried to give N-[(2,4-dichlorophenyl)methyl]-1-(2,2-difluoroethyl)-3-methyl-2-oxo-4-imidazolidinecarboxamide (25 mg). LC/MS [M+H]⁺=366, retention time=2.09 minutes.

The 1-(2,2-difluoroethyl)-3-methyl-2-oxo-4-imidazolidinecarboxylic acid used in the method described above was prepared as follows:

(i) To a solution of 1,1-dimethylethyl 3-methyl-2-oxo-4-imidazolidinecarboxylate (200 mg, 0.999 mmol) (prepared as described in step (iii) of Example 13, starting from (4S)-2-oxo-3-{[(phenylmethyl)oxy]carbonyl}-4-imidazolidinecarboxylic acid) and 2,2-difluoroethyl trifluoromethanesulfonate (428 mg, 1.998 mmol) in N,N-dimethylformamide (4 ml) at −35° C. under argon was added sodium hydride (80 mg, 1.998 mmol). The reaction mixture was warmed to 0° C. over 2 hours, quenched with water (10 ml) and extracted with ethyl acetate (20 ml×2). The combined organic layers were washed with saturated sodium hydrogen carbonate solution (15 ml), water (10 ml×2) and brine (15 ml). The organic layer was dried (magnesium sulfate), filtered and evaporated. The residue was purified by silica gel chromatography eluting with 10-100% ethyl acetate in isohexane to give 1,1-dimethylethyl 1-(2,2-difluoroethyl)-3-methyl-2-oxo-4-imidazolidinecarboxylate (200 mg). LC/MS [M+H]⁺=265.

(ii) 1,1-dimethylethyl 1-(2,2-difluoroethyl)-3-methyl-2-oxo-4-imidazolidinecarboxylate (200 mg, 0.757 mmol) was dissolved in dichloromethane (3 ml) and trifluoroacetic acid (1 ml) added. The solution was stirred at room temperature for 2 hours. The solvent was evaporated and the residue co-evaporated with toluene (×2) to give 1-(2,2-difluoroethyl)-3-methyl-2-oxo-4-imidazolidinecarboxylic acid (0.757 mmol) which was used in the next step. LC/MS [M+H]⁺=209.

Example 116

N-[(2,4-Dichlorophenyl)methyl]-3-methyl-2-oxo-1-(2,2,2-trifluoroethyl)-4-imidazolidinecarboxamide (E116) (in a form obtainable or prepared from (4S)-2-oxo-3-{[(phenylmethyl)oxy]carbonyl}-4-imidazolidinecarboxylic acid)

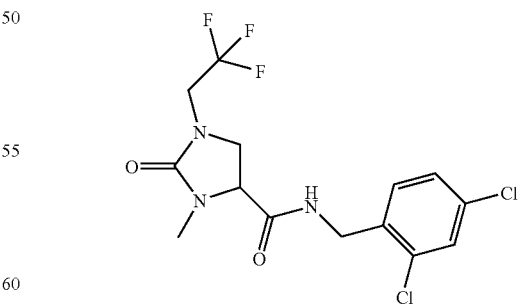

In a manner analogous to that described in Example 115 above N-[(2,4-dichlorophenyl)methyl]-3-methyl-2-oxo-1-(2,2,2-trifluoroethyl)-4-imidazolidinecarboxamide was prepared substituting 2,2,2-trifluoroethyl trichloromethanesulfonate for 2,2-difluoroethyl trifluoromethanesulfonate used in step (i) of the Example 115 procedure. LC/MS [M+H]$^+$=384, retention time=2.41 minutes.

Example 117

N-[(2,4-Dichlorophenyl)methyl]-1-(2-fluoroethyl)-3-methyl-2-oxo-4-imidazolidinecarboxamide (E117) (in a form obtainable or prepared from (4S)-2-oxo-3-{[(phenylmethyl)oxy]carbonyl}-4-imidazolidinecarboxylic acid)

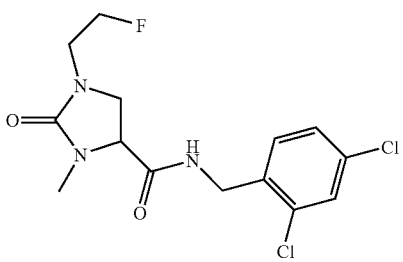

In a manner analogous to that described in Example 115 above N-[(2,4-dichlorophenyl)methyl]-1-(2-fluoroethyl)-3-methyl-2-oxo-4-imidazolidinecarboxamide was prepared substituting 1-fluoro-2-iodoethane for 2,2-difluoroethyl trifluoromethanesulfonate used in step (i) of the Example 115 procedure. LC/MS [M+H]$^+$=348, retention time=2.11 minutes.

Example 118

N-[(2,4-Dichlorophenyl)methyl]-1-ethyl-3-methyl-2-oxo-4-imidazolidinecarboxamide (E118) (in a form obtainable or prepared from (4S)-2-oxo-3-{[(phenylmethyl)oxy]carbonyl}-4-imidazolidinecarboxylic acid)

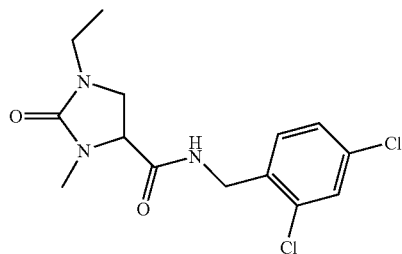

In a manner analogous to that described in Example 115 above N-[(2,4-dichlorophenyl)methyl]-1-ethyl-3-methyl-2-oxo-4-imidazolidinecarboxamide was prepared substituting iodoethane for 2,2-difluoroethyl trifluoromethanesulfonate used in step (i) of the Example 115 procedure. LC/MS [M+H]$^+$=330, retention time=2.17 minutes.

Examples 119-121

In forms obtainable or prepared from (4S)-2-oxo-3-{[(phenylmethyl)oxy]carbonyl}-4-imidazolidinecarboxylic acid In a manner analogous to that described for Example 99 above the compounds tabulated below (Table 19) were prepared by substituting the appropriate amine (or salt thereof) for the [(3-chloro-2-methylphenyl)methyl]amine used in the above procedure. All of the amines used in Table 19 are available from commercial sources or can be prepared using routes described previously in the chemical literature or analogous methods.

TABLE 19

| Example no. | Chemical name | [M + H]$^+$ | Retention time (mins) |
|---|---|---|---|
| E119 | ![structure] N-[(2,4-Dichloro-6-fluorophenyl)methyl]-1,3-dimethyl-2-oxo-4-imidazolidinecarboxamide | 334 | 2.01 |

TABLE 19-continued

| Example no. | Chemical name | [M + H]⁺ | Retention time (mins) |
|---|---|---|---|
| E120 | 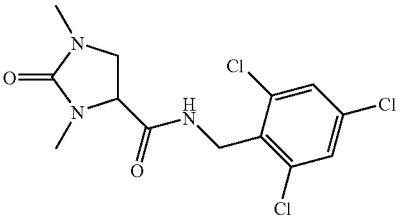 1,3-Dimethyl-2-oxo-N-[(2,4,6-trichlorophenyl)methyl]-4-imidazolidinecarboxamide | 352 | 2.16 |
| E121 | 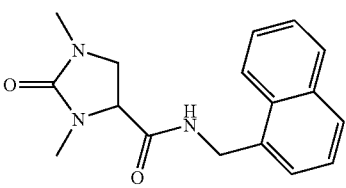 1,3-Dimethyl-N-(1-naphthalenylmethyl)-2-oxo-4-imidazolidinecarboxamide | 298 | 1.95 |

Examples 122 and 123

In forms obtainable or prepared from (4S)-2-oxo-3-{[(phenylmethyl)oxy]carbonyl}-4-imidazolidinecarboxylic acid In a manner analogous to that described for Example 84 above the compounds tabulated below (Table 20) were prepared by substituting the appropriate amine (or salt thereof) for the {[4-fluoro-3-(trifluoromethyl)phenyl]methyl}amine used in the above procedure. All of the amines used in Table 20 are available from commercial sources or can be prepared using routes described previously in the chemical literature or analogous methods.

TABLE 20

| Example no. | Chemical name | [M + H]⁺ | Retention time (mins) |
|---|---|---|---|
| E122 | 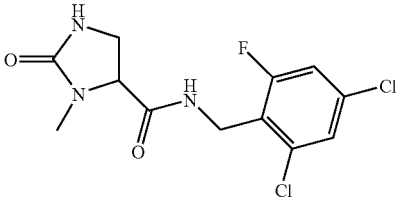 N-[(2,4-Dichloro-6-fluorophenyl)methyl]-3-methyl-2-oxo-4-imidazolidinecarboxamide | 320 | 1.88 |

TABLE 20-continued

| Example no. | Chemical name | [M + H]+ | Retention time (mins) |
|---|---|---|---|
| E123 | 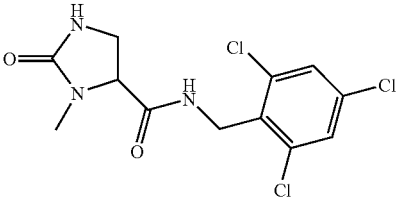 3-Methyl-2-oxo-N-[(2,4 6-trichlorophenyl)methyl]-4-imidazolidinecarboxamide | 338 | 1.97 |

Example 124

N-[(2,4-Dichlorophenyl)methyl]-3-methyl-1-(1-methylethyl)-2-oxo-4-imidazolidinecarboxamide (E124)

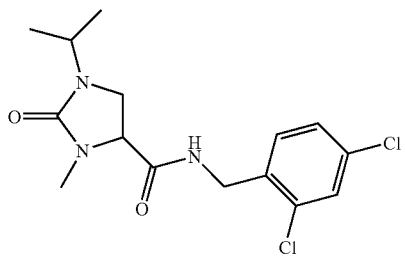

A mixture of 3-methyl-1-(1-methylethyl)-2-oxo-4-imidazolidinecarboxylic acid (100 mg, 0.537 mmol), N-ethylmorpholine (0.274 ml, 2.148 mmol), 1-hydroxybenzotriazole hydrate (99 mg, 0.644 mmol) and 1-ethyl-3-(3-dimethylaminopropyl)carbodiimide hydrochloride (124 mg, 0.644 mmol) in dichloromethane (9 ml) was stirred at room temperature for 10 minutes. A solution of [1-(2,4-dichlorophenyl)methyl] amine (95 mg, 0.537 mmol) in dichloromethane (1 ml) was added and the reaction mixture was stirred at room temperature for 18 hours. The reaction mixture was diluted with dichloromethane (10 ml) and the mixture was washed with saturated sodium hydrogen carbonate solution (10 ml) and brine (10 ml), dried and evaporated. The residue was purified by mass-directed automated HPLC. The residue was triturated with ether and the resulting solid was collected and dried to give N-[(2,4-dichlorophenyl)methyl]-3-methyl-1-(1-methylethyl)-2-oxo-4-imidazolidinecarboxamide (124 mg, 67%). LCMS [M+H]+=344, retention time=2.32 minutes.

The 3-methyl-1-(1-methylethyl)-2-oxo-4-imidazolidinecarboxylic acid used in the method described above was prepared as follows:

A stirred solution of methyl 3-methyl-2-oxo-4-imidazolidinecarboxylate (316 mg, 2 mmol) (prepared as described in step (ii) of Example 8) in N,N-dimethylformamide (5 ml) was cooled to 0° C. under argon and treated with sodium hydride (60% dispersion in oil) (120 mg, 3.00 mmol). After 10 minutes 2-iodopropane (0.400 ml, 4.00 mmol) was added and the reaction mixture was stirred at room temperature for 18 hours. A solution of lithium hydroxide (57.5 mg, 2.400 mmol) in water (1 ml) was added and the reaction mixture was stirred at room temperature for 30 minutes. Hydrochloric acid (2M) was added to adjust the pH of the mixture to pH 2 and the solvent was evaporated. Dimethylsulfoxide (3 ml) was added to the residue and the suspension was filtered. The filtrate was purified by mass-directed automated HPLC to give 3-methyl-1-(1-methylethyl)-2-oxo-4-imidazolidinecarboxylic acid (100 mg, 27%, over 2 steps). LC/MS [M+H]+ =187.

Examples 125 and 126

In a manner analogous to that described for Example 124 above the compounds tabulated below (Table 21) were prepared by substituting the appropriate alkyl bromide for the 2-iodopropane used in the above procedure. All of the alkyl bromides used in Table 21 are available from commercial sources or can be prepared using routes described previously in the chemical literature or analogous methods.

TABLE 21

| Example no. | Chemical name | [M + H]+ | Retention time (mins) |
|---|---|---|---|
| E125 | 1-(Cyclopropylmethyl)-N-[(2,4-dichlorophenyl)methyl]-3-methyl-2-oxo-4-imidazolidinecarboxamide | 356 | 2.41 |
| E126 | 1-(Cyclobutylmethyl)-N-[(2,4-dichlorophenyl)methyl]-3-methyl-2-oxo-4-imidazolidinecarboxamide | 370 | 2.60 |

Example 127

1-Cyclopentyl-N-[(2,4-dichlorophenyl)methyl]-3-methyl-2-oxo-4-imidazolidinecarboxamide (E127)

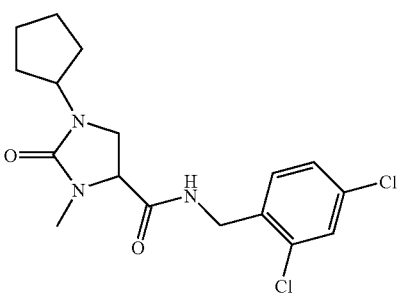

A mixture of 1-cyclopentyl-3-methyl-2-oxo-4-imidazolidinecarboxylic acid (39 mg, 0.184 mmol), N-ethylmorpholine (0.094 ml, 0.735 mmol), 1-hydroxybenzotriazole hydrate (33.8 mg, 0.220 mmol) and 1-ethyl-3-(3-dimethylaminopropyl)carbodiimide hydrochloride (42.3 mg, 0.220 mmol) in dichloromethane (9 ml) was stirred at room temperature for 10 minutes. A solution of [1-(2,4-dichlorophenyl)methyl]amine (32.3 mg, 0.184 mmol) in dichloromethane (1 ml) was added and the reaction mixture was stirred at room temperature for 72 hours. The reaction mixture was diluted with dichloromethane (10 ml) and the mixture was washed with saturated sodium hydrogen carbonate solution (10 ml) and brine (10 ml), dried and evaporated. The residue was purified by mass-directed automated HPLC. The residue was triturated with ether and the resulting solid was collected and dried to give 1-cyclopentyl-N-[(2,4-dichlorophenyl)methyl]-3-methyl-2-oxo-4-imidazolidinecarboxamide (42 mg, 62%). LCMS [M+H]+=370, retention time=2.28 minutes.

The 1-cyclopentyl-3-methyl-2-oxo-4-imidazolidinecarboxylic acid used in the method described above was prepared as follows:

A stirred solution of methyl 3-methyl-2-oxo-4-imidazolidinecarboxylate (316 mg, 2.0 mmol) (prepared as described in step (ii) of Example 8) in N,N-dimethylformamide (5 ml) was cooled to 0° C. under argon and treated with sodium hydride (60% dispersion in oil) (80 mg, 2.0 mmol). After 10 minutes bromocyclopentane (298 mg, 2.0 mmol) was added and the reaction mixture was stirred at room temperature for 3 hours and then at 60° C. for 18 hours. After cooling to room temperature additional sodium hydride (60% dispersion in oil) (80 mg, 2.0 mmol) was added followed by bromocyclopentane (298 mg, 2.0 mmol) and the reaction mixture was heated at 60° C. for 48 hours. After cooling to room temperature a solution of lithium hydroxide (0.057 g, 2.400 mmol) in water (1 ml) was added and the reaction mixture was stirred at room temperature for 30 minutes. Hydrochloric acid (2M) was added to adjust the pH of the mixture to pH 2 and the solvent was evaporated. Dimethylsulfoxide (3 ml) was added to the residue and the suspension was filtered. The filtrate was purified by mass-directed automated HPLC to give 1-cyclopentyl-3-methyl-2-oxo-4-imidazolidinecarboxylic acid (39 mg, 9%). LC/MS [M+H]+=213.

Mass-Directed Automated HPLC

Where indicated in the above examples, purification by mass-directed automated HPLC was carried out using the following apparatus and conditions:

Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
Waters MassLynx version 4 SP2
Column The columns used are Waters Atlantis, the dimensions of which are 19 mm×100 mm (small scale) and 30 mm×100 mm (large scale). The stationary phase particle size is 5 µm.
Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods There are five methods used depending on the analytical retention time of the compound of interest. They have a 13.5-minute runtime, which comprises a 10-minute gradient followed by a 3.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)
Flow Rate All of the above methods have a flow rate of either 20 mls/min (Small Scale) or 40 mls/min (Large Scale).
Chiral HPLC Apparatus and conditions used to characterize enantiomeric purity of selected samples was as follows:
Method (A)
Instrument: Agilent 1100 Series Liquid Chromatogram
Column: Chiralpak AD (250 mm×4.6 mm; 10 um particle size)
Mobile phase: Heptane:absolute ethanol (70:30) v/v pump-mixed
Flow rate: 1 ml/min
Temperature: Ambient
U.V. Wavelength: 215 nm
Method (B)
Instrument: Agilent 1100 Series Liquid Chromatogram
Column: Chiralpak AD (250 mm×4.6 mm; 10 um particle size)
Mobile phase: Heptane:absolute ethanol (50:50) v/v pump-mixed
Flow rate: 1 ml/min
Temperature: Ambient
U.V. Wavelength: 215 nm
Method (C)
Instrument: Agilent 1100 Series Liquid Chromatogram
Column: Chiralpak AD (250 mm×4.6 mm; 10 um particle size)
Mobile phase: Heptane:absolute ethanol (80:20) v/v pump-mixed
Flow rate: 1 ml/min
Temperature: Ambient
U.V. Wavelength: 215 nm
Method (D)
Instrument: Agilent 1100 Series Liquid Chromatogram
Column: Chiralpak AS (250 mm×4.6 mm; 10 um particle size)
Mobile phase: Heptane:absolute ethanol (80:20) v/v pump-mixed
Flow rate: 1 ml/min
Temperature: Ambient
U.V. Wavelength: 215 nm
Liquid Chromatography/Mass Spectrometry Analysis of the above Examples 1-71 and 74-78 by Liquid Chromatography/Mass Spectrometry (LC/MS) was carried out using the following apparatus and conditions:
Hardware
Agilent 1100 Gradient Pump
Agilent 1100 Autosampler
Agilent 1100 DAD Detector
Agilent 1100 Degasser
Agilent 1100 Oven
Agilent 1100 Controller
Waters ZQ Mass Spectrometer
Sedere Sedex 85
Software
Waters MassLynx version 4.0 SP2
Column The column used is a Waters Atlantis, the dimensions of which are 4.6 mm×50 mm. The stationary phase particle size is 3 µm.
Solvents
A: Aqueous solvent=Water+0.05% Formic Acid
B: Organic solvent=Acetonitrile+0.05% Formic Acid
Method The generic method used has a 5 minute runtime.

| Time/min | % B |
| --- | --- |
| 0 | 3 |
| 0.1 | 3 |
| 4 | 97 |
| 4.8 | 97 |
| 4.9 | 3 |
| 5.0 | 3 |

The above method has a flow rate of 3 ml/mins.
The injection volume for the generic method is 5 ul.
The column temperature is 30 deg.
The UV detection range is from 220 to 330 nm.
Analysis of the above Examples 72, 73 and 79-123 by Liquid Chromatography/Mass Spectrometry (LC/MS) was carried out using the following apparatus and conditions:
Hardware
Agilent 1100 Gradient Pump
Agilent 1100 Autosampler
Agilent 1100 DAD Detector
Agilent 1100 Degasser
Agilent 1100 Oven
Agilent 1100 Controller
Waters ZQ Mass Spectrometer
Sedere Sedex 85
Software
Waters MassLynx version 4.1
Column The HPLC analysis was conducted on a Sunfire C18 column (30 mm×4.6 mm i.d. 3.5 µm packing diameter) at 30 degrees centigrade.
Solvents
A=0.1% v/v solution of Formic Acid in Water.
B=0.1% v/v solution of Formic Acid in Acetonitrile.

Method

The generic method used has a 5 minute runtime. The gradient employed was:

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

Pharmacological Data

Compounds of the invention may be tested for in vitro biological activity at the P2X7 receptor in accordance with the following studies:

Ethidium Accumulation Assay

Studies were performed using NaCl assay buffer of the following composition (in mM): 140 mM NaCl, HEPES 10, N-methyl-D-glucamine 5, KCl 5.6, D-glucose 10, $CaCl_2$ 0.5 (pH 7.4). HEK293 cells, expressing human recombinant P2X7 receptors, were grown in poly-L-lysine pretreated 96 well plates for 18-24 h. (The cloning of the human P2X7 receptor is described in U.S. Pat. No. 6,133,434). The cells were washed twice with 350 µl of assay buffer before addition of 50 µl of antagonist. The cells were then incubated at room temperature (19-21° C.) for 30 min before addition of ATP and ethidium (100 µM final assay concentration). The ATP concentration was chosen to be close to the $EC_{80}$ for the receptor type and was 1 mM for studies on the human P2X7 receptor. Incubations were continued for 8 or 16 min and were terminated by addition of 25 µl of 1.3M sucrose containing 5 mM of the P2X7 receptor antagonist reactive black 5 (Aldrich). Cellular accumulation of ethidium was determined by measuring fluorescence (excitation wavelength of 530 nm and emission wavelength of 620 nm) from below the plate with a Can berra Packard Fluorocount (Pangbourne, UK). Antagonist $pIC_{50}$ values for blocking ATP responses were determined using iterative curve fitting techniques.

Fluorescent Imaging Plate Reader (FLIPR) Ca Assay

Studies were performed using NaCl assay buffer of the following composition (in mM) for human P2X7: 137 NaCl; 20 HEPES; 5.37 KCl; 4.17 $NaHCO_3$; 1 $CaCl_2$; 0.5 $MgSO_4$; and 1 g/L of D-glucose (pH 7.4).

HEK293 cells, expressing human recombinant P2X7 receptors, were grown in poly-L-lysine pretreated 384 well plates for 42-48 h. (The cloning of the human P2X7 receptor is described in U.S. Pat. No. 6,133,434). The cells were washed three times with 80 µl of assay buffer, loaded for 1 h at 37° C. with 2 µM Fluo4 (Teflabs), washed three times again, and left with 30 µl buffer before the addition of 10 µl of 4× concentrated antagonist. The cells were then incubated at room temperature for 30 mins before addition (online, by FLIPR384 or FLIPR3 instrument (Molecular Devices)) of Benzoylbenzoyl-ATP (BzATP) 60 µM final assay concentration. The BzATP concentration was chosen to be close to the $EC_{80}$ for the receptor type. Incubations and reading were continued for 90 sec, and intracellular calcium increase was determined by measuring fluorescence (excitation wavelength of 488 nm and emission wavelength of 516 nm) from below the plate, with FLIPR CCD camera. Antagonist $pIC_{50}$ values for blocking BzATP responses were determined using iterative curve fitting techniques.

The compounds of Examples 1-127 were tested in the FLIPR Ca Assay and/or the Ethidium Accumulation Assay for human P2X7 receptor antagonist activity and found to have pIC50 values >4.7 in the FLIPR Ca Assay and/or pIC50 values >5.5 in the Ethidium Accumulation Assay. The compounds of Examples E1 to E5, E7, E8, E10 to E13, E15, E18, E19, E21, E23, E25 to E28, E30, E32 to E35, E39, E41, E42, E45, E51, E52, E54, E55, E57 to E61, E64 to E70, E72 to E79, E81, E82, E85, E86, E88, E89, E91 to E97, E99, E100, E102, E104 to E108, E110 to E113, E115 to E120, and E122 to E127 were found to have pIC50 values of about 7.5 or more in the Ethidium Accumulation Assay.

The invention claimed is:

1. A compound of formula (I):

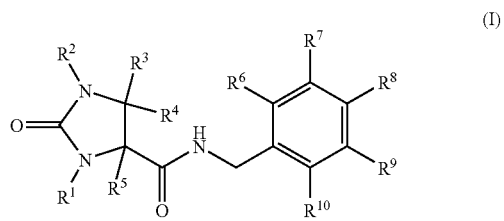

wherein:
R$^1$ represents hydrogen, $C_{1-6}$ alkyl, $C_{2-6}$ alkenyl, $C_{2-6}$ alkynyl, $C_{3-6}$ cycloalkyl, $C_{3-6}$ cycloalkylmethyl-, pyridinylmethyl- or benzyl, and wherein any of said $C_{1-6}$ alkyl, $C_{2-6}$ alkenyl, $C_{2-6}$ alkynyl, $C_{3-6}$ cycloalkyl, $C_{3-6}$ cycloalkylmethyl-, pyridinylmethyl- or benzyl is optionally substituted with 1, 2 or 3 halogen atoms; or an unsubstituted phenyl;

R$^2$ represents hydrogen, $C_{1-6}$ alkyl, $C_{2-6}$ alkenyl, $C_{2-6}$ alkynyl, $C_{3-6}$ cycloalkyl, $C_{3-6}$ cycloalkylmethyl-, —(CR$^x$R$^y$)$_n$—NR$^{11}$R$^{12}$, $C_{6-10}$ arylmethyl-, heterocyclyl-(CR$^x$R$^y$)$_n$— or heteroaryl-(CR$^x$R$^y$)$_n$—; and wherein any of said $C_{1-6}$ alkyl, $C_{2-6}$ alkenyl, $C_{2-6}$ alkynyl, $C_{3-6}$ cycloalkyl, $C_{3-6}$ cycloalkylmethyl-, $C_{6-10}$ arylmethyl-, heterocyclyl-(CR$^x$R$^y$)$_n$— or heteroaryl-(CR$^x$R$^y$)$_n$— is optionally substituted with 1, 2 or 3 halogen atoms or $C_{1-6}$ alkyl groups, or the heteroaryl-(CR$^x$R$^y$)$_n$— is optionally substituted on the heteroaryl ring with one $C_{1-3}$ alkoxy, cyano or trifluoromethyl group;

R$^3$, R$^4$ and R$^5$ independently represent hydrogen, fluorine or methyl; and R$^6$, R$^7$, R$^8$, R$^9$ and R$^{10}$ independently represent hydrogen, halogen, cyano, $C_{1-6}$ alkyl, $C_{2-6}$ alkenyl, $C_{2-6}$ alkynyl, $C_{3-6}$ cycloalkyl or phenyl, and any of said $C_{1-6}$ alkyl, $C_{2-6}$ alkenyl, $C_{2-6}$ alkynyl, $C_{3-6}$ cycloalkyl or phenyl is optionally substituted with 1, 2 or 3 halogen atoms; or R$^9$ and R$^{10}$ together with the carbon atoms to which they are attached form a benzene ring which is optionally substituted with 1, 2 or 3 halogen atoms;

R$^x$ and R$^y$ independently represent hydrogen or $C_{1-6}$ alkyl;

R$^{11}$ and R$^{12}$ independently represent hydrogen or $C_{1-6}$ alkyl;

n represents an integer from 0 to 4;

with the proviso that when R$^6$ and R$^{10}$ independently represent hydrogen or fluorine, at least one of R$^7$, R$^8$ and R$^9$ is a halogen atom, or only one of R$^7$, R$^8$ and R$^9$ is a $CF_3$ group;

or a pharmaceutically acceptable salt thereof.

2. The compound or salt as claimed in claim 1, wherein $R^1$ represents methyl, ethyl, or ethyl substituted with 1, 2 or 3 fluorine atoms.

3. The compound or salt as claimed in claim 1, wherein $R^1$ represents methyl.

4. The compound or salt as claimed in claim 1, wherein $R^2$ represents pyridinyl, pyrimidinyl, imidazolyl or pyrazolyl, wherein any of said groups are optionally substituted with 1 or 2 fluorine or chlorine atoms, with 1 or 2 methyl groups, or with one methoxy, cyano or trifluoromethyl group.

5. The compound or salt as claimed in claim 1, wherein $R^2$ represents hydrogen, methyl, ethyl, or ethyl substituted with 1, 2 or 3 fluorine atoms.

6. The compound or salt as claimed in claim 1, wherein:
$R^1$ and $R^2$ both represent methyl, or
$R^1$ represents methyl and $R^2$ represents hydrogen.

7. The compound or salt as claimed in claim 1, wherein $R^3$, $R^4$ and $R^5$ all represent hydrogen.

8. The compound or salt as claimed in claim 1, wherein $R^6$, $R^7$, $R^8$, $R^9$ and $R^{10}$ independently represent hydrogen, halogen, methyl or trifluoromethyl.

9. The compound or salt as claimed in claim 1, wherein:
$R^6$ and $R^7$ both represent hydrogen,
$R^8$ represents hydrogen, chlorine or fluorine,
$R^9$ represents hydrogen, chlorine, fluorine or trifluoromethyl, and
$R^{10}$ represents chlorine, fluorine, methyl or trifluoromethyl.

10. The compound or salt as claimed in claim 1, wherein:
$R^6$ represents hydrogen, chlorine, fluorine or methyl,
$R^7$ represents hydrogen,
$R^8$ represents chlorine or fluorine,
$R^9$ represents hydrogen, and
$R^{10}$ represents chlorine or methyl.

11. The compound or salt as claimed in claim 1, wherein:
$R^6$, $R^7$ and $R^8$ each represent hydrogen, $R^9$ represents trifluoromethyl, and $R^{10}$ represents chlorine;
$R^6$, $R^7$ and $R^9$ each represent hydrogen and $R^8$ and $R^{10}$ both represent chlorine;
$R^6$ and $R^7$ both represent hydrogen, $R^8$ and $R^9$ both represent fluorine, and $R^{10}$ represents chlorine;
$R^6$, $R^7$ and $R^8$ each represent hydrogen, $R^9$ represents trifluoromethyl, and $R^{10}$ represents methyl;
$R^6$ and $R^7$ both represent hydrogen, $R^8$ represents fluorine, $R^9$ represents trifluoromethyl, and $R^{10}$ represents chlorine;
$R^6$ is methyl, $R^7$ and $R^9$ both represent hydrogen, and $R^8$ and $R^{10}$ both represent chlorine;
$R^6$, $R^8$ and $R^{10}$ each represent chlorine, and $R^7$ and $R^9$ both represent hydrogen;
$R^6$, $R^7$ and $R^8$ each represent hydrogen, $R^9$ represents trifluoromethyl, and $R^{10}$ represents fluorine;
$R^6$, $R^7$ and $R^9$ each represent hydrogen, $R^8$ represents fluorine, and $R^{10}$ represents chlorine;
$R^6$, $R^7$ and $R^9$ each represent hydrogen, $R^8$ represents chlorine, and $R^{10}$ represents methyl;
$R^6$, $R^7$ and $R^8$ each represent hydrogen, $R^9$ represents chlorine, and $R^{10}$ represents methyl;
$R^6$ and $R^7$ both represent hydrogen, $R^8$ represents fluorine, and $R^9$ and $R^{10}$ both represent chlorine;
$R^6$, $R^7$ and $R^8$ each represent hydrogen and $R^9$ and $R^{10}$ both represent chlorine; or
$R^6$ is fluorine, $R^7$ and $R^9$ both represent hydrogen, and $R^8$ and $R^{10}$ both represent chlorine.

12. The compound or salt as claimed in claim 11, wherein:
$R^6$, $R^7$ and $R^8$ each represent hydrogen, $R^9$ represents trifluoromethyl, and $R^{10}$ represents chlorine;
$R^6$, $R^7$ and $R^9$ each represent hydrogen and $R^8$ and $R^{10}$ both represent chlorine;
$R^6$ and $R^7$ both represent hydrogen, $R^8$ and $R^9$ both represent fluorine, and $R^{10}$ represents chlorine;
$R^6$, $R^7$ and $R^8$ each represent hydrogen, $R^9$ represents trifluoromethyl, and $R^{10}$ represents methyl;
$R^6$ and $R^7$ both represent hydrogen, $R^8$ represents fluorine, $R^9$ represents trifluoromethyl, and $R^{10}$ represents chlorine;
$R^6$ is methyl, $R^7$ and $R^9$ both represent hydrogen, and $R^8$ and $R^{10}$ both represent chlorine; or
$R^6$, $R^8$ and $R^{10}$ each represent chlorine, and $R^7$ and $R^9$ both represent hydrogen.

13. The compound or salt as claimed in claim 12, wherein:
$R^6$, $R^7$ and $R^8$ each represent hydrogen, $R^9$ represents trifluoromethyl, and $R^{10}$ represents chlorine;
$R^6$, $R^7$ and $R^9$ each represent hydrogen and $R^8$ and $R^{10}$ both represent chlorine; or
$R^6$ and $R^7$ both represent hydrogen, $R^8$ and $R^9$ both represent fluorine, and $R^{10}$ represents chlorine.

14. The compound or salt as claimed in claim 1, which is:
N-{[2-chloro-3-(trifluoromethyl)phenyl]methyl}-1,3-dimethyl-2-oxo-4-imidazolidinecarboxamide,
N-[(2,4-dichlorophenyl)methyl]-1,3-dimethyl-2-oxo-4-imidazolidinecarboxamide,
N-[(2-chloro-3,4-difluorophenyl)methyl]-1,3-dimethyl-2-oxo-4-imidazolidinecarboxamide,
N-{[2-fluoro-3-(trifluoromethyl)phenyl]methyl}-1,3-dimethyl-2-oxo-4-imidazolidinecarboxamide,
1,3-dimethyl-2-oxo-N-[(2,3,4-trifluorophenyl)methyl]-4-imidazolidinecarboxamide,
N-[(2-chloro-4-fluorophenyl)methyl]-1,3-dimethyl-2-oxo-4-imidazolidinecarboxamide,
N-{[2-chloro-3-(trifluoromethyl)phenyl]methyl}-3-methyl-2-oxo-4-imidazolidinecarboxamide,
N-{[2-Chloro-3-(trifluoromethyl)phenyl]methyl}-3-methyl-2-oxo-1-(2-pyrimidinyl)-4-imidazolidinecarboxamide,
N-{[2-Chloro-3-(trifluoromethyl)phenyl]methyl}-3-methyl-2-oxo-1-(4-piperidinyl)-4-imidazolidinecarboxamide,
N-{[2-Chloro-3-(trifluoromethyl)phenyl]methyl}-3-methyl-2-oxo-1-(3-pyridinyl)-4-imidazolidinecarboxamide,
N-{[2-Chloro-3-(trifluoromethyl)phenyl]methyl}-3-methyl-1-(6-methyl-3-pyridinyl)-2-oxo-4-imidazolidinecarboxamide,
N-{[2-Chloro-3-(trifluoromethyl)phenyl]methyl}-3-methyl-1-(2-methyl-4-pyridinyl)-2-oxo-4-imidazolidinecarboxamide,
N-[(2,4-Dichlorophenyl)methyl]-3-methyl-1-(2-methyl-3-pyridinyl)-2-oxo-4-imidazolidinecarboxamide,
N-{[2-Chloro-3-(trifluoromethyl)phenyl]methyl}-3-methyl-1-(2-methyl-4-pyridinyl)-2-oxo-4-imidazolidinecarboxamide,
N-[(2-Chloro-3,4-difluorophenyl)methyl]-3-methyl-1-(2-methyl-3-pyridinyl)-2-oxo-4-imidazolidinecarboxamide,
N-{[2-Chloro-3-(trifluoromethyl)phenyl]methyl}-3-methyl-2-oxo-1-(2-pyridinyl)-4-imidazolidinecarboxamide,
N-[(2-Chloro-3,4-difluorophenyl)methyl]-3-methyl-1-(3-methyl-2-pyridinyl)-2-oxo-4-imidazolidinecarboxamide,
N-{[2-Chloro-3-(trifluoromethyl)phenyl]methyl}-3-methyl-1-(3-methyl-2-pyridinyl)-2-oxo-4-imidazolidinecarboxamide, N-[(2,4-Dichlorophenyl)methyl]-3-methyl-1-(3-methyl-2-pyridinyl)-2-oxo-4-imidazolidinecarboxamide,
N-[(2-Chloro-3,4-difluorophenyl)methyl]-3-methyl-2-oxo-4-imidazolidinecarboxamide,
N-[(2,4-Dichlorophenyl)methyl]-3-methyl-2-oxo-4-imidazolidinecarboxamide,
N-[(2,4-Dichlorophenyl)methyl]-3-methyl-2-oxo-1-(2-pyrimidinyl)-4-imidazolidinecarboxamide,
N-[(2-Chloro-4-fluorophenyl)methyl]-3-methyl-2-oxo-1-(2-pyrimidinyl)-4-imidazolidinecarboxamide,
N-[(2-Chloro-3,4-difluorophenyl)methyl]-3-methyl-2-oxo-1-(2-pyrimidinyl)-4-imidazolidinecarboxamide,
N-[(3-Chloro-2-methylphenyl)methyl]-3-methyl-2-oxo-1-(2-pyrimidinyl)-4-imidazolidinecarboxamide,
N-[(2-Chloro-3,4-difluorophenyl)methyl]-3-methyl-1-(1-methyl-1H-imidazol-4-yl)-2-oxo-4-imidazolidinecarboxamide,
N-[(2-Chloro-3,4-difluorophenyl)methyl]-3-methyl-1-(1-methyl-1H-pyrazol-5-yl)-2-oxo-4-imidazolidinecarboxamide,
N-{[2-Chloro-3-(trifluoromethyl)phenyl]methyl}-3-methyl-1-[2-(4-morpholinyl)ethyl]-2-oxo-4-imidazolidinecarboxamide, or
N-{[2-Chloro-3-(trifluoromethyl)phenyl]methyl}-3-methyl-2-oxo-1-(5-pyrimidinyl)-4-imidazolidinecarboxamide.

15. The compound or salt as claimed in claim 1, which is:
N-{[2-Chloro-3-(trifluoromethyl)phenyl]methyl}-3-methyl-2-oxo-1-[4-(trifluoromethyl)-2-pyrimidinyl]-4-imidazolidinecarboxamide,
N-[(2,4-Dichlorophenyl)methyl]-3-methyl-2-oxo-1-[4-(trifluoromethyl)-2-pyrimidinyl]-4-imidazolidinecarboxamide,
N-{[2-Chloro-3-(trifluoromethyl)phenyl]methyl}-1-(2,6-dimethyl-3-pyridinyl)-3-methyl-2-oxo-4-imidazolidinecarboxamide,
N-[(2,4-Dichlorophenyl)methyl]-1-(2,6-dimethyl-3-pyridinyl)-3-methyl-2-oxo-4-imidazolidinecarboxamide,
N-{[2-Chloro-3-(trifluoromethyl)phenyl]methyl}-3-methyl-1-(1-methyl-1H-imidazol-4-yl)-2-oxo-4-imidazolidinecarboxamide,
N-[(2,4-Dichlorophenyl)methyl]-3-methyl-1-(1-methyl-1H-imidazol-4-yl)-2-oxo-4-imidazolidinecarboxamide,
N-{[2-Chloro-3-(trifluoromethyl)phenyl]methyl}-3-methyl-1-(1-methyl-1H-imidazol-2-yl)-2-oxo-4-imidazolidinecarboxamide,
N-[(2,4-Dichlorophenyl)methyl]-3-methyl-1-(1-methyl-1H-imidazol-5-yl)-2-oxo-4-imidazolidinecarboxamide,
N-{[2-Chloro-3-(trifluoromethyl)phenyl]methyl}-3-methyl-1-(1-methyl-1H-imidazol-5-yl)-2-oxo-4-imidazolidinecarboxamide,
N-{[2-Chloro-3-(trifluoromethyl)phenyl]methyl}-3-methyl-2-oxo-1-[6-(trifluoromethyl)-4-pyrimidinyl]-4-imidazolidinecarboxamide,
N-[(2,4-Dichlorophenyl)methyl]-1-(6-fluoro-3-pyridinyl)-3-methyl-2-oxo-4-imidazolidinecarboxamide,
N-{[2-Chloro-3-(trifluoromethyl)phenyl]methyl}-1-(6-fluoro-3-pyridinyl)-3-methyl-2-oxo-4-imidazolidinecarboxamide,
N-[(2,4-Dichlorophenyl)methyl]-1-(2-fluoro-3-pyridinyl)-3-methyl-2-oxo-4-imidazolidinecarboxamide,
N-{[2-Chloro-3-(trifluoromethyl)phenyl]methyl}-1-(2-fluoro-3-pyridinyl)-3-methyl-2-oxo-4-imidazolidinecarboxamide,
N-[(2,4-Dichlorophenyl)methyl]-3-methyl-1-[6-(methyloxy)-3-pyridinyl]-2-oxo-4-imidazolidinecarboxamide,
N-{[2-chloro-3-(trifluoromethyl)phenyl]methyl}-3-methyl-1-[6-(methyloxy)-3-pyridinyl]-2-oxo-4-imidazolidinecarboxamide,
N-[(2,4-Dichlorophenyl)methyl]-1-methyl-2-oxo-3-(2,2,2-trifluoroethyl)-4-imidazolidinecarboxamide,
N-[(2,4-Dichlorophenyl)methyl]-3-ethyl-1-methyl-2-oxo-4-imidazolidinecarboxamide,
N-{[2-Chloro-3-(trifluoromethyl)phenyl]methyl}-3-ethyl-1-methyl-2-oxo-4-imidazolidinecarboxamide,
N-[(2-Chloro-4-fluorophenyl)methyl]-3-ethyl-1-methyl-2-oxo-4-imidazolidinecarboxamide,
N-{[2-Chloro-3-(trifluoromethyl)phenyl]methyl}-3-methyl-2-oxo-1-(2-pyrazinyl)-4-imidazolidinecarboxamide,
1-(2-Chloro-3-pyridinyl)-N-[(2,4-dichlorophenyl)methyl]-3-methyl-2-oxo-4-imidazolidinecarboxamide,
N-[(2-Chloro-3,4-difluorophenyl)methyl]-1-(2-chloro-3-pyridinyl)-3-methyl-2-oxo-4-imidazolidinecarboxamide,
1-(2-Chloro-3-pyridinyl)-N-{[2-chloro-3-(trifluoromethyl)phenyl]methyl}-3-methyl-2-oxo-4-imidazolidinecarboxamide,
3-Methyl-N-{[2-methyl-3-(trifluoromethyl)phenyl]methyl}-2-oxo-4-imidazolidinecarboxamide,
N-[(2,3-Dichlorophenyl)methyl]-3-methyl-2-oxo-4-imidazolidinecarboxamide,
N-[(3-Chloro-2-methylphenyl)methyl]-3-methyl-2-oxo-4-imidazolidinecarboxamide,
N-[(2,4-Dichloro-6-methylphenyl)methyl]-3-methyl-2-oxo-4-imidazolidinecarboxamide,
N-[(2,4-Dichlorophenyl)methyl]-1-(5-fluoro-2-pyrimidinyl)-3-methyl-2-oxo-4-imidazolidinecarboxamide,
N-[(2,4-Dichlorophenyl)methyl]-3-ethyl-2-oxo-4-imidazolidinecarboxamide,
N-{[2-Chloro-3-(trifluoromethyl)phenyl]methyl}-3-ethyl-2-oxo-4-imidazolidinecarboxamide,
N-[(2,4-Dichlorophenyl)methyl]-3-methyl-1-[4-(methyloxy)-2-pyrimidinyl]-2-oxo-4-imidazolidinecarboxamide,
1-(5-Chloro-2-pyrimidinyl)-N-[(2,4-dichlorophenyl)methyl]-3-methyl-2-oxo-4-imidazolidinecarboxamide,
N-[(2,4-Dichlorophenyl)methyl]-3-methyl-1-(6-methyl-3-pyridinyl)-2-oxo-4-imidazolidinecarboxamide,
N-[(2-Chloro-3,4-difluorophenyl)methyl]-3-methyl-1-(6-methyl-3-pyridinyl)-2-oxo-4-imidazolidinecarboxamide,
N-[(2,4-Dichlorophenyl)methyl]-1-(2-fluoro-4-pyridinyl)-3-methyl-2-oxo-4-imidazolidinecarboxamide,
N-[(2-Chloro-3,4-difluorophenyl)methyl]-1-(2-fluoro-4-pyridinyl)-3-methyl-2-oxo-4-imidazolidinecarboxamide,
N-[(3-Chloro-2-methylphenyl)methyl]-1,3-dimethyl-2-oxo-4-imidazolidinecarboxamide,
N-[(2,3-Dichlorophenyl)methyl]-1,3-dimethyl-2-oxo-4-imidazolidinecarboxamide,
N-[(2,3-Dichloro-4-fluorophenyl)methyl]-1,3-dimethyl-2-oxo-4-imidazolidinecarboxamide,
N-{[2-Chloro-4-fluoro-3-(trifluoromethyl)phenyl]methyl}-1,3-dimethyl-2-oxo-4-imidazolidinecarboxamide,
N-[(2,4-Dichloro-6-methylphenyl)methyl]-1,3-dimethyl-2-oxo-4-imidazolidinecarboxamide,
1,3-Dimethyl-N-{[2-methyl-3-(trifluoromethyl)phenyl]methyl}-2-oxo-4-imidazolidinecarboxamide, N-[(4-Chloro-2-methylphenyl)methyl]-1,3-dimethyl-2-oxo-4-imidazolidinecarboxamide,
N-[(2-Chloro-4-cyanophenyl)methyl]-1,3-dimethyl-2-oxo-4-imidazolidinecarboxamide,
N-[(2,4-Dichlorophenyl)methyl]-3-(2,2-difluoroethyl)-1-methyl-2-oxo-4-imidazolidinecarboxamide,
N-[(2,4-Dichlorophenyl)methyl]-1-(3-fluoro-2-pyridinyl)-3-methyl-2-oxo-4-imidazolidinecarboxamide,
N-[(2,4-Dichlorophenyl)methyl]-3-methyl-1-(1-methyl-1H-pyrazol-5-yl)-2-oxo-4-imidazolidinecarboxamide,
1-(2-Cyano-3-pyridinyl)-N-[(2,4-dichlorophenyl)methyl]-3-methyl-2-oxo-4-imidazolidinecarboxamide,
N-[(2,4-Dichlorophenyl)methyl]-1-(2,2-difluoroethyl)-3-methyl-2-oxo-4-imidazolidinecarboxamide,
N-[(2,4-Dichlorophenyl)methyl]-3-methyl-2-oxo-1-(2,2,2-trifluoroethyl)-4-imidazolidinecarboxamide,
N-[(2,4-Dichlorophenyl)methyl]-1-(2-fluoroethyl)-3-methyl-2-oxo-4-imidazolidinecarboxamide,
N-[(2,4-Dichlorophenyl)methyl]-1-ethyl-3-methyl-2-oxo-4-imidazolidinecarboxamide,
N-[(2,4-Dichloro-6-fluorophenyl)methyl]-1,3-dimethyl-2-oxo-4-imidazolidinecarboxamide,
1,3-Dimethyl-2-oxo-N-[(2,4,6-trichlorophenyl)methyl]-4-imidazolidinecarboxamide,
N-[(2,4-Dichloro-6-fluorophenyl)methyl]-3-methyl-2-oxo-4-imidazolidinecarboxamide,
3-Methyl-2-oxo-N-[(2,4,6-trichlorophenyl)methyl]-4-imidazolidinecarboxamide,
N-[(2,4-Dichlorophenyemethyl]-3-methyl-1-(1-methylethyl)-2-oxo-4-imidazolidinecarboxamide,
1-(Cyclopropylmethyl)-N-[(2,4-dichlorophenyl)methyl]-3-methyl-2-oxo-4-imidazolidinecarboxamide,
1-(Cyclobutylmethyl)-N-[(2,4-dichlorophenyl)methyl]-3-methyl-2-oxo-4-imidazolidinecarboxamide, or
1-Cyclopentyl-N-[(2,4-dichlorophenyl)methyl]-3-methyl-2-oxo-4-imidazolidinecarboxamide.

16. A compound which is N-[(2,4-dichlorophenyl)methyl]-3-methyl-2-oxo-4-imidazolidinecarboxamide of the formula:

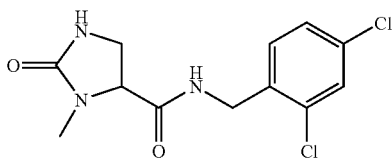

or a pharmaceutically acceptable salt thereof.

17. The compound or salt as claimed in claim 1, which is a compound of formula (IA) or a pharmaceutically acceptable salt thereof:

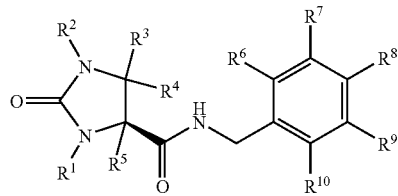

wherein:
R$^1$ represents C$_{1-4}$ alkyl or C$_{3-4}$ cycloalkyl, any of which is optionally substituted with 1, 2 or 3 fluorine atoms; and
R$^2$, R$^x$, R$^y$, R$^3$, R$^4$, R$^5$, R$^6$, R$^7$, R$^8$, R$^9$, R$^{10}$, R$^{11}$, R$^{12}$, R$^x$, R$^y$ and n are as defined in claim 1;
and wherein more than 50% by molarity of the compound of formula (IA) or the pharmaceutically acceptable salt thereof has the indicated stereochemistry at the ring-carbon atom bonded to R$^5$.

18. The compound or salt as claimed in claim 17, wherein R$^1$ represents methyl or ethyl.

19. The compound or salt as claimed in claim 17, wherein:
R$^1$ and R$^2$ both represent methyl, or
R$^1$ represents methyl and R$^2$ represents hydrogen.

20. The compound or salt as claimed in claim 19, wherein R$^3$, R$^4$ and R$^5$ each represent hydrogen.

21. The compound or salt as claimed in claim 20, wherein:
R$^6$ and R$^7$ both represent hydrogen,
R$^8$ represents hydrogen, chlorine or fluorine,
R$^9$ represents hydrogen, chlorine, fluorine or trifluoromethyl, and
R$^{10}$ represents chlorine or methyl,
wherein one or both of R$^8$ and R$^9$ are other than hydrogen.

22. The compound or salt as claimed in claim 20, wherein:
R$^6$ represents hydrogen, chlorine, fluorine or methyl,
R$^7$ represents hydrogen,
R$^8$ represents chlorine or fluorine,
R$^9$ represents hydrogen, and
R$^{10}$ represents chlorine or methyl.

23. The compound or salt as claimed in claim 22, wherein R$^8$ represents chlorine.

24. The compound or salt as claimed in claim 23, wherein:
R$^1$ represents methyl,
R$^2$, R$^6$, R$^7$ and R$^9$ each represent hydrogen, and
R$^8$ and R$^{10}$ each represent chlorine.

25. The compound or salt as claimed in claim 20, wherein:
R$^6$, R$^7$ and R$^8$ each represent hydrogen, R$^9$ represents trifluoromethyl, and R$^{10}$ represents chlorine;
R$^6$, R$^7$ and R$^9$ each represent hydrogen and R$^8$ and R$^{10}$ both represent chlorine; or
R$^6$ and R$^7$ both represent hydrogen, R$^8$ and R$^9$ both represent fluorine, and R$^{10}$ represents chlorine.

26. A pharmaceutical composition which comprises the compound or salt as defined in claim 1, and a pharmaceutically acceptable carrier or excipient.

* * * * *